(12) United States Patent
Ludlow et al.

(10) Patent No.: US 11,344,471 B2
(45) Date of Patent: May 31, 2022

(54) SYSTEMS AND METHODS FOR STIMULATING SWALLOWING

(71) Applicant: Passy-Muir, Inc., Irvine, CA (US)

(72) Inventors: Christy Leslie Ludlow, Castleton, VA (US); Larry Lee Hood, Irvine, CA (US)

(73) Assignee: Passy-Muir, Inc., Irvine, CA (US)

( * ) Notice: Subject to any disclaimer, the term of this patent is extended or adjusted under 35 U.S.C. 154(b) by 1382 days.

(21) Appl. No.: 15/372,211

(22) Filed: Dec. 7, 2016

(65) Prior Publication Data

US 2017/0273862 A1    Sep. 28, 2017

Related U.S. Application Data

(63) Continuation of application No. 13/799,549, filed on Mar. 13, 2013, now abandoned.

(51) Int. Cl.
*A61H 23/00*    (2006.01)
*A61H 9/00*    (2006.01)
(Continued)

(52) U.S. Cl.
CPC ........... *A61H 23/00* (2013.01); *A61H 9/0078* (2013.01); *A61N 5/0622* (2013.01);
(Continued)

(58) Field of Classification Search
CPC ............... A61H 23/00; A61H 9/0078; A61H 2230/201; A61H 2230/405;
(Continued)

(56) References Cited

U.S. PATENT DOCUMENTS

| 4,143,648 A | 3/1979 | Cohen et al. |
| 4,685,448 A | 8/1987 | Shames et al. |

(Continued)

FOREIGN PATENT DOCUMENTS

| CN | 101716394 | 6/2010 |
| EP | 0 226 333 A1 | 6/1987 |

(Continued)

OTHER PUBLICATIONS

Kamarunas et al., "Vibration overlying the larynx increases swallowing in chronic oropharyngeal dysphagia," Original Research, pp. 1-41, Jul. 17, 2017.

(Continued)

*Primary Examiner* — Quang D Thanh
(74) *Attorney, Agent, or Firm* — Knobbe, Martens, Olson & Bear, LLP

(57) ABSTRACT

A device includes a first vibrational transducer and a second vibrational transducer. The first vibrational transducer has a first vibrating property. The second vibrotactile stimulator has a second vibrating property different than the first vibrating property. A collar may be configured to position the first vibrational transducer and the second vibrational transducer over a neck of a subject. A method for stimulating swallowing in a subject includes applying a first vibrotactile stimulation and applying a second vibrotactile stimulation to a throat area of the subject. The first vibrotactile stimulation has a first vibrating property and the second vibrotactile stimulation has a second vibrating property different than the first vibrating property. Example vibrating properties include vibrating frequency, vibrating frequency range, wave shape, continuousness, frequency phase, and direction of mechanical force.

13 Claims, 32 Drawing Sheets

US 11,344,471 B2
Page 2

(51) Int. Cl.
*A61N 5/06* (2006.01)
*A61B 5/0205* (2006.01)
*A61N 1/36* (2006.01)
*A61N 7/00* (2006.01)
*A61N 5/067* (2006.01)

(52) U.S. Cl.
CPC .... *A61B 5/0205* (2013.01); *A61H 2201/0207* (2013.01); *A61H 2201/0214* (2013.01); *A61H 2201/10* (2013.01); *A61H 2201/102* (2013.01); *A61H 2201/165* (2013.01); *A61H 2201/1609* (2013.01); *A61H 2201/5002* (2013.01); *A61H 2201/5005* (2013.01); *A61H 2201/5035* (2013.01); *A61H 2201/5038* (2013.01); *A61H 2201/5041* (2013.01); *A61H 2201/5043* (2013.01); *A61H 2201/5084* (2013.01); *A61H 2201/5097* (2013.01); *A61H 2205/04* (2013.01); *A61H 2230/065* (2013.01); *A61H 2230/201* (2013.01); *A61H 2230/208* (2013.01); *A61H 2230/305* (2013.01); *A61H 2230/405* (2013.01); *A61N 5/067* (2021.08); *A61N 2007/0026* (2013.01)

(58) Field of Classification Search
CPC ........ A61H 2230/305; A61H 2230/208; A61H 2230/065; A61H 2205/04; A61H 2201/5097; A61H 2201/5084; A61H 2201/5043; A61H 2201/5041; A61H 2201/5038; A61H 2201/5035; A61H 2201/5005; A61H 2201/5002; A61H 2201/165; A61H 2201/1609; A61H 2201/102; A61H 2201/10; A61H 2201/0214; A61H 2201/0207; A61N 5/0622; A61N 1/36014; A61N 2007/0026; A61N 2005/067; A61B 5/0205
See application file for complete search history.

(56) References Cited

U.S. PATENT DOCUMENTS

| | | |
|---|---|---|
| 5,007,410 A | 4/1991 | DeLaney |
| 5,086,788 A | 2/1992 | Castel et al. |
| 5,111,814 A | 5/1992 | Goldfarb |
| 5,350,407 A | 9/1994 | McClure et al. |
| 5,562,718 A | 10/1996 | Palermo |
| 5,611,771 A | 3/1997 | Taylor |
| 5,725,564 A | 3/1998 | Freed et al. |
| 5,871,508 A | 2/1999 | Thompson et al. |
| 5,891,185 A | 4/1999 | Freed et al. |
| 5,897,579 A | 4/1999 | Sanders |
| 5,987,359 A | 11/1999 | Freed et al. |
| 6,039,679 A | 3/2000 | Yu |
| 6,104,958 A | 8/2000 | Freed et al. |
| 6,131,535 A | 10/2000 | So |
| 6,198,970 B1 | 3/2001 | Freed et al. |
| 6,343,232 B1 | 1/2002 | Mower |
| 6,354,991 B1 | 3/2002 | Gross et al. |
| 6,393,323 B1 | 5/2002 | Sawan et al. |
| 6,484,053 B2 | 11/2002 | Leelamanit et al. |
| 6,735,315 B1 | 5/2004 | Ifukube et al. |
| 7,039,468 B2 | 5/2006 | Freed et al. |
| 7,182,738 B2 | 2/2007 | Bonutti et al. |
| 7,254,444 B2 | 8/2007 | Moore et al. |
| 7,280,873 B2 | 10/2007 | Freed et al. |
| 7,349,739 B2 | 3/2008 | Harry et al. |
| 7,582,066 B2 | 9/2009 | Shimotori |
| 7,606,623 B2 | 10/2009 | Ludlow et al. |
| 7,660,636 B2 | 2/2010 | Castel et al. |
| 8,388,561 B2 | 3/2013 | Ludlow et al. |
| 8,449,445 B2 | 5/2013 | Ludlow et al. |
| 8,579,839 B2 | 11/2013 | Ludlow et al. |
| 8,808,207 B2 | 8/2014 | Ludlow et al. |
| 8,852,074 B2 | 10/2014 | Ludlow et al. |
| 2002/0010495 A1 | 1/2002 | Freed et al. |
| 2002/0049479 A1 | 4/2002 | Pitts |
| 2002/0133194 A1 | 9/2002 | Leelamanit et al. |
| 2003/0093128 A1 | 5/2003 | Freed et al. |
| 2004/0073271 A1 | 4/2004 | Harry et al. |
| 2004/0133133 A1 | 7/2004 | Dreimann et al. |
| 2004/0249320 A1 | 12/2004 | Yamazaki et al. |
| 2004/0267331 A1 | 12/2004 | Koeneman et al. |
| 2005/0049453 A1 | 3/2005 | Faulkner |
| 2005/0049856 A1 | 3/2005 | Baraff |
| 2005/0059909 A1* | 3/2005 | Burgess .................. A61F 7/007 601/15 |
| 2005/0267388 A1 | 12/2005 | Hanna |
| 2006/0030794 A1 | 2/2006 | Nation et al. |
| 2007/0073361 A1* | 3/2007 | Goren ....................... A61B 5/04 607/62 |
| 2007/0293926 A1 | 12/2007 | Dunlay et al. |
| 2008/0077192 A1* | 3/2008 | Harry .................. A61H 23/0263 607/48 |
| 2009/0048645 A1 | 2/2009 | Philipp et al. |
| 2009/0054980 A1 | 2/2009 | Ludlow et al. |
| 2009/0187124 A1 | 7/2009 | Ludlow et al. |
| 2010/0016908 A1 | 1/2010 | Martin et al. |
| 2010/0049103 A1 | 2/2010 | Ludlow et al. |
| 2011/0065979 A1* | 3/2011 | Lehrman ............... A61B 5/4818 600/27 |
| 2011/0125212 A1 | 5/2011 | Tyler |
| 2012/0046579 A1 | 2/2012 | Radl et al. |
| 2012/0296243 A1 | 11/2012 | Ludlow et al. |
| 2013/0102937 A1 | 4/2013 | Ehrenreich et al. |
| 2014/0276270 A1 | 9/2014 | Ludlow et al. |

FOREIGN PATENT DOCUMENTS

| | | |
|---|---|---|
| JP | 62-174788 A | 7/1987 |
| JP | S64-046459 | 2/1989 |
| JP | H06-190017 | 7/1994 |
| JP | H09-084845 | 3/1997 |
| JP | 11-500339 | 1/1999 |
| JP | 2003-111748 | 4/2003 |
| JP | 2006-500994 | 1/2006 |
| JP | 2007-151736 | 6/2007 |
| JP | 2008-520306 | 6/2008 |
| WO | WO 92/21407 | 12/1992 |
| WO | WO 97/15349 | 5/1997 |
| WO | WO 2004/028433 | 4/2004 |
| WO | WO 2006/054118 A1 | 5/2006 |
| WO | WO 2007/123746 | 11/2007 |
| WO | WO 2010/033594 | 3/2010 |

OTHER PUBLICATIONS

Mulheren et al., "Vibration over the larynx increases swallowing and cortical activation for swallowing", J. Neurophysiol., 118:169-1708, Jul. 5, 2017.
Andersen et al., Modulation of heat evoked nociceptive withdrawal reflexes by painful intramuscular conditioning stimulation, Exp Brain Res, 2006, vol. 174, pp. 755-780.
Aviv et al., "Laryngopharyngeal sensory testing with modified barium swallow as predictors of aspiration pneumonia after stroke", Laryngoscope, 107:1254-1260 (1997).
Aviv et al., "Silent laryngopharyngeal sensory deficits after stroke", Ann Otol Rhinol. Laryngol., 106:87-93 (1997).
Aviv et al., "Supraglottic and pharyngeal sensory abnormalities in stroke patients with dysphagia", Ann Otol Rhinol.Laryngol., 105:92-97 (1996).
Bara-Jimenez et al., "Abnormal somatosensory homunculus in dystonia of the hand", Ann Neurol., 44(5):828-831 (1998).
Bara-Jimenez et al., "Sensory discrimination capabilities in patients with focal hand dystonia", Ann Neural., 47(3):377-380 (2000).
Bhadra et al., Extraction Force and Tissue Change During Removal of a Tined Intramuscular Electrode from Rat Gastrocnemius, Annals of Biomedical Engineering, Jun. 2006, vol. 34, Issue No. 6, pp. 1042-1050.

(56) References Cited

OTHER PUBLICATIONS

Bidus et al., "Effects of Adductor Muscle Stimulation on Speech in Abductor Spasmodic Cysphonia", The Laryngoscope, 110:1943-1949 (2000).
Bielamowicz et al., "Effects of botulinum toxin on pathophysiology in spasmodic dysphonia", Ann Otol Rhinol Laryngol, 109: 194-203 (2000).
Burnett et al., "Laryngeal elevation achieved by neuromuscular stimulation at rest", J Appl Physiol, 94(1): 128-134 (2003).
Burnett et al., "Self-Triggered Functional Electrical Stimulation During Swallowing", J Neurophysiol, 94(6):4011-4018 (2005).
Caetano et al., Evidence of vibrotactile input to human auditory cortex, NeuroImage, 2006, vol. 29, pp. 15-28.
Celichowski et al., The time course of the last contractions during incompletely fused tetani of motor units in rat skeletal muscle, Acta Neurobiol. Exp., 2002, vol. 62, pp. 7-17.
Chou et al., Predicting optimal electrical stimulation for repetitive human muscle activation, Journal of Electromyography and Kinesiology, 2005, vol. 15, pp. 300-309.
Conforto et al., "Increase in hand muscle strength of stroke patients after somatosensory stimulation", Ann Neurol, 51(1): 122-125 (2002).
Daly et al., "Performance of an intramuscular electrode during functional neuromuscular stimulation for gait training post stroke", Journal of Rehabilitation Research and Development, 38(5):513-526 (2001).
Davis et al., Quantitative analysis of laryngeal mechanosensitivity in the cat and rabbit, J. Physiol., 1987, vol. 388, pp. 467-485.
De Larminat et al., "Alteration in swallowing reflex after extubation in intensive care unit patients", Crit Care Med, 23(3):486-490 (1995).
De Nil et al., "Kinaesthetic acuity of stutterers and non-stutterers for oral and non-oral movements", Brain, 114:2145-2158 (1991).
Dick et al., "Interaction between central pattern generators for breathing and swallowing in the cat", J Physiol, 465:715-730 (1993).
Experia™: The Next Generation of VitalStim® Therapy brochure, 2007 Encore Medical, L.P. and Affiliates, 2 pages.
Final Office Action issued in U.S. Appl. No. 13/799,549, dated Jun. 8, 2016.
Folstein et al., "Mini-mental state. A practical method for grading the cognitive state of patients for the clinician", J Psychiatr Res, 12(3):189-198 (1975).
Fraser et al., "Differential changes in human pharyngoesophageal motor excitability induced by swallowing, pharyngeal stimulation, and anesthesia", Am J Physiol Gastrointest Liver Physiol, 285(1):G137-144 (2003).
Freed et al., "Electrical Stimulation for Swallowing Disorders Caused by Stroke", Respiratory Care, 46(5):466-474 (2001).
Grottel et al., The Influence of changes in the stimulation pattern on force and fusion in motor units of the rat medial gastrocnemius muscle, Exp Brain Res, 1999, vol. 127, pp. 298-306.
Hägg et al., "Effects of motor and sensory stimulation in stroke patients with long-lasting dysphagia", Dysphagia, 19:219-230 (2004).
Hamdy et al., "Modulation of human swallowing behaviour by thermal and chemical stimulation in health and after brain injury", Neurogastroenterol Motil, 15(1):69-77 (2003).
Handa et al., "Development of Percutaneous Intramuscular Electrode for Multichannel FES System", IEEE Transactions on Biomedical Engineering, 36(7):705-710.
Haslinger et al., "Silent event-related fMRI reveals reduced sensorimotor activation in laryngeal dystonia", Neurology, 65:1562-1569 (2005).
Hrycyshyn et al., "Electromyography of the Oral Stage of Swallowing in Man", Am. J. Anat., 133:333-340 (1972).
Humbert et al., "The effect of surface electrical stimulation on hyolaryngeal movement in normal individuals at rest and during swallowing", J Appl Physiol, 101:1657-1663 (2006).
Humbert et al., The Effect of Surface Electrical Stimulation on Vocal Fold Posiiton, The Laryngoscope, Jan. 2008, vol. 118, pp. 14-19.
International Search Report for International Application No. PCT/US2014/014208 dated Jun. 26, 2014.
Jafari et al., "Sensory regulation of swallowing and airway protection: a role for the internal superior laryngeal nerve in humans", J Physiol, 550(Pt I):287-304 (2003).
Jean, "Control of the central swallowing program by inputs from the peripheral receptors. A review", J Auton. Ner. Syst., 10:225-233 (1984).
Jean, Brain Stem Control of Swollowing: Neuronal Network and Cellular Mechanisms, Physiological Reviews, Apr. 2001, vol. 81, Issue No. 2, pp. 929-969.
Kesar et al., Effect of frequency and pulse duration on human muscle fatigue during repetitive electrical stimulation, Exp Physiol, 2006, vol. 91, Issue No. 6, pp. 967-976.
Kimberley et al., "Electrical stimulation driving functional improvements and cortical changes in subjects with stroke", Experimental Brain Research, 2004, vol. 154, pp. 450-460.
Kitagawa et al., Facilitation of reflex swallowing from the pharynx and larynx, Journal of Oral Science, 2009, vol. 51, Issue No. 2, pp. 167-171.
Knutson et al., Electrode fracture rates and occurrences of infection and granuloma associated with percutaneous intramuscular electrodes in upper-limb functional electrical stimulation applications, Journal of Rehabilitation Research and Development, 2002, vol. 39, Issue No. 6, pp. 671-683.
Leelamanit et al., "Synchronized electrical stimulation in treating pharyngeal dysphagia", Laryngoscope, 112(12):2204-2210 (2002).
Logemann et al., "Effects of a sour bolus on oropharyngeal swallowing measures in patients with neurogenic dysphagia", J Speech Hear Res, 38(3):556-563 (1995).
Logemann, "Noninvasive approaches to deglutitive aspiration", Dysphagia, 8(4):331-333 (1993).
Loucks et al., "Laryngeal muscle responses to mechanical displacement of the thyroid cartilage in humans", J Appl Physiol, 99(3):922-930 (2005).
Lowell et al., "Sensory stimulation activates both motor and sensory components of the swallowing system", NeuroImage, 42:285-295 (2008).
Ludlow et al., "Chronic Intermittent Stimulation of the Thyroarytenoid Muscle Maintains Dynamic Control of Glottal Adduction", Muscle and Nerve, 23:44-57 (2000).
Ludlow et al., "Dynamic aspects of phonatory control in spasmodic dysphonia", J Speech Hear Res, 30:197-206 (1987).
Ludlow et al., "Effects of Surface Electrical Stimulation Both at Rest and During Swallowing in Chronic Pharyngeal Dysphagia", Dysphagia, 22:1-10 (2007).
Ludlow et al., "Three-Dimensional Changes in the Upper Airway During Neuromuscular Stimulation of Laryngeal Muscles", Journal of Artificial Organs, 23:463-465 (1999).
Lundy et al., "Aspiration: Cause and Implications", Otolaryngol Head Neck Surg., 120(4):474-478 (1999).
Marsolais et al., "Implantation techniques and experience with percutaneous intramuscular electrodes in the lower extremities", J. Rehabil. Res. Dev., 23(3):1-8 (1986).
Mifflin, "Intensity and frequency dependence of laryngeal afferent inputs to respiratory hypoglossal motoneurons", J.Appl Physiol, 83:1890-1899 (1997).
Mortimer et al., "Intramuscular Electrical Stimulation: Tissue Damage", Ann. Biomed. Eng., 8:235-244 (1980).
Mortimer et al., Vibrotactile transduction and transducers, J. Acoust. Soc. Am., May 2007, vol. 121, Issue No. 5, pp. 2970-2977.
Nishino et al., "Cough and other reflexes on irritation of airway mucosa in man", Pulm Pharmacol, 9(5-6):285-292 (1996).
Office Action issued in U.S. Appl. No. 13/799,549, dated Sep. 17, 2015.
Ootani et al., "Convergence of afferents from the SLN and GPN in cat medullary swallowing neurons", Brain Res Bull, 37(4):397-404 (1995).

(56) References Cited

OTHER PUBLICATIONS

Park et al., "A pilot exploratory study of oral electrical stimulation on swallow function following stroke: an innovative technique", Dysphagia, 12(3):161-166 (1997).
Pertovaara, Modification of human pain threshold by specific tactile receptors, Acta Physiol Scand, 1979, vol. 107, pp. 339-341.
Peurala et al., "Cutaneous electrical stimulation may enhance sensorimotor recovery in chronic stroke", Clin Rehabil., 16:709-716 (2002).
Pick et al., "Pulmonary aspiration in a long-term care setting: clinical and laboratory observations and an analysis of risk factors", J Am Geriatr Soc, 44(7):763-768 (1996).
Pommerenke, "A study of the sensory areas eliciting the swallowing reflex", American Journal of Physiology, 84(1):36-41 (1927).
Portone et al., "A review of patient adherence to the recommendations for voice therapy", J. Voice, 22:192-196 (2008).
Power et al., "Changes in pharyngeal corticobulbar excitability and swallowing behavior after oral stimulation", Am J Physiol Gastrointest Liver Physiol, 286(1):G45-50 (2004).
Power et al., "Evaluating oral stimulation as a treatment for Dysphagia after stroke", Dysphagia, 21(1):49-55 (2006).
Robbins et al., "Swallowing and dysphagia rehabilitation: translating principles of neural plasticity into clinically orientated evidence", J Speech Lang. Hear. Res., 51:S276-300 (2008).
Scheiner et al., "Design and Clinical Application of a Double Helix Electrode for Functional Electrical Stimulation", IEEE Transactions of Biomedical Engineering, 41(5):425-431 (1994).
Sedory-Holzer et al., "The swallowing side effects of botulinum toxin type A injection in spasmodic dysphonia", Laryngoscope, 106:86-92 (1996).

Setzen et al., "The association between laryngopharyngeal sensory deficits, pharyngeal motor function, and the prevalence of aspiration with thin liquids", Otolaryngol Head Neck Surg, 128(1):99-102 (2003).
Spiro et al., "Activation and Coordination Patterns of the Suprahyoid Muscles During Swallowing", Laryngoscope, 104:1376-1382 (1994).
Stanic et al., "Multichannel Electrical Stimulation for Correction of Hemiplegic Gait", Scand J. Rehabil. Med., 10:75-92 (1978).
Strojnik et al., "Treatment of Drop Foot Using an Implantable Peroneal Underknee Stimulator", Scand J. Rehabil. Med., 19:37-43 (1987).
Struppler et al., "Modulation of sensorimotor performances and cognition abilities induced by RPMS: clinical and experimental investigations", Suppl Clin Neurophysiol., 56:358-367 (2003).
Sundgren et al., "Elevation of the larynx on normal and abnormal cineradiogram", The British Journal of Radiology, 66:768-772(1993).
Theurer et al., "Oropharyngeal stimulation with air-pulse trains increases swallowing frequency in healthy adults", Dysphagia, 20(4):254-260 (2005).
Van Dijk et al., "Effects of transcutaneous electrical nerve stimulation (TENS) on non-pain related cognitive and behavioural functioning", Rev Neurosci., 13:257-270 (2002).
Wakeling et al., Muscle activity damps the soft tissue resonance that occurs in response to pulsed and continuous vibrations, J Appl Physiol, May 17, 2002, vol. 93, pp. 1093-1103.
Waters et al., "Functional Electrical Stimulation of the Peroneal Nerve for Hemiplegia", The Journal of Bone and Joint Surgery, 67:792-793 (1985).
Witteveen et al., Vibro- and Electrotactile User Feedback on Hand Opening for Myoelectric Forearm Prostheses, IEEE Transactions on Biomedical Engineering, Aug. 2012, vol. 59, Issue No. 8, pp. 2219-2226.

\* cited by examiner t=3.33, p=.0025 t=6.285, p≤0.00025

SYSTEMS AND METHODS FOR STIMULATING SWALLOWING

INCORPORATION DATA

This application is a continuation of U.S. patent application Ser. No. 13/799,549, filed Mar. 13, 2013, which is related to U.S. patent application Ser. No. 12/211,633, filed Sep. 16, 2008, U.S. patent application Ser. No. 12/240,398, filed Sep. 29, 2008, U.S. patent application Ser. No. 11/993,094, filed Dec. 19, 2007, PCT Patent App. No. PCT/US2006/025535, filed Jun. 30, 2006, PCT Patent App. No. PCT/US2007/007993, filed Mar. 30, 2007, U.S. Prov. Patent App. Ser. No. 60/695,424, filed Jul. 1, 2005, and U.S. Prov. Patent App. Ser. No. 60/787,215, filed Mar. 30, 2006, are each hereby incorporated by reference in its entirety.

FIELD

The present disclosure relates generally to systems and methods for stimulating swallowing. More specifically, the present disclosure relates generally to systems and methods for vibrotactilely stimulating the throat area of a subject to treat and manage diseases and disorders affecting the muscles of the neck and/or pharynx.

BACKGROUND

A wide range of neurological diseases and disorders exist that are not well addressed by present medical technology. Among these, dysphagia (a swallowing disorder that affects the central nervous system thereby weakening neuromuscular control and effectively reducing the ability to properly swallow) is a particularly life threatening disorder placing persons at risk of aspiration pneumonia. Patients at risk of aspiration pneumonia have a 17% survival rate over three years. Estimates are that over 7 million persons in the United States have dysphagia as a result of neurological diseases or disorders such as stroke, traumatic brain injury, brain tumors, Parkinson's disease, multiple sclerosis, and other neurological diseases, and over 300,000 persons in the United States develop a swallowing disorder as a result of a neurological disease or disorder each year. Over 50% of patients with neurological diseases or disorders are at risk of aspiration pneumonia because of loss of central nervous system control of their swallowing resulting in either delayed or reduced elevation of the hyolaryngeal complex, which does not allow them to prevent food or liquid from entering the airway. Normally the hyoid and larynx are raised by about 20 millimeters (mm) during swallowing, producing an inversion of the epiglottis and assisting with opening of the upper esophageal sphincter.

Patients having dysphagia often need 24-hour attention to inhibit aspiration and ensure that the passage of food and/or fluids, particularly saliva, into the respiratory system is minimized. Glass rod pressure stimulation to the faucial pillars in the mouth can trigger swallowing, while chemical blocks of laryngeal sensation can severely impair volitional swallowing in normal adults. Pharyngeal stimulation can initiate laryngeal closure and elevation for swallowing in animals, while laryngeal stimulation will trigger a swallow. In humans, sensory stimulation of the oropharynx presented during a period separate from swallowing can enhance cortical activity in the swallowing regions, but does not benefit subsequent swallowing in dysphagic patients. Such approaches to stimulation generally involve the placement of a device or probe into the oral cavity, which interferes with eating food and liquids and can alter oral sensory function in patients already having oral sensory deficits.

SUMMARY

Various stimulations methods have been successful at inducing swallowing and/or speech in subjects, for example, vibrotactile stimulation using one or more vibrational transducers each operating between about 30 Hz and about 60 Hz. The use of multiple vibrational transducers at the same frequency may provide one or more benefits such vibrating each side of the thyroid cartilage to support penetration of the vibration into the vocal folds on each of the right and left sides of the larynx. The use of multiple vibrational transducers at different vibrating properties may provide increased subject response. Different vibrating properties may include vibrating frequency, vibrating frequency range, wave shape, vibrating continuousness, frequency phase, and direction of mechanical force. For example, a subject wearing a device including a first vibrotactile stimulator having a first frequency and a second vibrotactile stimulator having a second frequency different than the first frequency may experience greater increase in induced swallowing compared to one or more vibrotactile stimulators having a single frequency. A higher success rate can reduce learning duration, increase use desirability, and produce more favorable outcomes. Different vibrating properties can also reduce a subject's ability to adapt to a single frequency.

In some embodiments, a method for stimulating swallowing in a subject comprises applying a first vibrotactile stimulation to a throat area of the subject and applying a second vibrotactile stimulation to the throat area of the subject. The first vibrotactile stimulation is at a first vibrating rate. The second vibrotactile stimulation is at a second vibrating rate different than the first vibrating rate. Applying the first vibrotactile stimulation and applying the second vibrotactile stimulation may include the subject voluntary activating vibrotactile stimulators. Applying the first vibrotactile stimulation and applying the second vibrotactile stimulation may include automatically activating the vibrotactile stimulators. Applying the first vibrotactile stimulation may be at least partially simultaneous with applying the second vibrotactile stimulation. The first vibrating rate may be between about 50 Hz and about 90 Hz and the second vibrating rate may be between about 90 Hz and about 130 Hz. The first vibrating rate may be between about 30 Hz and about 60 Hz and the second vibrating rate may be between about 60 Hz and about 90 Hz. The first vibrating rate may be between about 20 Hz and about 40 Hz and the second vibrating rate may be between about 60 Hz and about 80 Hz. The first vibrating rate may be about 30 Hz and the second vibrating rate may be about 70 Hz. The first vibrating rate may be about 70 Hz and the second vibrating rate may be about 110 Hz. The first vibrating rate may be between about 20 Hz and about 60 Hz different than the second vibrating rate. The first vibrating rate may be about 40 Hz different than the second vibrating rate.

In some embodiments, a device comprises a first vibrotactile stimulator, a second vibrotactile stimulator, and a collar. The first vibrotactile stimulator is configured to operate at a first vibrating rate. The second vibrotactile stimulator is configured to operate at a second vibrating rate different than the first vibrating rate. The collar is configured to position the first vibrotactile stimulator and the second vibrotactile stimulator over a neck of a subject. The device may further comprise a switch configured to activate the first vibrotactile stimulator and the second vibrotactile stimulator. The switch may be configured to be volitionally operated by the subject. The device may further comprise an automatic clock configured to activate the first vibrotactile stimulator and the second vibrotactile stimulator. The first vibrotactile stimulator and the second vibrotactile stimulator may be configured to operate at partially simultaneously. The first vibrating rate may be between about 50 Hz and about 90 Hz and the second vibrating rate may be between about 90 Hz and about 130 Hz. The first vibrating rate may be between about 30 Hz and about 60 Hz and the second vibrating rate may be between about 60 Hz and about 90 Hz. The first vibrating rate may be about 30 Hz and the second vibrating rate may be about 70 Hz. The first vibrating rate may be about 70 Hz and the second vibrating rate may be about 110 Hz. The first vibrating rate may be between about 20 Hz and about 60 Hz different than the second vibrating rate. The first vibrating rate may be about 40 Hz different than the second vibrating rate.

In some embodiments, a method for stimulating swallowing in a subject comprises applying a first vibrotactile stimulation to a throat area of the subject, applying a second vibrotactile stimulation to the throat area of the subject. The first vibrotactile stimulation has a first vibrating property. The second vibrotactile stimulation has a second vibrating property different than the first vibrating property.

Applying the first vibrotactile stimulation and applying the second vibrotactile stimulation may include the subject voluntary activating a first vibrational transducer and a second vibrational transducer. Applying the first vibrotactile stimulation and applying the second vibrotactile stimulation may include automatically activating a first vibrational transducer and a second vibrational transducer. Automatically activating the first vibrational transducer and the second vibrational transducer may include coordinating automatically activating the first vibrational transducer and the second vibrational transducer with a monitored bodily parameter. Applying the first vibrotactile stimulation may be at least partially simultaneous with applying the second vibrotactile stimulation. The first vibrating property may comprise a first vibrating frequency and the second vibrating property may comprise a second vibrating frequency different than the first vibrating frequency. The first vibrating rate may be between about 30 Hz and about 60 Hz and the second vibrating rate may be between about 60 Hz and about 80 Hz. The first vibrating rate may be between about 50 Hz and about 90 Hz and the second vibrating rate may be between about 90 Hz and about 130 Hz. The first vibrating rate may be about 30 Hz and the second vibrating rate may be about 70 Hz. The first vibrating rate may be about 70 Hz and the second vibrating rate may be about 110 Hz. The first vibrating property may comprise a first vibrating frequency range and the second vibrating property may comprise a second vibrating frequency range different than the first vibrating frequency range. The first vibrating rate range may be between about 30 Hz and about 60 Hz and the second vibrating rate range may be between about 60 Hz and about 80 Hz. The first vibrating rate range may be between about 50 Hz and about 90 Hz and the second vibrating rate range may be between about 90 Hz and about 130 Hz. The first vibrating property may comprise a first wave shape and the second vibrating property may comprise a second wave shape different than the first wave shape. The first wave shape may comprise sinusoidal and the second wave shape may comprise saw-tooth. The first wave shape may comprise sinusoidal and the second wave shape may comprise triangular. The first wave shape may comprise sinusoidal and the second wave shape may comprise square. The first wave shape may comprise saw-tooth and the second wave shape may comprise triangular. The first wave shape may comprise saw-tooth and the second wave shape may comprise square. The first wave shape may comprise triangular and the second wave shape may comprise square. The first vibrating property may comprise a first vibrating frequency and the second vibrating property may comprise a second vibrating frequency out of phase with the first vibrating frequency. The first vibrating frequency and the second vibrating frequency may be between about 150° and about 210° out of phase. The first vibrating frequency and the second vibrating frequency may be about 180° out of phase. The first vibrating property may comprise a continuous vibrating frequency and the second vibrating property may comprise a pulsed vibrating frequency. The first vibrating property may comprise a first direction of mechanical force and the second vibrating property may comprise a second direction of mechanical force different than the first direction of mechanical force. One of the first direction of mechanical force and the second direction of mechanical force may be substantially perpendicular. One of the first direction of mechanical force and the second direction of mechanical force may be non-perpendicular and non-parallel.

In some embodiments, a device comprises a first vibrational transducer and a second vibrational transducer. The first vibrational transducer has a first vibrating property. The second vibrational transducer has a second vibrating property different than the first vibrating property.

In some embodiments, a device comprises a first vibrational transducer, a second vibrational transducer, and a collar. The first vibrational transducer has a first vibrating property. The second vibrational transducer has a second vibrating property different than the first vibrating property. The collar is configured to position the first vibrational transducer and the second vibrational transducer over a neck of a subject.

The device may further comprise a switch configured to activate the first vibrational transducer and the second vibrational transducer, the switch configured to be volitionally operated by the subject. The device may further comprise an automatic clock configured to activate the first vibrational transducer and the second vibrational transducer. The first vibrational transducer and the second vibrational transducer are configured to operate at partially simultaneously. The first vibrating property may comprise a first vibrating frequency and the second vibrating property may comprise a second vibrating frequency different than the first vibrating frequency. The first vibrating rate may be between about 30 Hz and about 60 Hz and the second vibrating rate may be between about 60 Hz and about 80 Hz. The first vibrating rate may be between about 50 Hz and about 90 Hz and the second vibrating rate may be between about 90 Hz and about 130 Hz. The first vibrating rate may be about 30 Hz and the second vibrating rate may be about 70 Hz. The first vibrating rate may be about 70 Hz and the second vibrating rate may be about 110 Hz. The first vibrating property may comprise a first vibrating frequency range and the second vibrating property may comprise a second vibrating frequency range different than the first vibrating frequency range. The first vibrating rate range may be between about 30 Hz and about 60 Hz and the second vibrating rate range may be between about 60 Hz and about 80 Hz. The first vibrating rate range may be between about 50 Hz and about 90 Hz and the second vibrating rate range may be between about 90 Hz and about 130 Hz. The first vibrating property may comprise a first wave shape and the second vibrating property may comprise a second wave shape different than the first wave shape. The first wave shape may comprise sinusoidal and the second wave shape may comprise saw-tooth. The first wave shape may comprise sinusoidal and the second wave shape may comprise triangular. The first wave shape may comprise sinusoidal and the second wave shape may comprise square. The first wave shape may comprise saw-tooth and the second wave shape may comprise triangular. The first wave shape may comprise saw-tooth and the second wave shape may comprise square. The first wave shape may comprise triangular and the second wave shape may comprise square. The first vibrating property may comprise a first vibrating frequency and the second vibrating property may comprise a second vibrating frequency out of phase with the first vibrating frequency. The first vibrating frequency and the second vibrating frequency may be between about 150° and about 210° out of phase. The device of Embodiment 55, wherein the first vibrating frequency and the second vibrating frequency may be about 180° out of phase. The first vibrating property may comprise a continuous vibrating frequency and the second vibrating property may comprise a pulsed vibrating frequency. The first vibrating property may comprise a first direction of mechanical force and the second vibrating property may comprise a second direction of mechanical force different than the first direction of mechanical force. One of the first direction of mechanical force and the second direction of mechanical force may be substantially perpendicular. One of the first direction of mechanical force and the second direction of mechanical force may be non-perpendicular and non-parallel.

Certain devices and methods disclosed herein can treat a subject with dysphagia or other neurological disease, neurological disorder, neurological injury, neurological impairment, or neurodegenerative disease that affects voluntary motor control of the hyoid, pharynx, larynx, and/or oropharyngeal area. Certain devices and methods disclosed herein can be used to treat a subject with a speech disorder.

In some embodiments, a device comprises a stimulator for applying at least one stimulus to an outside surface of the neck of a subject. The at least one stimulus can comprise a vibrational stimulus, a pressure stimulus, an optical stimulus, an ultrasound stimulus, an auditory stimulus, a temperature stimulus, a visual stimulus, an olfactory stimulus, a gustatory stimulus, and/or combinations thereof. The stimulator may comprise a vibrational transducer. A manual stimulation module may be configured to manually engage the vibrational transducer. An automatic stimulation module may be configured to automatically engage the vibrational transducer. A manual counter and/or an automatic counter may determine the number of times the manual stimulation module and/or the automatic stimulation module are engaged.

In some embodiments, the vibrational transducer produces a wave having a frequency between about 50 Hz and about 70 Hz. In some embodiments, the vibrational transducer produces a wave having a frequency of about 59 Hz. In some embodiments, the automatic stimulation module comprises an automatic timer. The automatic timer can include an automatic clock configured to initiate onset of the automatic stimulation module. An adjustable clock may be configured to initiate the automatic stimulation module at an adjustable interval of about 0.5 seconds (s) to about 30 minutes (min). An adjustable timer may be configured to set a duration of stimulation between about 100 milliseconds (ms) and about 10 s.

In some embodiments, a device comprises a connector for attaching the stimulator to an outside surface of the neck of the subject. The connector can be adjusted by an adjustment mechanism for positioning a contact section of the stimulator substantially over the larynx of the subject. In some embodiments, a device comprises a switch control communicatively connected to the stimulator to selectively engage the manual stimulation module and the automatic stimulation module.

In some embodiments, a device comprises a physiological sensor electrically coupled to the stimulator. The physiological sensor can include breathing sensor, a movement sensor, a temperature sensor, a skin color sensor, a hematocrit sensor, an oxygenation sensor, a blood pressure sensor, a heart rate sensor, combinations thereof, and the like. In some embodiments, the device comprises a swallowing receptor comprising a piezoelectric stretch receptor. For example, the swallowing receptor may comprise an accelerometric movement sensor (e.g., MEMS, piezoelectric). In some embodiments, the device comprises a battery configured to supply power to components of the device. In some embodiments, the device comprises a control box configured to select one or more of the stimulus modes, stimulus types, stimulus shapes, stimulus rates, stimulus continuousness, and stimulus amplitudes.

In some embodiments, a device comprises a digital clock generator, a digital decade counter, and a vibrational transducer (e.g., a motor, a hydraulic system, a pneumatic system, piezoelectric, rainbow (reduced and internally biased oxide wafer), combinations thereof, and the like). The digital clock generator is configured to produce an initial clock signal having a first frequency range. The digital decade counter is configured to receive the initial clock signal and to produce sequential pulses having a second frequency range. The vibrational transducer is responsive to the sequential pulses by producing vibrations on the larynx of the subject. The vibrations are at a third frequency range. In some embodiments, the initial clock signal is adjustable and comprises a frequency. In some embodiments, the frequency of the clock signal comprises about one signal every 3 minutes to about one signal every 30 minutes. In some embodiments, the second frequency range is between about 1 Hertz (Hz) and about 10 Hz, between about 20 Hz and about 75 Hz, or between about 30 Hz and about 60 Hz, with durations between about 10 ms and 500 ms. In some embodiments, the third frequency range is between about 15 and about 200 Hz, or between about 20 and about 100 Hz. The motor can include a gearbox (e.g., planetary, spur). In some embodiments, the vibrational transducer is configured to produce a vibrational frequency between about 50 Hz and about 70 Hz.

In some embodiments, a method comprises treating a subject with dysphagia or another neurological disease, neurological disorder, neurological injury, neurological impairment, or neurodegenerative disease that affects voluntary motor control of the hyoid, pharynx, larynx, oropharyngeal area, or hyolaryngeal complex disorder comprise with a device. The method can be used to treat a subject with a speech disorder.

In some embodiments, a method for inducing a swallowing reflex in a subject can reduce drooling and/or aspiration of secretions of the subject. The secretions can be saliva and/or mucus. The method generally comprises applying a device to an outside surface of the neck of the subject substantially over the larynx of the subject and configuring an automatic timer to activate a vibrotactile stimulator to induce a swallowing reflex. In some embodiments, the automatic timer is configured to activate the vibrotactile stimulator at an interval of about once every 3 minutes to about once every 30 minutes. In some embodiments, activation of the vibrotactile stimulator produces vibrations at a frequency between about 40 Hz and about 70 Hz and applies pressure between about 1 psi and about 14 psi to the neck of the subject during an onset period. In some embodiments, the onset period comprises about 10 ms to about 1.5 s, about 50 ms to about 750 ms, or about 100 ms to about 500 ms.

In some embodiments, a method for identifying a subject at risk of aspiration from their own secretions comprises applying a device to the neck of the subject substantially over the larynx of the subject, downloading data from the device after a period of use, and analyzing the data to determine if the subject is at risk of aspiration from their own secretions. The subject may activate the device to induce volitional swallowing, and the device records the data to allow a health professional to determine if the subject is at risk.

In some embodiments, a method for monitoring subject compliance with a training or therapy regime comprises applying a device to a neck of the subject substantially over the larynx of the subject, downloading data from the device after a period of use, and analyzing the data to determine the subject's compliance with the training or therapy regime. The subject may activate the device to induce volitional swallowing.

For purposes of summarizing the invention and the advantages achieved over the prior art, certain objects and advantages are described herein. Of course, it is to be understood that not necessarily all such objects or advantages need to be achieved in accordance with any particular embodiment. Thus, for example, the invention may be embodied or carried out in a manner that can achieve or optimize one advantage or a group of advantages without necessarily achieving other objects or advantages.

All of these embodiments are intended to be within the scope of the invention herein disclosed. These and other embodiments will become readily apparent from the following detailed description having reference to the attached figures, the invention not being limited to any particular disclosed embodiment(s).

BRIEF DESCRIPTION OF THE DRAWINGS

These and other features, aspects, and advantages of the present disclosure are described with reference to the drawings of certain embodiments, which are intended to illustrate certain embodiments and not to limit the invention.

DETAILED DESCRIPTION

Figure 1A:
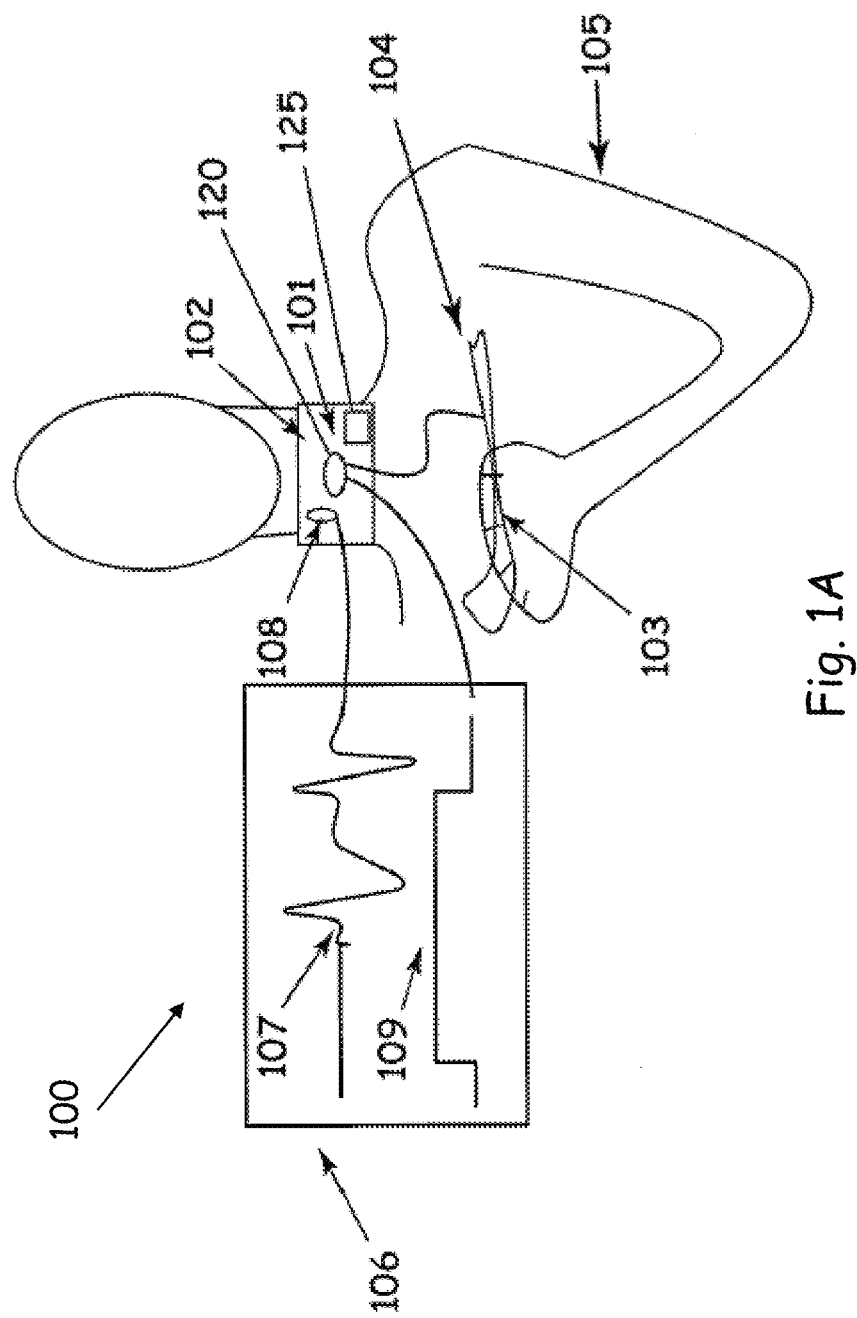
FIG. 1A schematically illustrates an example embodiment of a system incorporating a device for use in volitional swallowing retraining.

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

The present disclosure relates generally to systems and methods for treating and managing neurological disease co-morbidities and disorders affecting the volitional control of muscles that are involved in raising and lowering the hyoid/larynx and/or pharynx in the neck. Systems and methods that can produce deglutition stimulation and vocalization stimulation and/or combinations thereof are disclosed. The stimulation may be volitionally controlled, automatically controlled, and controlled electrically, mechanically, chemically, or biologically. For example, vibrotactile and/or pressure stimulation on the neck region of the larynx may elicit swallowing. Vibrotactile stimulation at two different vibrating rates may be particularly effective at eliciting a swallowing reflex. Certain such methods and systems may be particularly useful for treating and managing subjects having dysphagia and/or dysphonia.

Others have attempted providing stimulation to areas that are reduced in sensory function to enhance swallowing in subjects with dysphagia. For example, a dental plate may be constructed and placed over the lower teeth, but this device interferes with mouth closing and makes it difficult for subjects to control liquid in their mouth. For another example, electrical stimulation of the faucial pillars in the mouth via a probe placed in the mouth interferes with mouth closing and makes it difficult for subjects to swallow such that this technique can only be used at a time separate from asking the subject to swallow. Placement of devices into the oral cavity is not optimal, as such devices can interfere with eating food and liquids and alter the oral sensory function in subjects who already have oropharyngeal sensory deficits. In some embodiments, the devices described herein may be applied to an exterior surface of the throat area, and not inside the mouth or the pharynx.

Many subjects with dysphagia already have oral sensory deficits. Providing stimulation to regions that are already impaired in sensation can be expected to provide less sensory facilitation of volitional and reflexive swallowing than sensory stimulation to unaffected areas. Therefore, certain systems and methods described herein can facilitate sensory stimulation to areas unaffected by sensory deficits such as the skin overlying the throat area and the vibratory sensors in the musculature and cartilages in the throat area and the thyroid cartilage. Vibratory stimulation of the thyroid cartilage and the sternothyroid muscle can also affect voice. Some methods and systems described herein differ from some previous approaches in that the subject can initiate the stimulation immediately prior to attempting to swallow, and such stimulation is applied to an area that does not interfere with oral and pharyngeal movement and sensation during swallowing.

A. Stimulator Systems and Devices

FIG. 1A schematically illustrates an example embodiment of a system 100 incorporating a device for use in volitional retraining, for example for treating dysphagia or a speech disorder. The system 100 comprises a band 101 and a stimulator 102 coupled to the band 101. The band 101 may be wrapped around the neck of the subject 105 during treatment. The band 101 may comprise a stretchable fabric such as a wrap including hook-and-loop fastener material, and may be adjustable for individual subjects' bodies. The stimulator 102 may include a vibrotactile stimulator 102 configured to be positioned over the larynx of the subject 105 to provide sensory stimulation. In certain embodiments, a designated contact section 120 of the vibrotactile stimulator 102 is positioned to be in contact with the outside of the throat over the larynx. The band 101 can include an adjustment mechanism 125 for tailorable positioning of the contact section 120 over the larynx of the subject 105. Vibrotactile and electrical stimulators are preferably positioned close to the skin.

The system 100 further comprises an actuator 103 in communication with the stimulator 102. The actuator 103 may be physically wired to the stimulator 102 or in wireless communication with the stimulator 102. The actuator 103 may be a button, switch, or the like. The actuator 103 can be covered when not in use. In some embodiments, the actuator 103 comprises a button in a small cover that may be reversibly slid over the top of the handle of a utensil 104 (e.g., a spoon, fork, or knife held by the subject 105) or utensil handle-shaped mount. In some embodiments, the actuator 103 is independent of any utensil. Upon activation of the actuator 103, the stimulator 102 transmits vibrational energy to the throat and the larynx of the subject 105.

In certain embodiments, the system 100 includes a device configured to control operation of one or more stimulators 102. For example, such a can comprise a control box (not shown) having appropriate switches, knobs, dials, etc. that can be adjusted to set a stimulus type, a stimulus shape (e.g., a wave shape (e.g., sinusoidal, sawtooth, square wave)), a stimulus continuousness (e.g., continuous, pulsed) a stimulus rate (constant or changing over time), a stimulation continuousness (e.g., continuous, pulsed), and/or a stimulus amplitude (constant or changing over time). The control box can include features to determine stimulus duration. For example, the control box can be configured to allow for stimulation for a specific duration upon activation of the actuator 103 or as long as actuator 103 is activated (e.g., as long as a button is pushed). In some embodiments, the duration of stimulation is between about 6 seconds and about 25 seconds.

Still referring to FIG. 1A, instructions can be provided to the subject 105 for practicing initiating the sensory stimulation (e.g., by activating the actuator 103) immediately prior to an attempted initiation of a motor act such as swallowing or speaking. In some embodiments, the band 101 comprises, or the device 100 is in communication with, a sensor 108 such as an accelerometric movement sensor (e.g., MEMS, piezoelectric) and/or pressure sensor that can provide a movement feedback signal 107 that can be displayed on a screen 106 to help coordinate the initiation. The movement feedback signal 107 can be displayed on the display screen 106 constantly or when movement. The signal 109 from the button 103, initiating sensory stimulation, can be presented on the same display screen 106 for the subject 105 and/or a trainer to observe when the actuator 103 was activated for sensory stimulation in relation to the onset of the motor act. In this manner, the subject 105 can learn to optimize the timing of activating the stimulator 102 about 200 ms to about 600 ms prior to the onset of their motor act. Communication between the sensor 108 and the display 106 and/or between the button 103 and the display 106 may be wired or wireless. A vibrational transducer vibrating frequency of about 30 Hz to about 60 Hz may be particularly effective in eliciting the swallowing reflex.

The stimulator 102 may comprise, for example, a low voltage DC motor with a gearbox (e.g., planetary, spur) utilized to generate a particular frequency. Other types of vibrational transducers are also possible. In operation, the gearbox can reduce the output rotation per minute (RPM) to the desired range and increase the available torque. An eccentrically loaded mass may be attached to the output shaft to generate the vibration. The mass weight can be changed to increase or decrease the vibration amplitude. In some embodiments, a lightweight, sealed aluminum tube encapsulates the motor assembly. In certain embodiments, the vibrator motor utilizes a sleeve shaft for the output shaft. In certain embodiments, the vibrator motor utilizes a sleeve bearing for the output shaft. In certain embodiments, the vibrator motor utilizes a ball bearing for the output shaft.

Figure 1B:
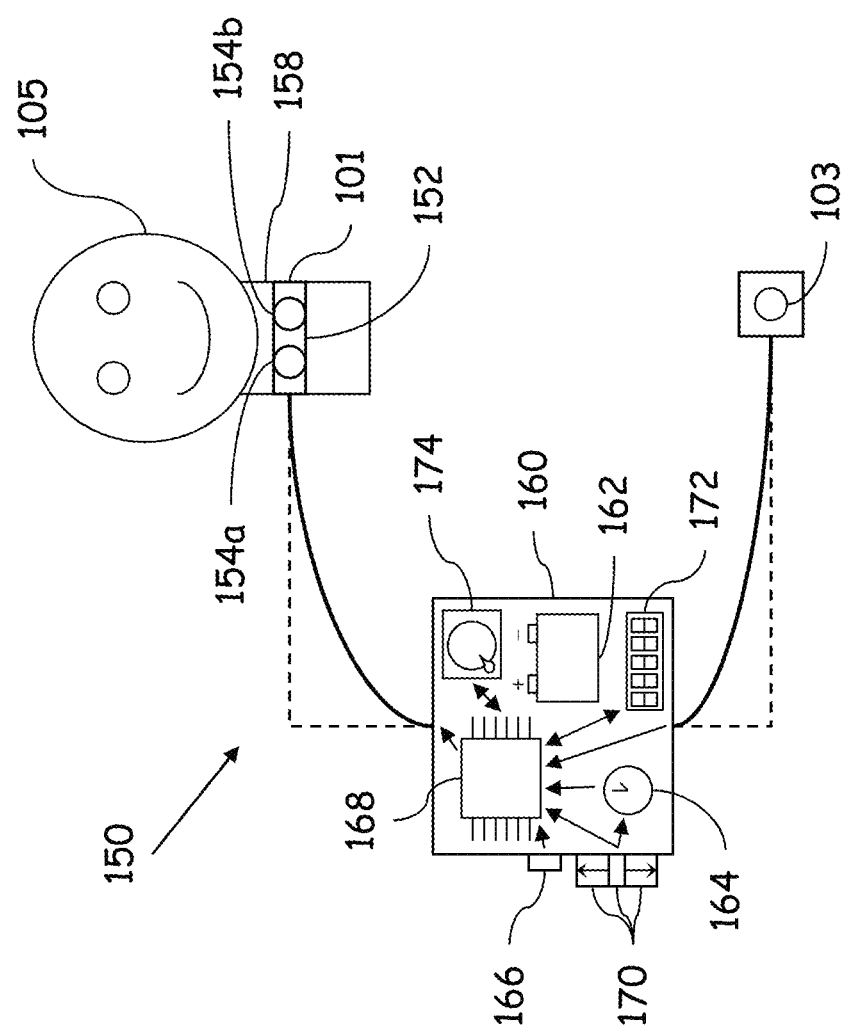
FIG. 1B schematically illustrates an example embodiment of a system for treating neurological disorders.

FIG. 1B schematically illustrates an example embodiment of a system 150 for treating neurological disorders such as dysphagia and dysphonia. Certain features that may be similar to the features of the system 100 utilize the same reference number and may share at least some of the same characteristics as the features thereof (e.g., the collar 101, the actuator 103, etc.).

The system 150 includes a stimulator device 152 comprising a first vibrational transducer 154a, a second vibrational transducer 154b, and a collar 101. The vibrational transducers 154a, 154b may include, for example, a vibrotactile stimulator, a motor, a hydraulic system, a pneumatic system, piezoelectric, rainbow, combinations thereof, and the like. The first vibrational transducer 154a has a first vibrating property. The second vibrational transducer has a second vibrating property different than the first vibrating property. For clarity, a vibrating property is not necessarily different merely because a different vibrational transducer is used (e.g., slight differences in frequency due to a range of mechanical error, slight differences in direction of mechanical force due to a range of installation error, etc. would not be considered to be different vibrating properties).

In some embodiments, the vibrating property includes vibrating rate or frequency phase. For example, the first vibrational transducer 154a is configured to operate at a first vibrating rate and the second vibrational transducer 154b is configured to operate at a second vibrating rate similar to or the same as the first vibrating rate, but the phase of vibration is offset. For example, the first vibrating rate and the second vibrating rate may be between about 150° and about 210° out of phase (e.g., about 180° out of phase or polarity shifted). In certain such embodiments, the first vibrational transducer 154a may be pulling while the second vibrational transducer 154b is pushing, and vice versa. Other phase differences are also possible. For example, phase differences between 0° and 180° or between 180° and 360° may create a chasing-type effect.

In some embodiments, the vibrating property includes vibrating rate or frequency. The first vibrational transducer 154a is configured to operate at a first vibrating rate and the second vibrational transducer 154b is configured to operate at a second vibrating rate different than the first vibrating rate. In some embodiments, the first vibrating rate is between about 50 Hz and about 90 Hz (e.g., about 70 Hz) and the second vibrating rate is between about 90 Hz and about 130 Hz (e.g., about 110 Hz). In some embodiments, the first vibrating rate is between about 30 Hz and about 60 Hz (e.g., about 30 Hz) and the second vibrating rate is between about 60 Hz and about 90 Hz (e.g., about 70 Hz). In some embodiments, the first vibrating rate is between about 20 Hz and about 60 Hz (e.g., about 40 Hz) different than the second vibrating rate. Other example vibrating rates and differences are described further herein.

In some embodiments, the first vibrating rate is between about 10 Hz and about 40 Hz (e.g., about 25 Hz) different than the second vibrating rate. In some embodiments, the first vibrating rate is between about 10 Hz and about 200 Hz, between about 20 Hz and about 150 Hz, or between about 30 Hz and about 100 Hz different than the second vibrating rate. Larger differences between vibrating rates may provide a broader range of stimulus. Smaller differences between vibrating rates may provide more concentrated stimulus at known useful frequencies and/or provide more overlap, as described herein.

In some embodiments, the first vibrating rate and the second vibrating rate are harmonic. For example, the first vibrating rate may be about 30 Hz and the second vibrating rate may be about 60 Hz, about 90 Hz, about 120 Hz, about 150 Hz, etc. For example, the first vibrating rate may be about 50 Hz and the second vibrating rate may be about 100 Hz, about 150 Hz, etc. For example, the first vibrating rate may be about 50 Hz and the second vibrating rate may be about 75 Hz, about 100 Hz, about 125 Hz, about 150 Hz etc. (e.g., when the first vibrating rate is not the fundamental frequency). In some embodiments, the first vibrating rate and the second vibrating rate are non-harmonic.

The differences in the vibrating rates may mimic and/or enhance the effects of two vibrating rates that are the same but with offset phases. For example, during some periods, the first vibrational transducer 154a may be pulling while the second vibrational transducer 154b is also pulling, increasing the pulling effect of either vibrational transducer 154a, 154b alone, and the first vibrational transducer 154a may be pulling while the second vibrational transducer 154b is pushing, and vice versa.

A frequency between the first vibrating rate and the second vibrating rate may produce a third or beat frequency. For example, if the first vibrating rate is about 30 Hz and the second vibrating rate is about 70 Hz, a beat frequency would be about 50 Hz. For example, if the first vibrating rate is about 70 Hz and the second vibrating rate is about 110 Hz, a beat frequency would be about 90 Hz. In some embodiments, the beat frequency is between about 30 Hz and about 120 Hz, between about 40 Hz and about 60 Hz, or between about 80 Hz and about 100 Hz different than the second vibrating rate. Other beat frequencies are also possible, for example by modifying at least one of the first vibrating rate and the second vibrating rate.

In some embodiments, the vibrating property includes vibrating rate or frequency range. At least one of the first vibrational transducer 154a and the second vibrational transducer 154b is configured to operate within a vibrating rate range, for example oscillating between the extremes of the vibrating rate range. For example, in some embodiments, the first vibrational transducer 154a is configured to operate at a first vibrating rate range between about 30 Hz and about 90 Hz (e.g., centered around about 60 Hz) and the second vibrational transducer 154b is configured to operate at a single second vibrating rate between about 90 Hz and about 130 Hz (e.g., about 110 Hz). In some embodiments in which one of the vibrational transducers 154a, 154b is configured to operate at a vibrating rate range and the other of the vibrational transducers 154a, 154b is configured to operate at a single vibrating rate, the vibrating rate range may overlap the single vibrating rate. In some embodiments in which one of the vibrational transducers 154a, 154b is configured to operate at a vibrating rate range and the other of the vibrational transducers 154a, 154b is configured to operate at a single vibrating rate, the vibrating rate range may not overlap the single vibrating rate.

For another example, in some embodiments, the first vibrational transducer 154a is configured to operate at a first vibrating rate range between about 30 Hz and about 90 Hz (e.g., centered around about 60 Hz) and the second vibrational transducer 154b is configured to operate at a second vibrating rate range between about 70 Hz and about 130 Hz (e.g., centered around about 100 Hz). In some embodiments in which both vibrational transducers 154a, 154b are configured to operate at a vibrating rate range, the ranges may at least partially overlap. In some embodiments in which both vibrational transducers 154a, 154b are configured to operate at a vibrating rate range, the ranges may not overlap.

In some embodiments in which at least one of the vibrational transducers 154a, 154b is configured to operate at a vibrating rate range, the beat frequency may vary over time. For example, if the first vibrational transducer 154a is configured to operate at a first vibrating rate range between about 30 Hz and about 90 Hz and the second vibrational transducer 154b is configured to operate at a single second vibrating rate of about 110 Hz, the beat frequency may shift between about 70 Hz and about 100 Hz. In some embodiments in which both of the vibrational transducers 154a, 154b are configured to operate at a vibrating rate range, the beat frequency may vary over time. For example, if the first vibrational transducer 154a is configured to operate at a first vibrating rate range between about 30 Hz and about 90 Hz and the second vibrational transducer 154b is configured to operate at a second vibrating rate range between about 90 Hz and about 130 Hz, the beat frequency may shift between about 0 Hz and about 100 Hz. In some embodiments in which both of the vibrational transducers 154a, 154b are configured to operate at a vibrating rate range, the beat frequency may not vary over time. For example, if the first vibrational transducer 154a is configured to operate at a first vibrating rate range between about 30 Hz and about 60 Hz and the second vibrational transducer 154b is configured to operate at a second vibrating rate range between about 60 Hz and about 90 Hz, and the rate of change of frequency is the same, the beat frequency remain at about 30 Hz (e.g., about 30 Hz when the first vibrating rate is about 30 Hz and the second vibrating rate is about 60 Hz, about 30 Hz when the first vibrating rate is about 45 Hz and the second vibrating rate is about 75 Hz, about 30 Hz when the first vibrating rate is about 60 Hz and the second vibrating rate is about 90 Hz).

In some embodiments in which both of the vibrational transducers 154a, 154b are configured to operate at a vibrating rate range, the width of the range may be the same. For example, if the first vibrational transducer 154a may be configured to operate at a first vibrating rate range between about 30 Hz and about 60 Hz, having a width of about 30 Hz, and the second vibrational transducer 154b may configured to operate at a second vibrating rate range between about 70 Hz and about 100 Hz, also having a width of about 30 Hz. In some embodiments in which both of the vibrational transducers 154a, 154b are configured to operate at a vibrating rate range, the width of the range may be the different. For example, if the first vibrational transducer 154a may be configured to operate at a first vibrating rate range between about 30 Hz and about 60 Hz, having a width of about 30 Hz, and the second vibrational transducer 154b may configured to operate at a second vibrating rate range between about 70 Hz and about 110 Hz, having a width of about 40 Hz.

In some embodiments, the vibrating property includes vibrating wave shape. Example wave shapes include sinusoidal, triangular, saw-tooth, square, combinations thereof, and the like. The first vibrational transducer 154a may have a first wave shape and the second vibrational transducer 154b may have a second wave shape different than the first wave shape. For example, the first wave shape can be sinusoidal and the second wave shape can be triangular, the first wave shape can be sinusoidal and the second wave shape can be saw-tooth, the first wave shape can be sinusoidal and the second wave shape can be square, the first wave shape can be triangular and the second wave shape can be saw-tooth, the first wave shape can be triangular and the second wave shape can be square, or the first wave shape can be saw-tooth and the second wave shape can be square.

In some embodiments, the vibrating property includes vibrating continuousness. For example, the first vibrational transducer 154a may be continuous and the second vibrational transducer 154b may be pulsed, or vice versa. Pulsed vibration can produce a ramped or building response and continuous vibration can produce a steady response.

The collar 101 is configured to position the first vibrotactile stimulator 154a and the second vibrotactile stimulator 154b over a neck 158 of a subject 105. The first vibrotactile stimulator 154a and the second vibrotactile stimulator 154b are configured to operate at partially simultaneously. A beat frequency between the vibrating rates may be produced during any duration in which both vibrotactile stimulators 154a, 154b operate. In some embodiments, the first vibrotactile stimulator 154a and the second vibrotactile stimulator 154b are configured to operate substantially the same or the same duration. The durations may be entirely cotemporal, or the durations may at least partially overlap. In some embodiments, the first vibrotactile stimulator 154a is configured to operate for a duration and the second vibrotactile stimulator 154b are configured to operate for a shorter duration, or vice versa. The shorter duration may be entirely during the longer duration, or the shorter duration may at least partially overlap the longer duration. During periods of operation of both vibrotactile stimulators 154a, 154b, the input to the mechanoreceptors continually varies.

In some embodiments, the vibrating property includes direction of mechanical force. In some embodiments, the collar 101 and/or the design of the vibrotactile stimulators 154a, 154b can enable the direction of mechanical force produced by the vibrotactile stimulators 154a, 154b to be different. For example, the direction of mechanical force produced by the first vibrotactile stimulator 154a may be substantially perpendicular or perpendicular to the subject's skin under the first vibrotactile stimulator 154a and the direction of mechanical force produced by the second vibrotactile stimulator 154b may at a non-perpendicular and non-parallel angle (e.g., greater than 0° and less than 90°) to the subject's skin under the second vibrotactile stimulator 154b. For example, the direction of mechanical force produced by the first vibrotactile stimulators 154a may be at a first non-perpendicular and non-parallel angle (e.g., greater than 0° and less than 90°) to the subject's skin under the first vibrotactile stimulator 154a and the direction of mechanical force produced by the second vibrotactile stimulator 154b may at a second non-perpendicular and non-parallel angle (e.g., greater than 0° and less than 90°) to the subject's skin under the second vibrotactile stimulator 154b different than the first non-perpendicular and non-parallel angle.

The illustrated system 150 includes a control box 160 including a schematic depiction of a number of optional features. It will be appreciated that some features from the control box 160 may be integrated with the stimulator device 152 and/or the actuator 103. The control box 160 may be in wired communication (e.g., as shown by the heavy curved lines) or wireless communication (e.g., as shown by the dashed cornered line) with the stimulator device 152 and/or the actuator 103. The actuator 103 may thereby be in wired and/or wireless communication with the stimulator device 152. In some embodiments, some or all of the components of the control box 160 may be integrated with the stimulator device 152, although size and weight considerations may be considered. In some embodiments, some or all of the components of the control box 160 may be integrated with the actuator 103, although considerations may include water resistance and durability.

Although certain embodiments and examples of vibrating properties are described herein in detail, various combinations, sub-combinations, modifications, variations, substitutions, and omissions of vibrating properties are possible, some of which will now be described for example purposes only. The first vibrotactile stimulator 154*a* may be configured to operate at a first vibrating rate and to have a first direction of mechanical force and the second vibrotactile stimulator 154*b* may be configured to operate at a second vibrating rate different than the first vibrating rate and to have a second direction of mechanical force different than the first direction of mechanical force. The first vibrotactile stimulator 154*a* may be configured to operate at a first vibrating rate and a first wave shape and the second vibrotactile stimulator 154*b* may be configured to operate at a second vibrating rate different than the first vibrating rate and a second wave shape different than the first wave shape. These are two such examples of combinations of at least two different vibrating properties, but any two or more of the different vibrating properties described herein or other vibrating properties may be combined.

The control box 160 may include a power supply 162 such as a battery, a cord that plugs into a wall or an adapter (e.g., a universal serial bus (USB) adapter). In embodiments in which the control box 160 is in wired communication with the stimulator device 152 and/or the actuator 103, the power supply 162 may provide power to such stimulator device 152 and/or actuator 103. Although not illustrated in FIG. 1B, the stimulator device 152 and/or the actuator 103 may also include a power supply. The control box 160, the stimulator device 152, and/or the actuator 103 may be coupleable (e.g., via induction or wired connection), for example to share a recharging power source.

In some embodiments, the system 150 comprises a switch 103 configured to activate the first vibrotactile stimulator 154*a* and the second vibrotactile stimulator 154*b*. The switch 103 is configured to be volitionally operated by the subject 105, for example immediately prior to a volitional attempt to swallow. In some embodiments, the control box 160 includes an automatic clock 164 configured to activate the first vibrotactile stimulator 154*a* and the second vibrotactile stimulator 154*b*, for example as described in further detail herein. During automatic mode, the actuator 103 may be omitted from the system 150. In some embodiments, the control box 160 includes a mode selector switch 166 for toggling between manual mode and automatic mode, and optionally a system off, although the system may be substantially or intermittently idle during manual mode, for example during periods with no activation of the actuator 103.

The control box 160 includes electrical components 168 described in further detail herein, for example with respect to FIGS. 3-11. The electrical components may include a processor, a voltage regulator, a potentiometer, a transmitter, a receiver, or any appropriate analog and/or digital circuitry. FIG. 1B illustrates the electrical components 168 as being a processor, for example because some processors may replace a wide variety of electrical components. In some embodiments, a processor can perform the functions of the automatic clock 164. In some embodiments, a smart phone or the like may include an application configured to control the stimulator.

The control box 160 may comprise adjustment controls 170. The adjustment controls 164 may allow a user and/or the subject 105 to adjust parameters of the system 150, for example the first vibrating rate of the first vibrotactile stimulator 154*a*, the second vibrating rate of the second vibrotactile stimulator 154*b*, amplitude, duration, delay after activation of the actuator 103, etc. For example, the adjustment controls may be in communication with the electrical components 168 (e.g., a potentiometer) to adjust the vibrating frequency of the vibrotactile stimulators. Parameters and other information may be stored in a system memory 174, which may comprise storage such as flash memory and/or a magnetic drive and/or temporary storage such as random access memory.

In some embodiments, the control box 160 comprises a counter 172, for example to track compliance with a treatment protocol or to identifying a subject at risk of aspiration. A processor 168 and/or memory 174 may take the place of individual counters 172. The adjustment controls 170 may be operated to reset a counter.

In some embodiments, the device 150 comprises a physiological sensor. The physiological sensor can include, for example, a breathing sensor, a movement sensor, a temperature sensor, a skin color sensor, a hematocrit sensor, an oxygenation sensor, a blood pressure sensor, a heart rate sensor, combinations thereof, and the like. In some embodiments, the device can utilize the input from one or more sensors to coordinate (e.g., initiate and/or to delay) stimulation. For example, if a breathing sensor senses that a subject is breathing in, stimulation may be delayed (e.g., until the subject stops breathing in or is breathing out) to reduce the risk of aspiration from swallowing and breathing in at the same time. For example, if a heart rate sensor senses that a subject diastole, stimulation may be delayed until the subject is systole, or vice versa. Stimulation coordination may be useful, for example when the device 150 is in automatic mode, for example when the subject has little or no control over when the elicitation of swallowing may occur.

Without wishing to be bound by any one theory, it is believed that such motor training can produce concurrent brain activation due to sensory input that induces a central pattern generator in the subject's brain stem that produces the related effect of swallowing. This principle may be applicable to many other neurological impairments, their associated motor act habituations, and related sensory stimulations. Accordingly, the scope of the methods and systems disclosed herein may be applicable to a large variety of subjects having various diseases and disorders.

Figure 2:
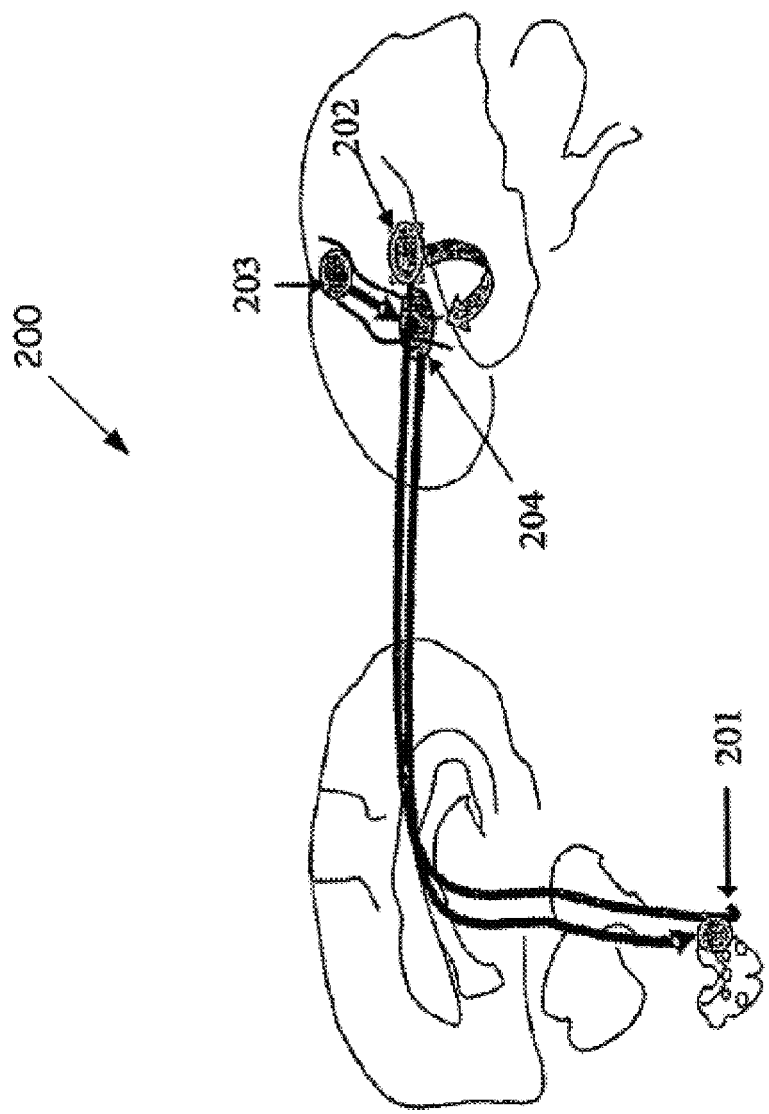
FIG. 2 is an example diagram illustrating the neural circuitry involved in the concurrent use of hand control and substitute sensory stimulation to enhance volitional swallowing.

FIG. 2 is an example diagram 200 illustrating the neural circuitry involved in the concurrent use of hand control and substitute sensory stimulation to enhance volitional swallowing. More specifically, FIG. 2 illustrates the neural circuitry in using a hand control 203 to trigger volitional swallowing 204 along with simultaneous sensory stimulation 201, which goes to the cortex 202. This sequence occurs after button press training described herein. Elicitation of the swallowing reflex and safety in swallowing may be dependent upon sensory feedback 201 to the brain from sensory mechanoreceptors in the upper airway. If sensory input is withdrawn, subjects may feel that they can no longer swallow and are at significant increase of aspiration during swallowing. The neural circuitry enhances cortical motor control 202 of swallowing coincident with substitution of sensory input 203 from stimulation of the throat area to trigger brain stem circuitry to trigger reflexive swallowing 204 simultaneous with volitional swallowing.

Figure 3:
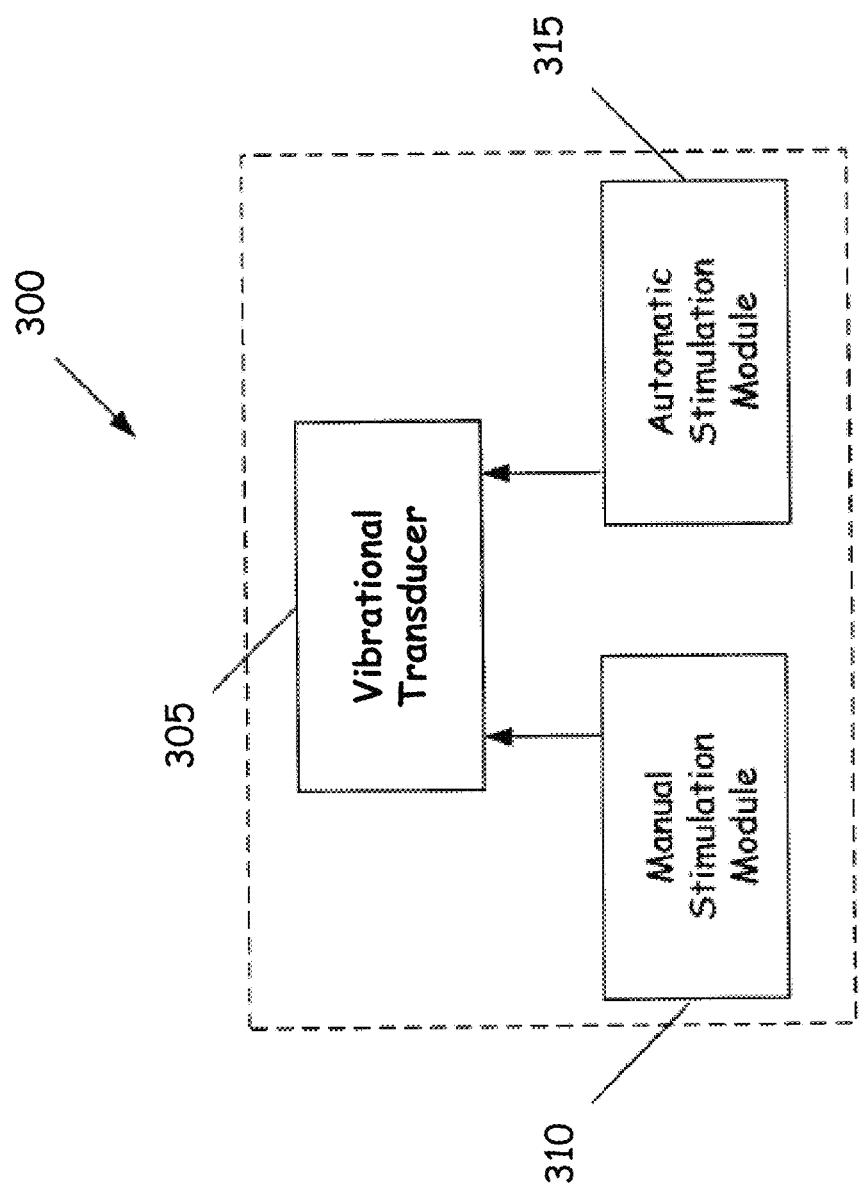
FIG. 3 is a block diagram of an example embodiment of a vibrotactile stimulator.

FIG. 3 is a block diagram of an example embodiment of a vibrotactile stimulator 300. The vibrotactile stimulator 300 can be used in the example system 100. In certain embodiments, the vibrotactile stimulator 300 is pressed against the outside surface of subject's throat to stimulate the larynx such that, with coordination, the vibrotactile stimulator 300 can enhance volitional control of swallowing.

As described herein, the vibrotactile stimulator 300 may be secured or connected to a connector or a band (e.g., the band 101) that can be wrapped around the subject's neck. In this manner, a designated contact section of the vibrotactile stimulator 300 can be positioned on the subject's neck to vibrotactilely stimulate the throat and larynx. The connector can include an adjustment mechanism for a fine adjustment of the contact section over the subject's larynx. In certain embodiments, the adjustment mechanism is configured to shift the position of the vibrotactile stimulator 300 within a circle having an area of about 0.01 $cm^2$ to about 10 $cm^2$, about 0.25 $cm^2$ to about 5 $cm^2$, or about 0.5 $cm^2$ to about 2.5 $cm^2$. In certain embodiments, the adjustment mechanism is configured to vertically shift the position of the vibrotactile stimulator 300 by a distance of about 0.01 cm to about 5 cm, about 0.25 cm to about 2.5 cm, or about 0.5 cm to about 1.5 cm.

In general, the vibrotactile stimulator 300 includes a manual stimulation module 310 operatively configured to allow a user to manually operate the vibrotactile stimulator 300 by activating an external actuator in communication with the vibrotactile stimulator 300. Described at a high level, activating the actuator can transmit energy from engage a vibrational transducer to a subject's larynx. In some embodiments, the actuator is a switch that, when activated, energizes a vibrational transducer 305 that vibrates at a desired frequency a periodic pressure wave that can transmit vibrational energy to the subject's larynx. The vibrational transducer 305 may include, for example, a motor, a hydraulic system, a pneumatic system, piezoelectric, rainbow, combinations thereof, and the like. In some embodiments, the actuator is a switch that, when activated, energizes a first vibrational transducer 305 that vibrates at a first frequency that can transmit vibrational energy to the subject's larynx and energizes a second vibrational transducer 305 that vibrates at a second frequency different than the first vibrating frequency that can transmit vibrational energy to the subject's larynx. In some embodiments, when the ON switch is released, the vibration produced by the vibrational transducer(s) 305 is terminated. In some embodiments, regardless of when the ON switch is released, the vibration produced by the vibrational transducer(s) 305 is terminated after a certain duration. There is substantially no delay between pressing the ON switch and the vibration of the throat area. In use, the manual stimulation module 310 may be engaged during activities such as eating, drinking, and swallowing to inhibit or prevent aspiration with subjects having dysphagia.

The stimulator 300 further comprises an automatic stimulation module 315 operatively configured to automatically energize the vibrational transducer 305. In certain embodiments, the automatic stimulation module 310 enables the subject or caregiver to programmably define vibrational transducer 305 operating parameters such as duration, vibrational frequency, and amplitude. For example, the automatic stimulation module 315 can function to periodically energize the vibrational transducer 305 to induce swallowing throughout the course of a day, thereby reducing saliva aspiration (and in general for saliva control). For another example, the automatic stimulation module 315 can function to periodically energize a first vibrational transducer 305 having a first vibrating frequency and a second vibrational transducer 305 having a second vibrating frequency different than the first vibrating frequency to induce swallowing throughout the course of a day, thereby reducing saliva aspiration (and in general for saliva control). The automatic stimulation mode 315 may be useful for subjects afflicted with dysphagia, for subjects with neurological disorders who have uncontrolled drooling, and for subjects with cerebral palsy who have uncontrolled drooling. In some embodiments, the automatic stimulation module 315 includes an automatic timer circuit configured to facilitate the periodic energizing of the vibrational transducer(s) 305, as described in further detail herein. In some embodiments, the automatic timer can provide continuous practice throughout the day, which may be useful for rehabilitation of speech and/or swallowing disorders. Automatic stimulation occurring at regular intervals of one every 3 minutes to one every 30 minutes can induce regular swallowing to reduce or eliminate drooling.

Components of the vibrotactile stimulator 300 as described in the present disclosure may be implemented via hardware and/or software techniques. For example, the vibrotactile stimulator 300 may include a printed circuit board (PCB). The PCB may comprise a plurality of discrete electrical components such as transistors, capacitors, inductors, resistors, and functional integrated circuitry such as a processor, a memory element, such as read-only memory (ROM) and/or random access memory (RAM), a field programmable logic array (FPGA), and/or input/output circuitry.

Figure 4A:
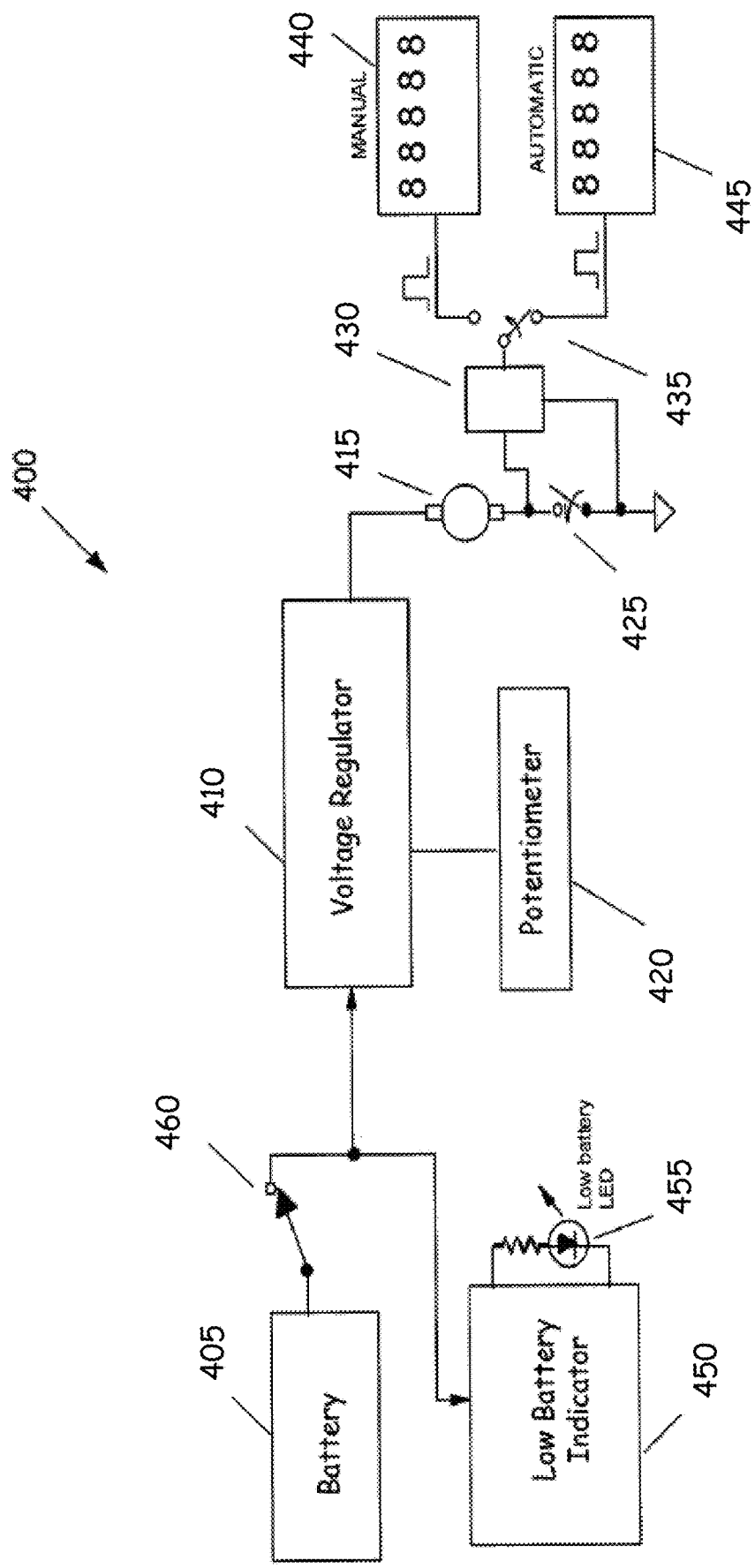
FIGS. 4A-4F are block diagrams of example embodiments of a vibrotactile stimulator.

FIG. 4A is another block diagram of an example embodiment of a vibrotactile stimulator 400. The vibrotactile stimulator 400 is a possible implementation of the vibrotactile stimulator 300 of FIG. 3. In general, upon engagement of a power switch 460, a battery 405 supplies power to a three-terminal voltage regulator 410. In the embodiment illustrated in FIG. 4A, the voltage regulator 410 is used as an adjustable current source to control the vibrational frequency of the vibrational transducer 415. This may be accomplished, for example, by utilizing an external adjustable potentiometer 420.

A switch control 425 enables the subject to voluntarily engage the manual stimulation module 440. In certain embodiments, the switch control 425 is in communication with an external actuator such as a control box or a utensil. In the embodiment illustrated in FIG. 4A, activation of the switch control 425 electrically loads a switch interface 430 such that a count select mechanism 435 is actuated. A manual counter 440 is enabled when the user operates the vibrotactile stimulator 400 in the manual mode, and an automatic counter 445 is engaged when automatic stimulation is employed, as described further below. Engagement of a counter 440, 445 may comprise incrementing the counter. In some embodiments, the automatic stimulation module 315 may be implemented with an automatic timer circuit such that the switch control 425 can be controlled by the automatic timer circuit to actuate the count select mechanism 435, thereby engaging the automatic counter 445 and energizing the vibrational transducer 415.

In the embodiment illustrated in FIG. 4A, the counters 440, 445 are internally mounted to the vibrotactile stimulator 400. The manual counter 440 records the number of times a subject engages the manual stimulation module 310. The automatic counter records the number of times the automatic stimulation module 315 is engaged by the automatic timer circuit. After a period of use by a subject, the counters 440, 445 may be visually and/or electronically interrogated or read (e.g., the value of the counter may be determined by a human or computing device), and manually and/or electronically reset after the total number of counts are recorded. In some embodiments, a wireless data interrogation using one of many technologies (e.g., Bluetooth) may transfer the information to an external application. The quantitative information provided by the counters 440, 445 may provide, for example, an investigator or caregiver quantitative information regarding subject compliance and information regarding the effectiveness of the vibrotactile stimulator 400. As subject compliance is generally low, around 50%, it can be important to the rehabilitation process to identify poor compliance, particularly in the management of dysphagia, a life threatening disorder. Identification of poor compliance allows the therapist to intervene to assure proper use of the device by the subject and their caregivers.

The vibrational transducer 415 may include two different vibrational transducers, for example configured to respond to the same voltage by producing different vibrating frequencies. In certain such embodiments, adjustment of the potentiometer would adjust the voltage, and the frequency, of both vibrational transducers 415 dependently. Lack of independent control of the vibrating frequencies may be an acceptable alternative to some of the more complicated systems described herein, although those complicated systems may advantageously provide independent control of vibrating frequencies.

In certain embodiments, the manual counter 440 and the automatic counter 445 can be coupled to their own power supplies so that cumulative counts are not lost when the power switch 460 is disengaged.

The vibrotactile stimulator 400 optionally includes a low battery indicator 450 such that if the battery 405 voltage drops below a specified voltage level, a "Low Battery" indicator (e.g., light emitting diode (LED)) specifying that event is generated.

Figure 4B:
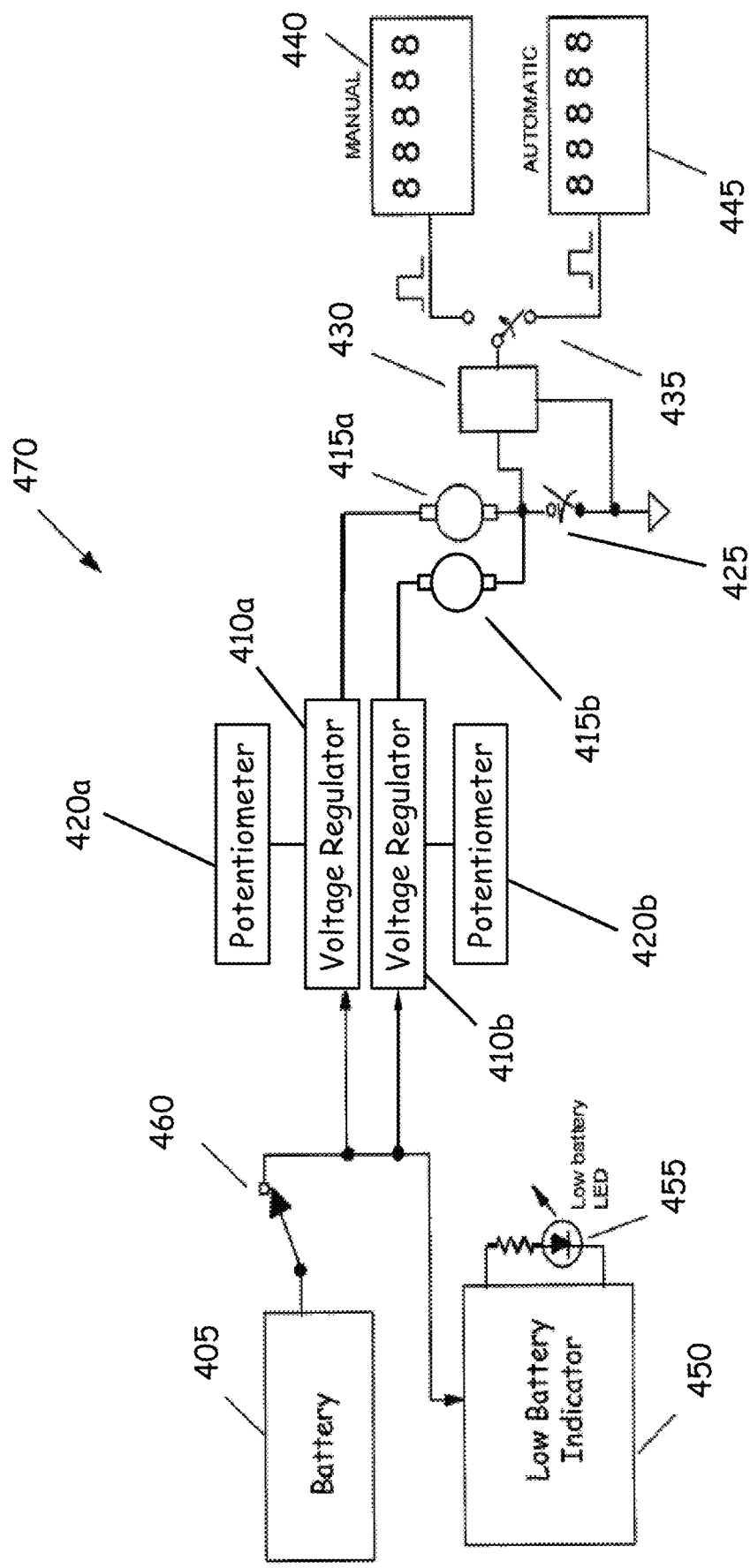

FIG. 4B is yet another block diagram of an example embodiment of a vibrotactile stimulator 470. The vibrotactile stimulator 470 is another possible implementation of the vibrotactile stimulator 300 of FIG. 3. In general, the vibrotactile stimulator 470 may operate similarly to the vibrotactile stimulator 400 in many aspects, although upon engagement of a power switch 460, a battery 405 supplies power to two three-terminal voltage regulators 410a, 410b. In the embodiment illustrated in FIG. 4B, the voltage regulators 410a, 410b are used as adjustable current sources to independently control the vibrational frequency of the vibrational transducers 415a, 415b. This may be accomplished, for example, by utilizing two external adjustable potentiometers 420a, 410b. Other solutions are also possible (e.g., a switch to use one potentiometer 420 to adjust both voltage regulators 410a, 410b, or more advanced circuitry). In the embodiment illustrated in FIG. 4B, the counters 440, 445 are configured to increment only upon activation of the vibrational transducer 415a, although it will be appreciated that other counting methods are also possible.

Figure 4C:
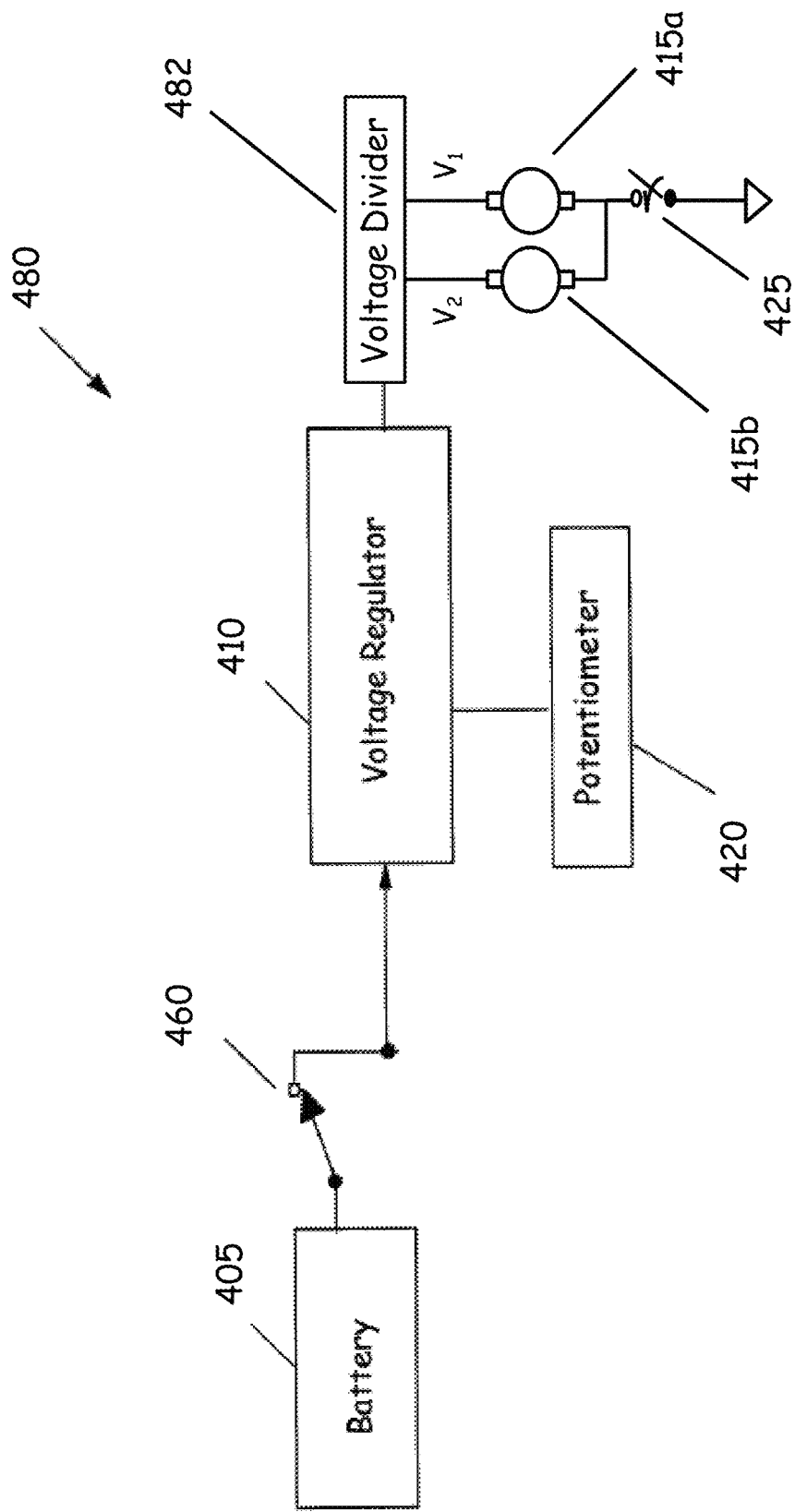

FIG. 4C is yet another block diagram of an example embodiment of a vibrotactile stimulator 480. Rather than including two voltage regulators 410a, 410b and two potentiometers 420a, 420b as in the voltage regulator 470, the voltage regulator 480 includes one voltage regulator 410, one potentiometer 420, and a voltage divider 482. The voltage divider 482 splits a voltage from the voltage regulator 410 into a first voltage $V_1$, which is sent to the first vibrational transducer 415a, and a second voltage $V_2$, which is sent to the second vibrational transducer 415b. The voltage divider 482 may comprise, for example, a network of resistors configured to proportionally split whatever voltage is input. A voltage divider 482 may be useful, for example, in embodiments in which the difference between the vibrating frequencies of the vibrational transducers 415a, 415b is desirably a certain delta (e.g., between about 20 Hz and about 60 Hz different, about 40 Hz different). Some commercially available voltage regulators 410 are able to output two different voltages such that the voltage divider 482 may be omitted. In some embodiments, the illustrated potentiometer 420 may be replaced by a first potentiometer 420a between the voltage divider 482 and the first vibrational transducer 415a and a second potentiometer 420b between the voltage divider 482 and the second vibrational transducer 415b, which can allow independent control over the vibrating frequencies of the vibrational transducers 415a, 415b.

Although duplicating the voltage regulators 410a, 410b and the potentiometers 420a, 420b may be more expensive than other examples described herein, such embodiments may have better (e.g., more consistent) power characteristics, resulting in more uniform and/or precise control over vibrating frequency.

The vibrotactile stimulator 480 does not include the counters 440, 445, which may be appropriate, for example for devices after it has been determined that the subject is known or believed to be likely to have high compliance. The vibrotactile stimulator 480 could include counters 440, 445, and any of the vibrotactile stimulators described herein may omit the counters 440, 445. For simplification, the vibrotactile stimulator 480 does not a low battery indicator 450 or a low battery LED, but the vibrotactile stimulator 480 could include a low battery indicator 450 or a low battery LED, and any of the vibrotactile stimulators described herein may omit the low battery indicator 450 and/or the low battery LED.

Figure 4D:
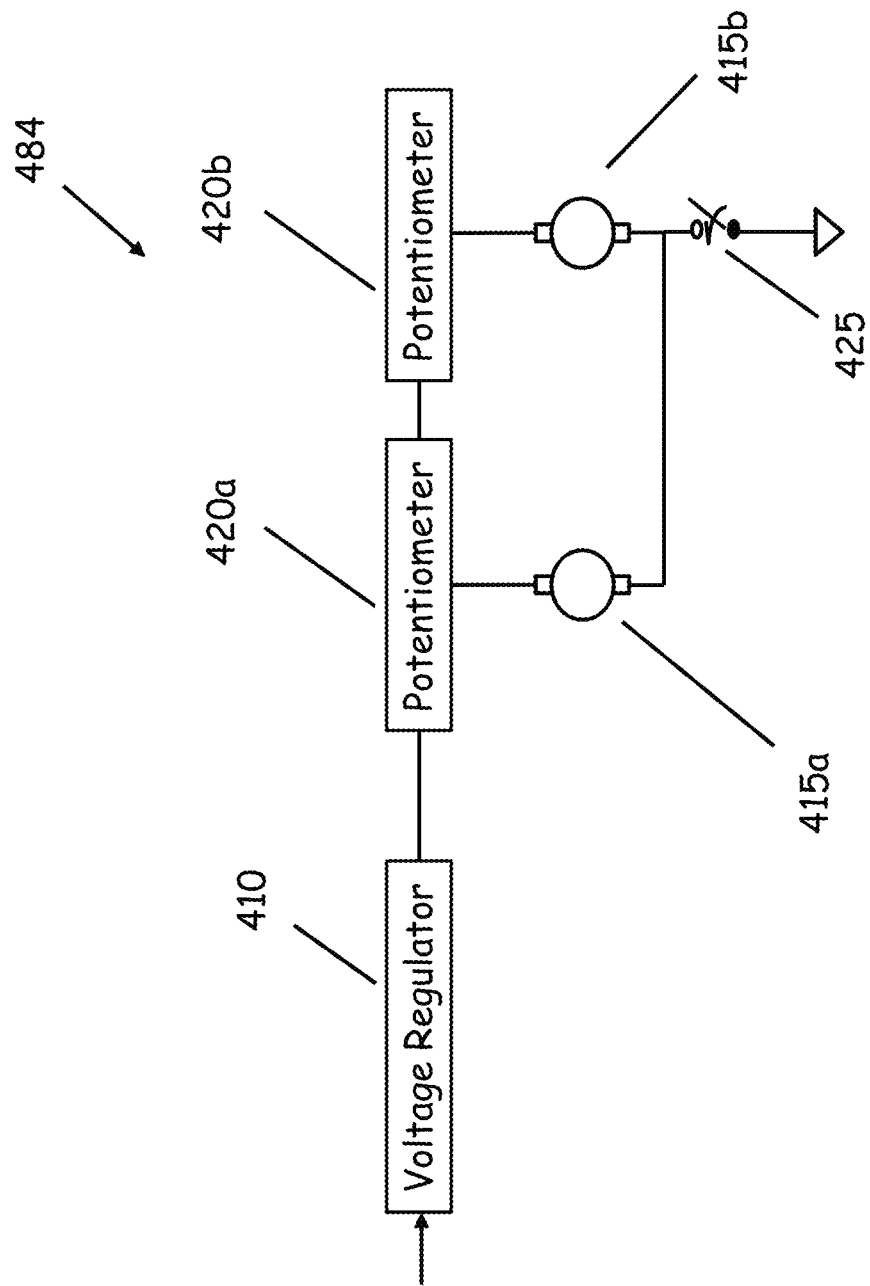

FIG. 4D is still another block diagram of an example embodiment of a vibrotactile stimulator 484. The vibrotactile stimulator 484 includes a voltage regulator 410, a first potentiometer 420a, and a second potentiometer 420b. Adjustment of the first potentiometer 420a adjusts the voltage to the first vibrational transducer 415a, and thus the vibrating frequency of the first vibrational transducer 415a. Adjustment of the first potentiometer 420a also adjusts the voltage to the second potentiometer 420b, and then the voltage to the second vibrational transducer 415b, and thus the vibrating frequency of the second vibrational transducer 415b. Adjustment of the second potentiometer 420b adjusts the voltage to the second vibrational transducer 415b, and thus the vibrating frequency of the second vibrational transducer 415b. The vibrotactile stimulator 484 allows adjustment of the vibrating frequency of the vibrational transducers 415a, 415b together and independently. For simplification, FIGS. 4D-4F do not show components such as the counters 440, 445, the battery 405, the switch 460, the low battery indicator 450, or the low battery LED.

Figure 4E:
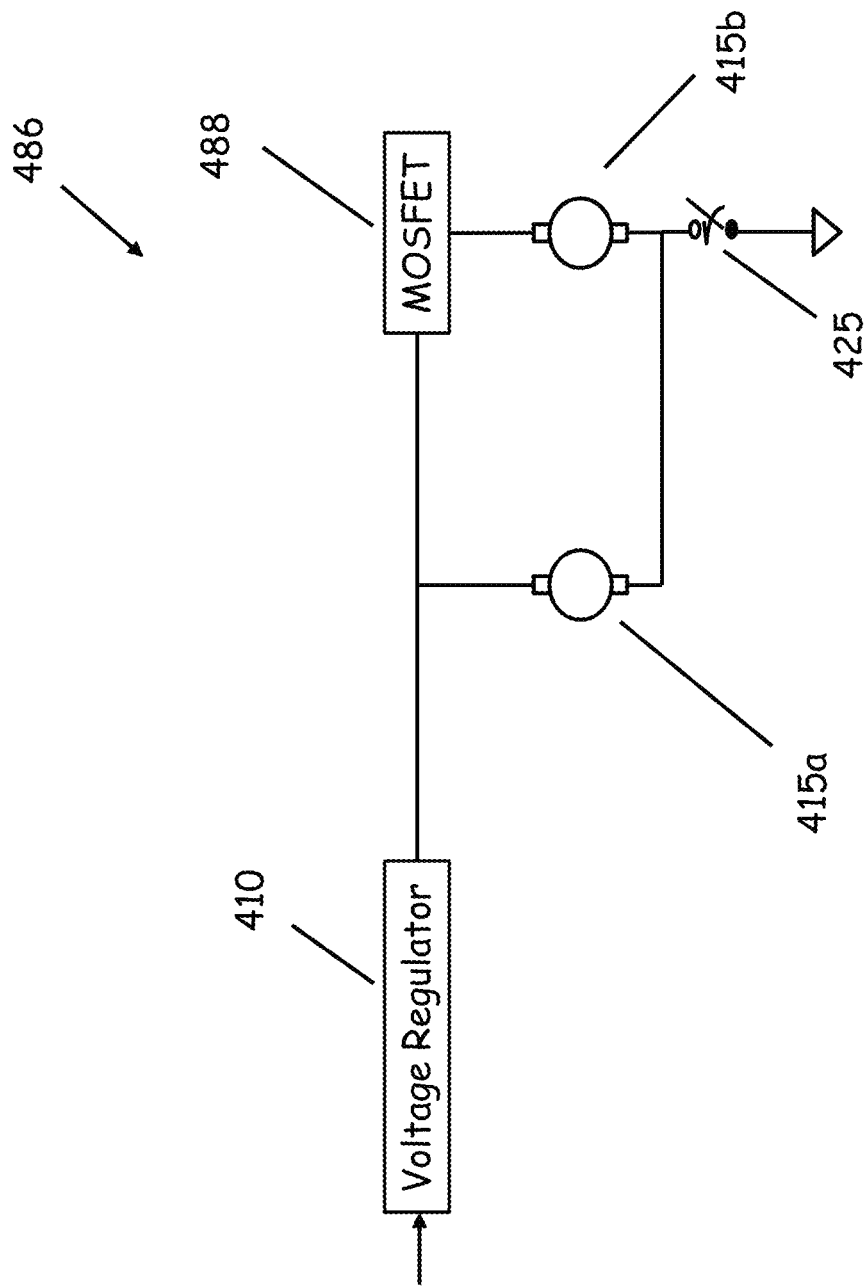

FIG. 4E is still yet another block diagram of an example embodiment of a vibrotactile stimulator 486. The vibrotactile stimulator 486 does not include a potentiometer 420 or redundant components such as two voltage regulators 410a, 410b. The vibrotactile stimulator 486 includes a voltage regulator 410 and a metal oxide semiconductor field effect transistor (MOSFET) 488 such as a bipolar junction transistor (BJT). The MOSFET 488 can adjust the voltage to the second vibrational transducer 415b, for example by modulating the pulse width of the signal. The MOSFET 488 may be adjustable such that the on and/or off time of the signal modulation may be adjusted to provide appropriate voltage to the second vibrational transducer 420b to effect the desired vibrating frequency.

Figure 4F:
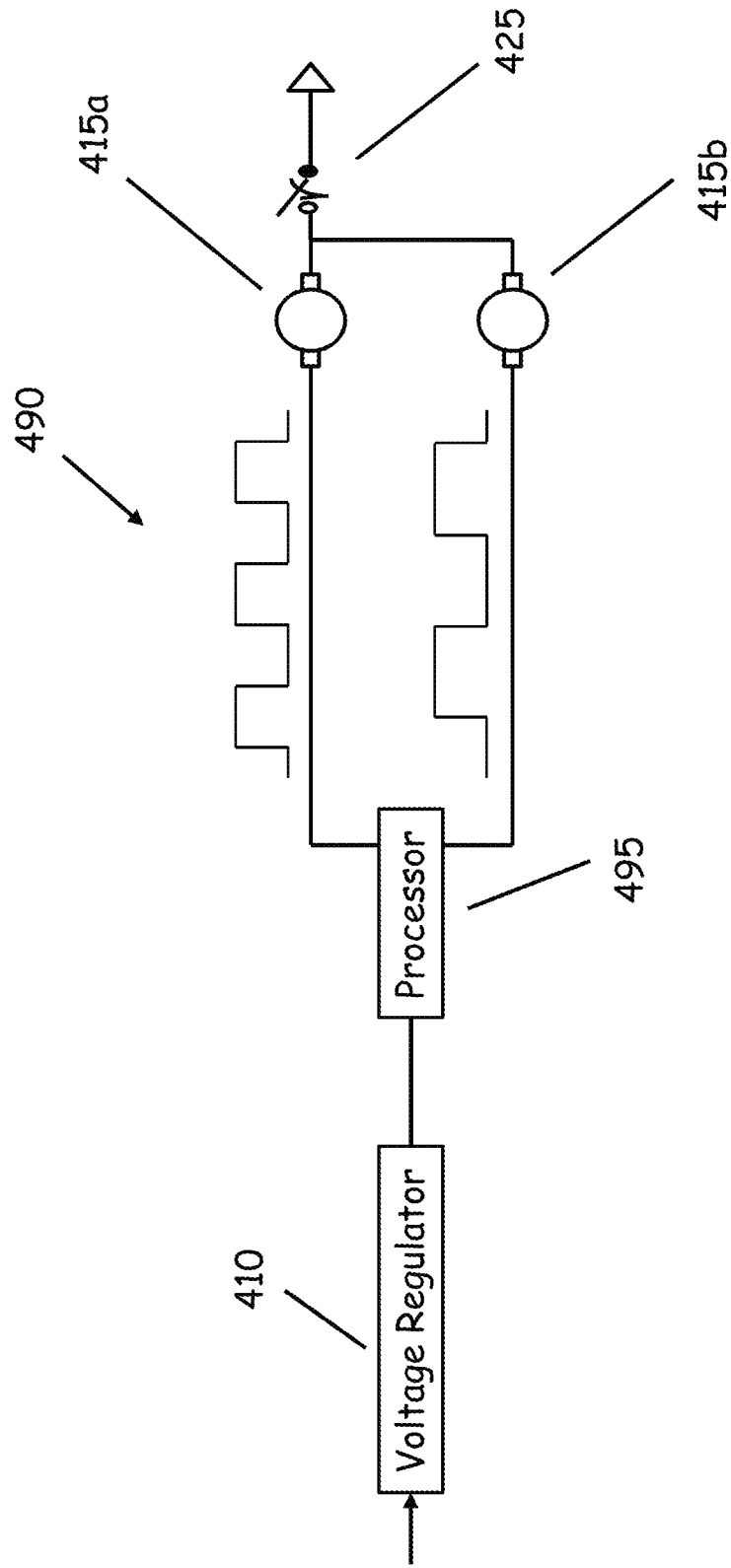

FIG. 4F is another block diagram of an example embodiment of a vibrotactile stimulator 490. The vibrotactile stimulator 490 does not include a potentiometer 420 or redundant components such as two voltage regulators 410a, 410b. The vibrotactile stimulator 490 includes a processor 495. The processor 495 is configured to adjust one or more parameters of the signals sent to the vibrational transducers 415a, 415b such as voltage, pulse width, frequency, amplitude, duty cycle, combinations thereof, and the like. While a processor 495 may be an expensive component compared, for example, to a potentiometer, the processor 495 may be able to replace multiple components of the vibrotactile stimulator 490 and/or as system comprising the vibrotactile stimulator 490. The processor 495 may allow much more flexibility in adjustment of various parameters and/or stability in achieving parameters once set.

FIGS. 4A-4F include many examples of components that can be used to achieve different vibrating rates between two vibrational transducers 415a, 415b. Any combination of analog and/or digital electronic components, including those described herein, switches, resistors, capacitors, amplifiers (e.g., operational amplifiers), diodes, inductors, comparators, transistors, gates, and the like may be designed affect voltage signals, which can result in the first vibrational transducer 415a having a first vibrating frequency and the second vibrational transducer 415b having a second vibrating frequency different than the first vibrating frequency, or to modify other vibrating parameters as discussed herein. In some embodiments, a portable computing device such as a smart phone or the like may include a processor that can be programmed (e.g., include an application) to provide the stimulation described herein, including providing different vibrating properties. Such a device can include inputs (e.g., through serial bus, lighting connector, wireless, etc.) such as the button 103, sensors, parameter setting, etc.

Figure 5A:
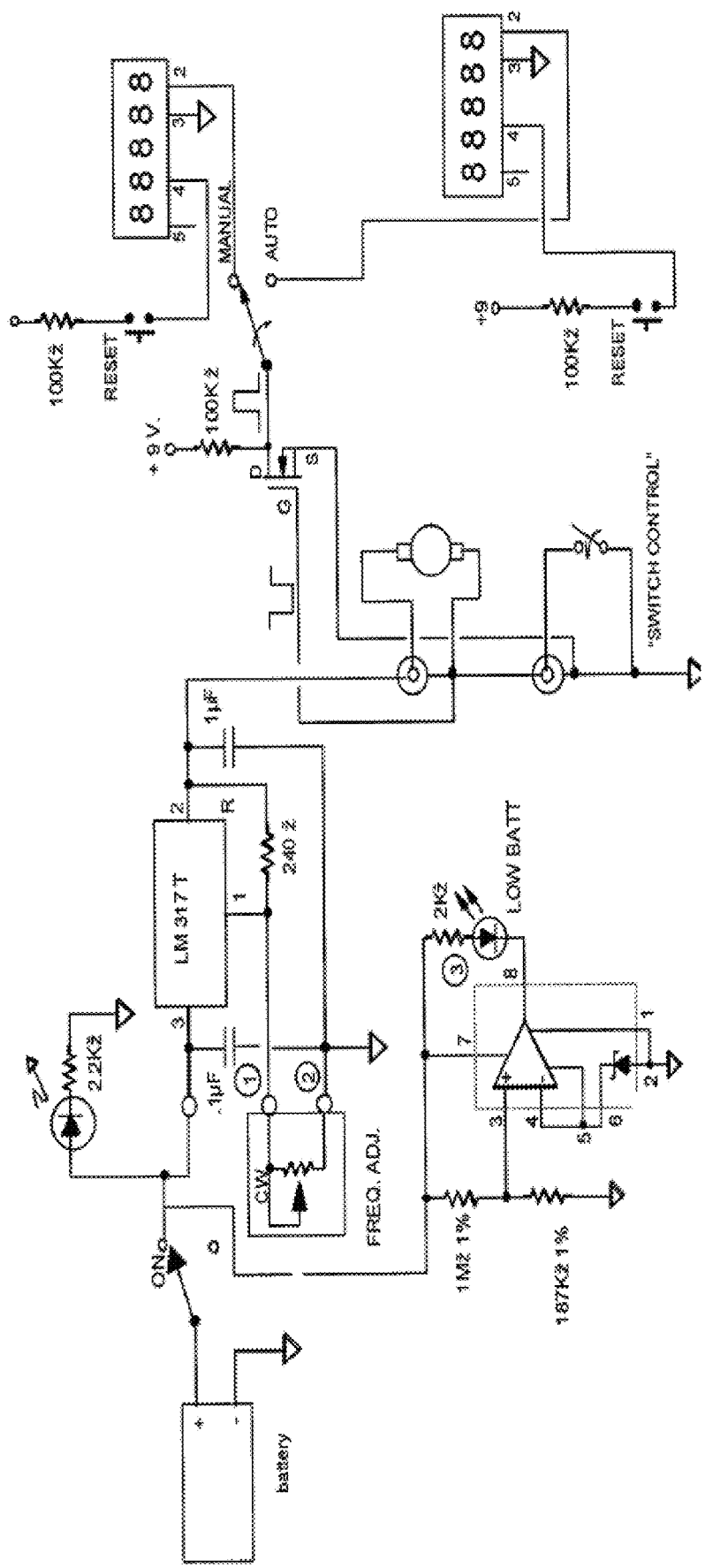
FIGS. 5A-5D are example circuit diagrams for a vibrotactile stimulator.
Figure 5B:
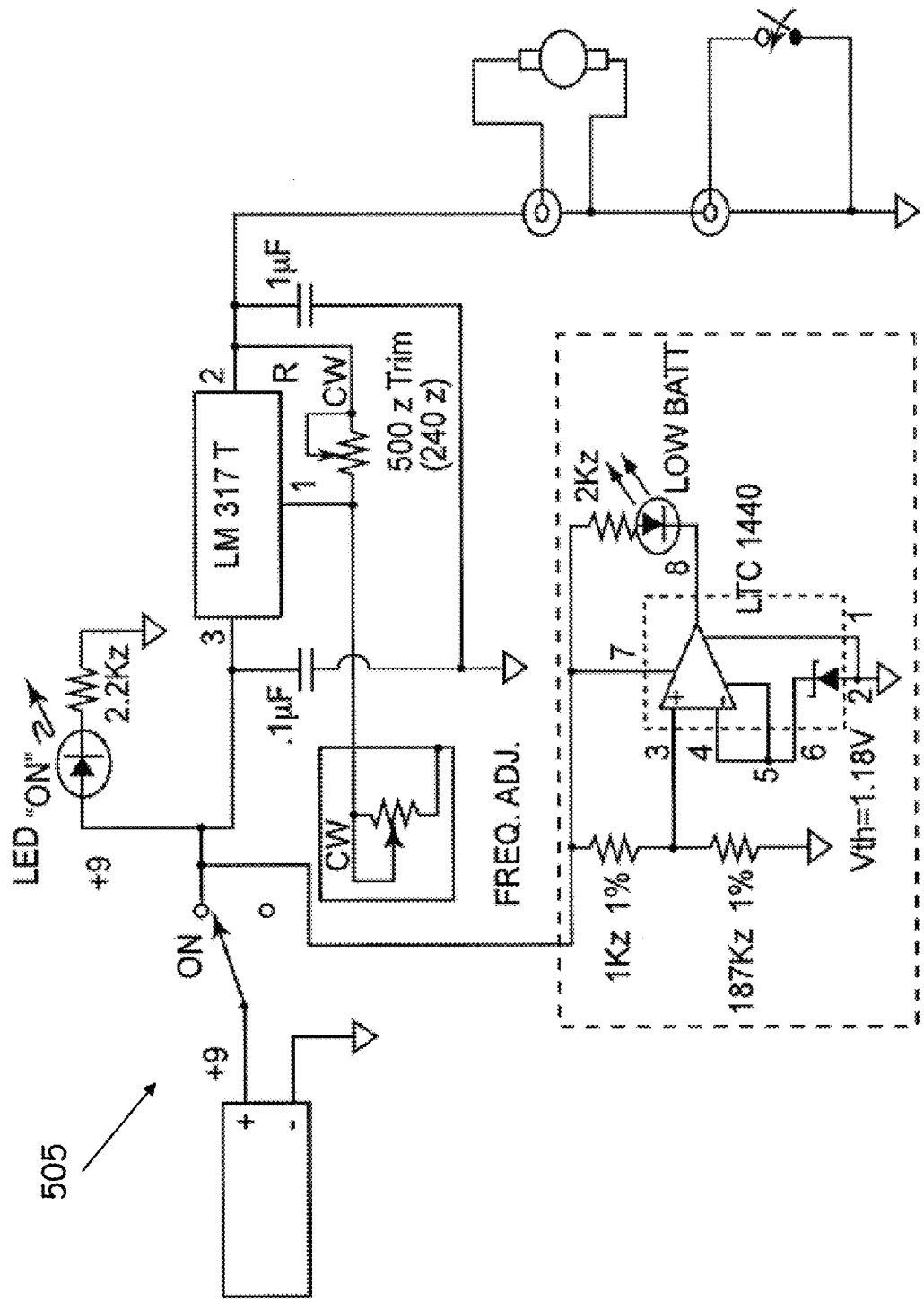
Figure 5C:
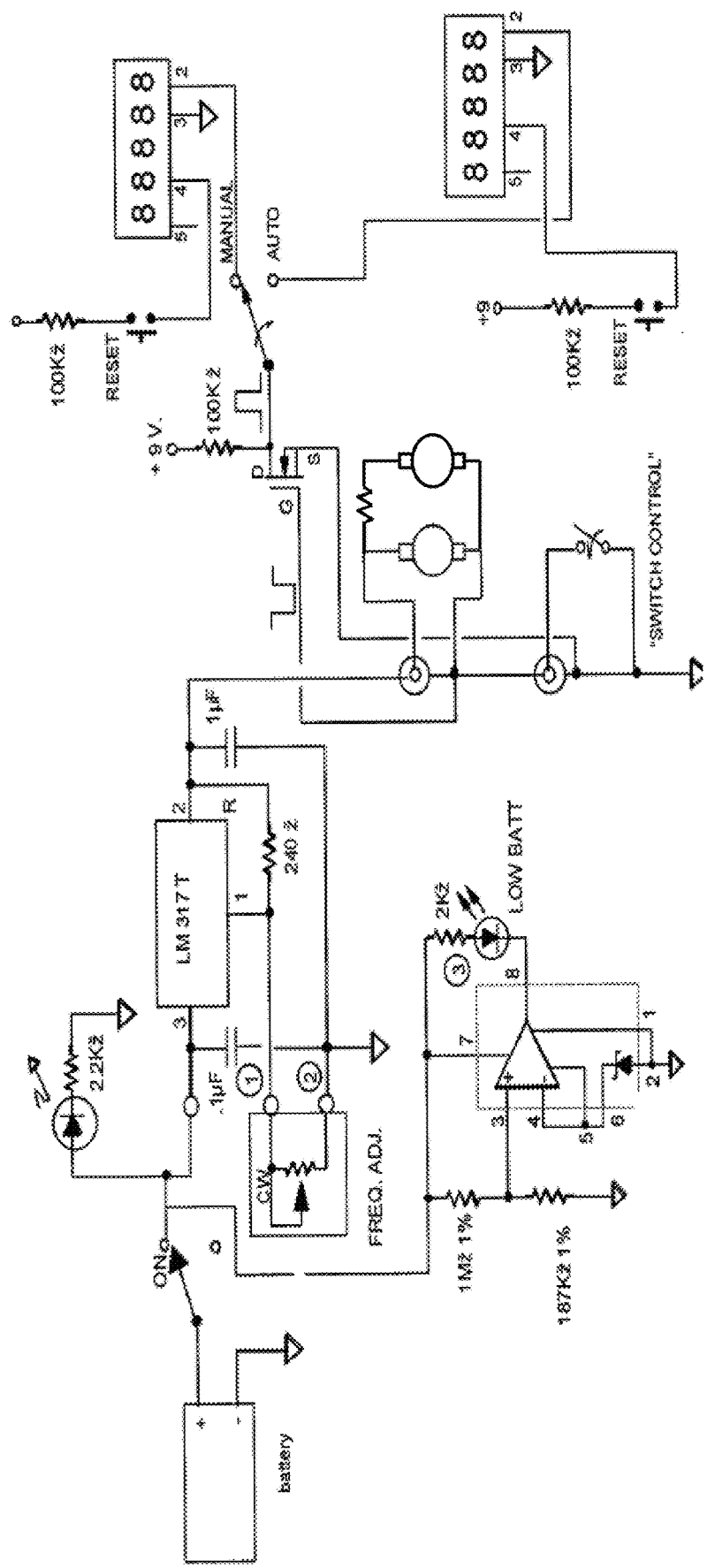
Figure 5D:
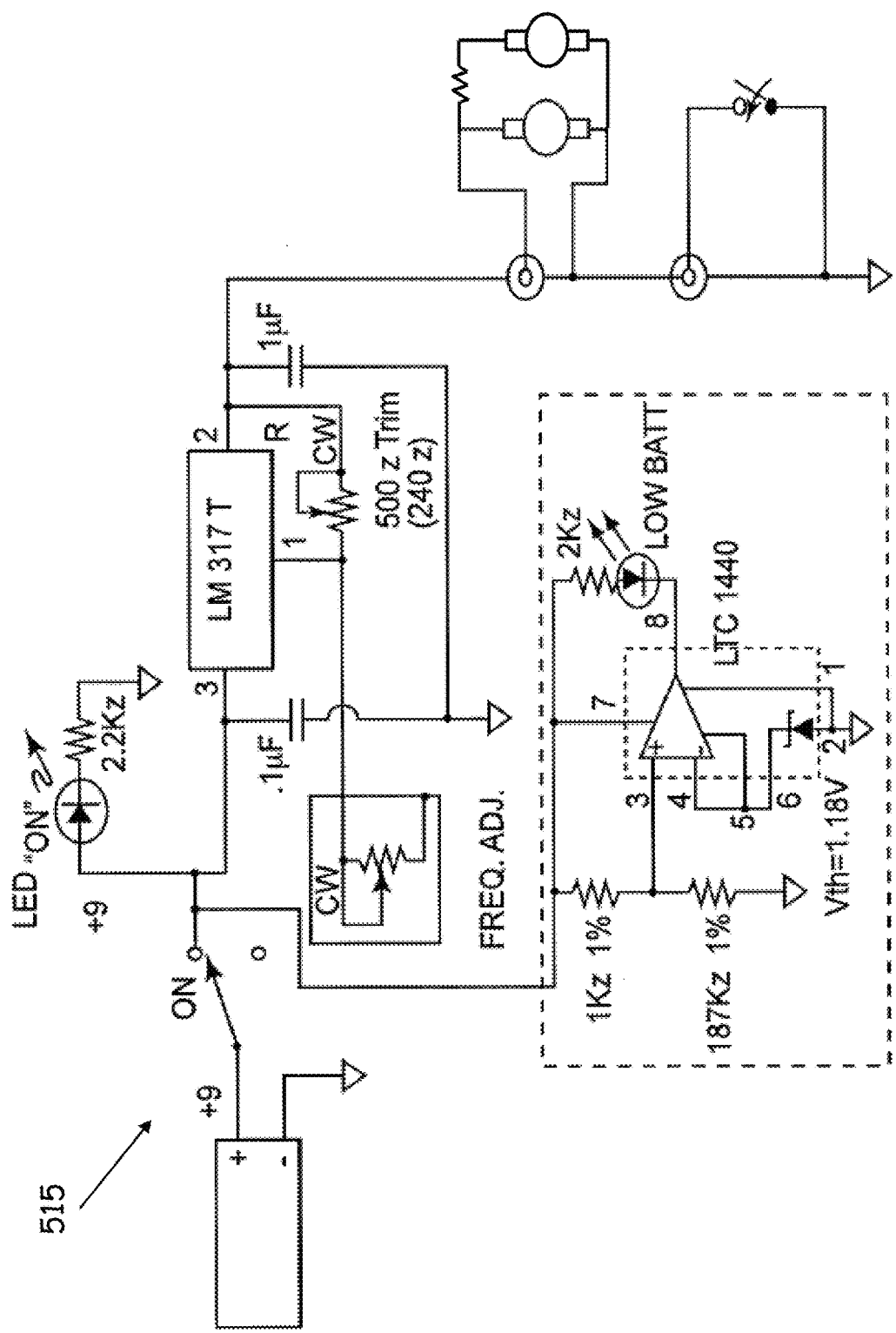

FIG. 5A is an example circuit diagram 500 for a vibrotactile stimulator (e.g., the vibrotactile stimulator 400). FIG. 5B is another example circuit diagram 505 for a vibrotactile stimulator (e.g., the vibrotactile stimulator 400). FIG. 5A is an example circuit diagram 500 for a vibrotactile stimulator (e.g., the vibrotactile stimulator 470). FIG. 5B is another example circuit diagram 505 for a vibrotactile stimulator (e.g., the vibrotactile stimulator 470). Example circuit diagrams 500, 505, 510, 515 are only example circuit architectures, and that the vibrotactile stimulators 400, 470 may be implemented via any suitable architecture. For example, the circuit diagrams 505, 515 do not include counters. For another example, the vibrational transducers in the circuit diagrams 510, 515 of FIGS. 5C and 5D, respectively, are shown in parallel, which may cause the vibrational transducers to have different vibrating frequencies if the vibrational transducers respond differently to the same input, other components may be added in the signal path ahead of one or both of the vibrational transducers (e.g., the resistor ahead of the right vibrational transducer, as shown in FIGS. 5C and 5D), portions of the architecture may be replicated, a new component may be added (e.g., processor, voltage divider, etc.), combinations thereof, and the like. Modifications similar to those described with respect to FIGS. 4A-4F and other modifications are also possible. In the embodiments illustrated in FIGS. 5A and 5C, both passive and discrete electrical components are shown, which can allow component attributes and tolerances to fit a known specification.

Figure 6:
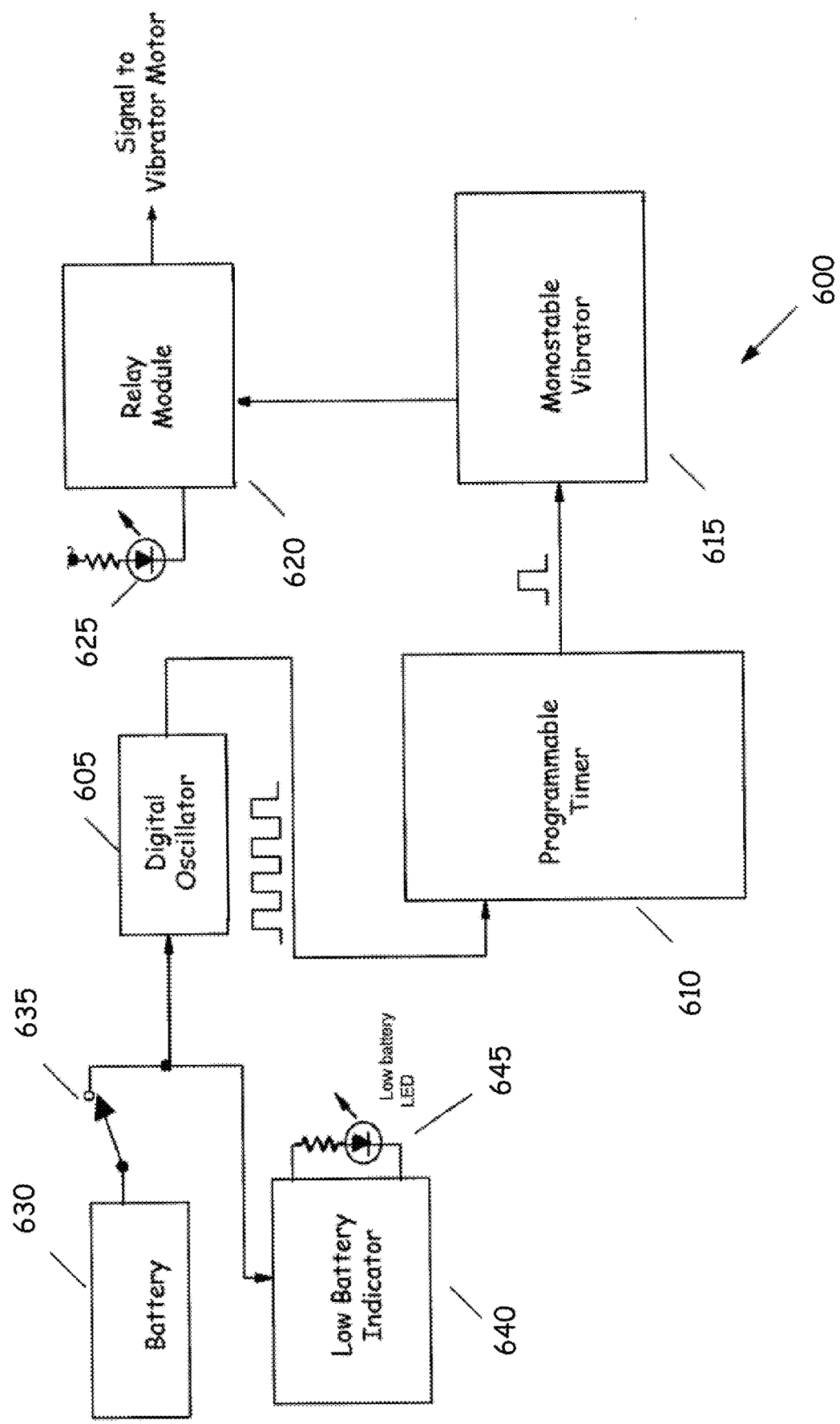
FIG. 6 is a block diagram of an example embodiment of an automatic timer circuit.

FIG. 6 is a block diagram of an example embodiment of an automatic timer circuit 700. In general, the automatic timer module is communicatively connected to the vibrotactile stimulator 300 shown in FIG. 3. As described herein, the automatic timer circuit 600 may actuate the count select mechanism 435, thereby engaging the automatic counter 445 and energizing the vibrational transducer(s) 405 for a predetermined period of time. In the embodiment illustrated in FIG. 6, the automatic timer circuit 600 comprises a digital oscillator 605 having an adjustable oscillating frequency of about 2.2 Hz to about 28 Hz. The output signal of the digital oscillator 605 is routed to a programmable timer 610 set to divide the periodic digital input signal by the value 4096. The input clock frequency from the digital oscillator 605 to the programmable timer 610 at least partially determines when an output pulse is generated. In the embodiment illustrated in FIG. 6, the output pulse period may be generated in a range from about 3 to about 30 minutes. Subsequently, the programmable timer 610 output pulse triggers an adjustable monostable vibrator 615. An output pulse width of the adjustable monostable vibrator 615 sets the "on" time for the vibrational transducer(s) 415 by energizing a relay through a transistor switch. In the embodiment illustrated in FIG. 6, the transistor switch and relay control is integral to relay module 620. An LED 625 indicates that the relay has been activated, which energizes the vibrational transducer(s) 415 in the automatic mode. In some embodiments, the duration that the vibrational transducer(s) are energized is between about 5 seconds and about 15 seconds.

The automatic timer circuit 600 is powered by a battery 630 or other power source when a power switch 635 is in the "on" position. The automatic timer circuit 600 may optionally include a low battery indicator 640 such that if the battery 630 voltage drops below a specified voltage level, an indicator specifying that event is generated. In the embodiment illustrated in FIG. 6, an LED "Low Battery" indicator 645 comes on. It will be appreciated that the battery 630, the power switch 635, the low battery indicator 640 and the LED 645 may be used to power the vibrotactile stimulator 300 as shown in FIG. 3.

Figure 7A:
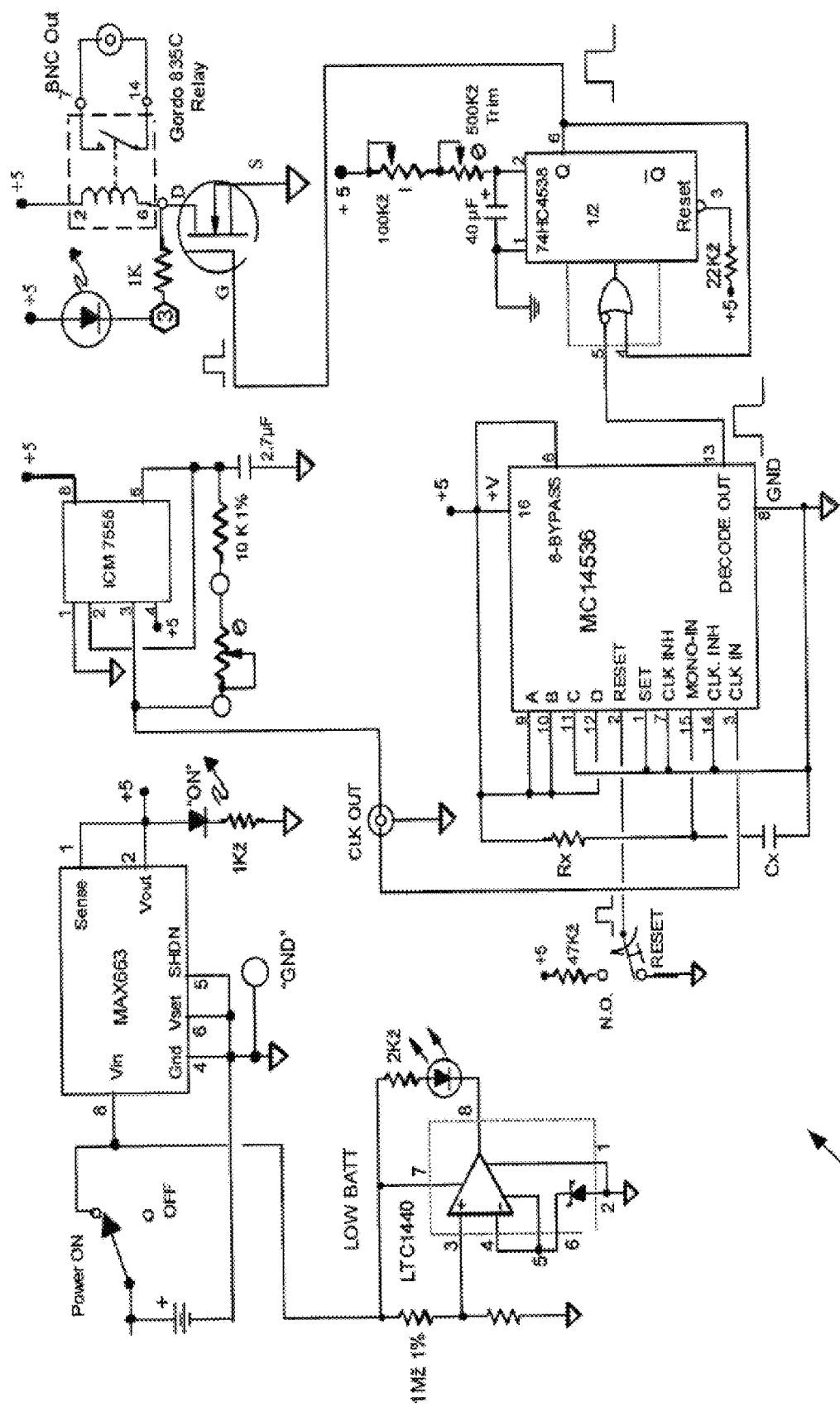
FIG. 7A is an example circuit diagram for an automatic timer.
Figure 7B:
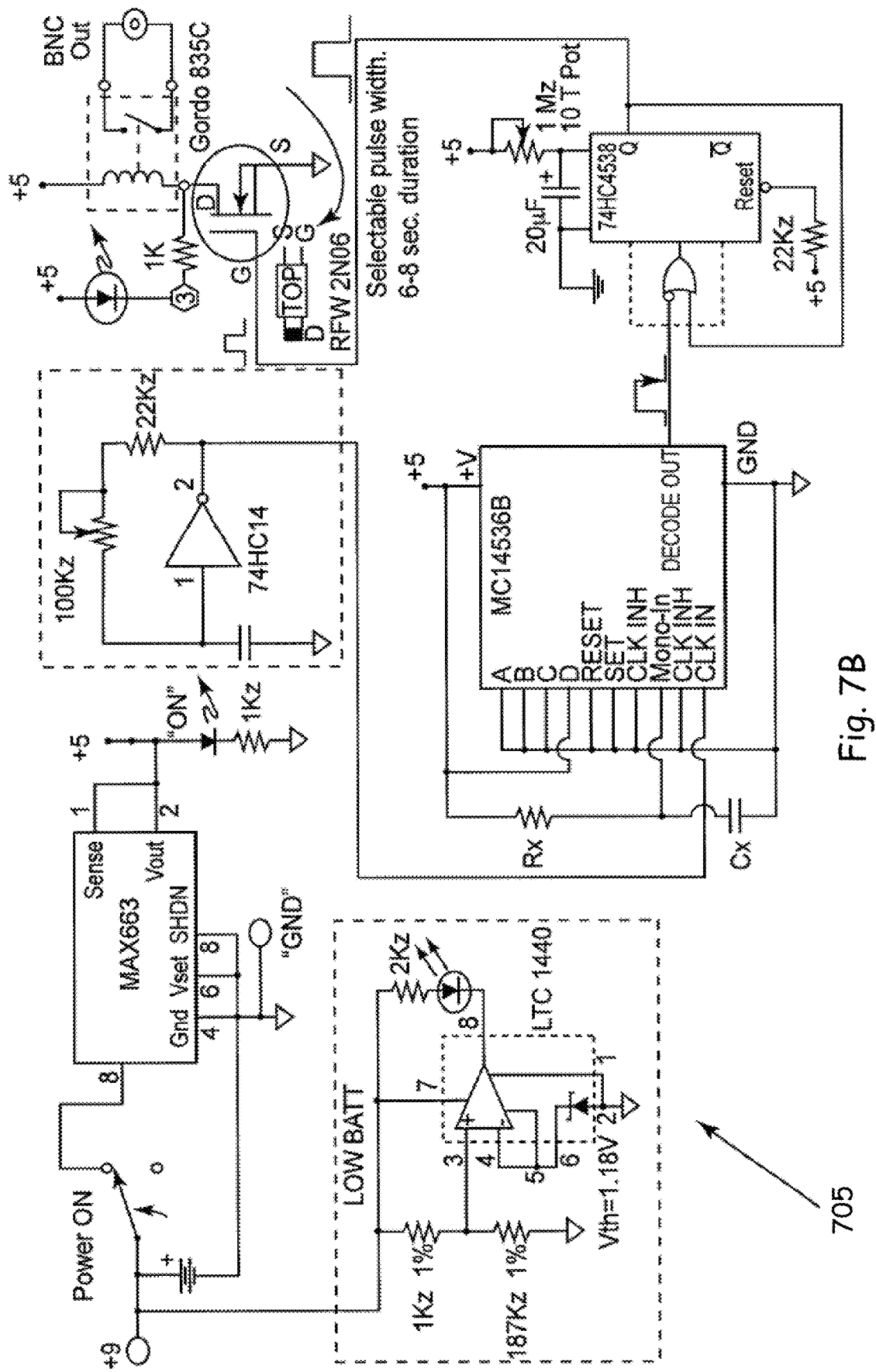
FIG. 7B is another example circuit diagram for an automatic timer.

FIG. 7A is an example circuit diagram 700 for an automatic timer (e.g., the automatic timer 600 of FIG. 6). Example circuit diagram 700 is only an example circuit architecture, and that the automatic timer circuit 600 may be implemented via any suitable electrical architecture. In the embodiment illustrated in FIG. 8A, both passive and discrete electrical components are shown, such that component attributes and tolerances can fit a known specification. FIG. 7B is another example circuit diagram 705 for an automatic timer (e.g., the automatic timer 600 of FIG. 6). In certain embodiments, the manual counter 440, the automatic counter 445, and the automatic timer circuit 600 can be incorporated into a single functional counter, and timer module that is mounted internally and communicatively connected to the vibrotactile stimulator 300.

Figure 8:
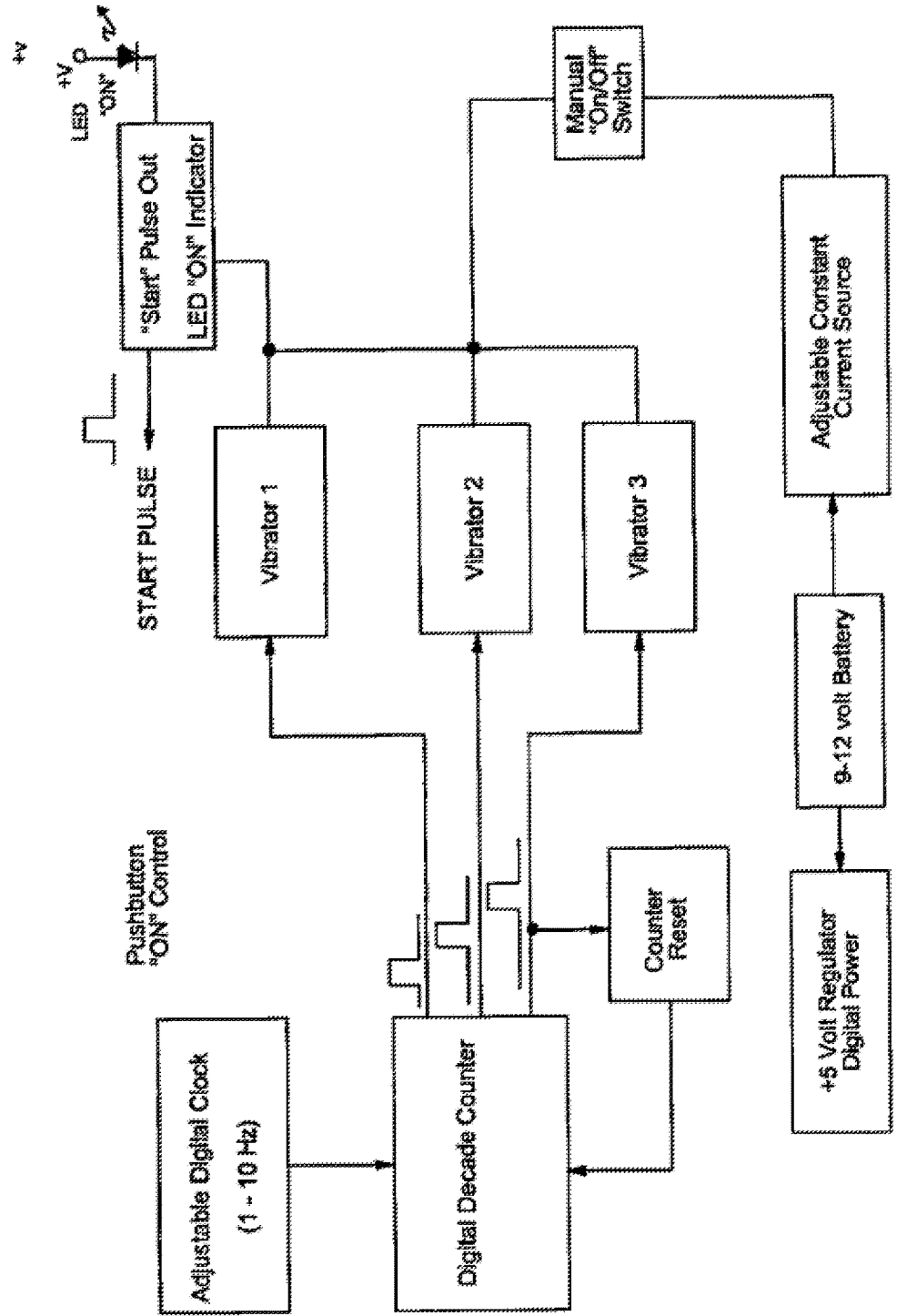
FIG. 8 is a block diagram of another example embodiment of a vibrotactile stimulator.

FIG. 8 is a block diagram of another example embodiment of a vibrotactile stimulator 800. In general, the vibrotactile stimulator 800 is a battery-powered device that sequentially activates one or more small DC vibrational transducers as described herein. An adjustable digital clock can set the timing for separate events. The clock frequency can be adjusted between about 1 Hz and about 10 Hz. This clock, in conjunction with a digital decade counter, can generate sequential pulses that can control the "on" and "off" durations of individual vibrators. At the end of the pulse cycle, a short reset pulse can be generated to reset the decade counter and begin the next cycle of pulses.

A subject can control the vibrotactile stimulator 800 by activating an "ON" switch. The switch may activate an LED indicator. The switch generates a digital pulse that can be used for coordinating various recording devices. When the switch is released, the vibration pulses will stop. In some embodiments, the subject does not perceive any delay between activating the "ON" switch and the first vibration to the throat.

Figure 9:
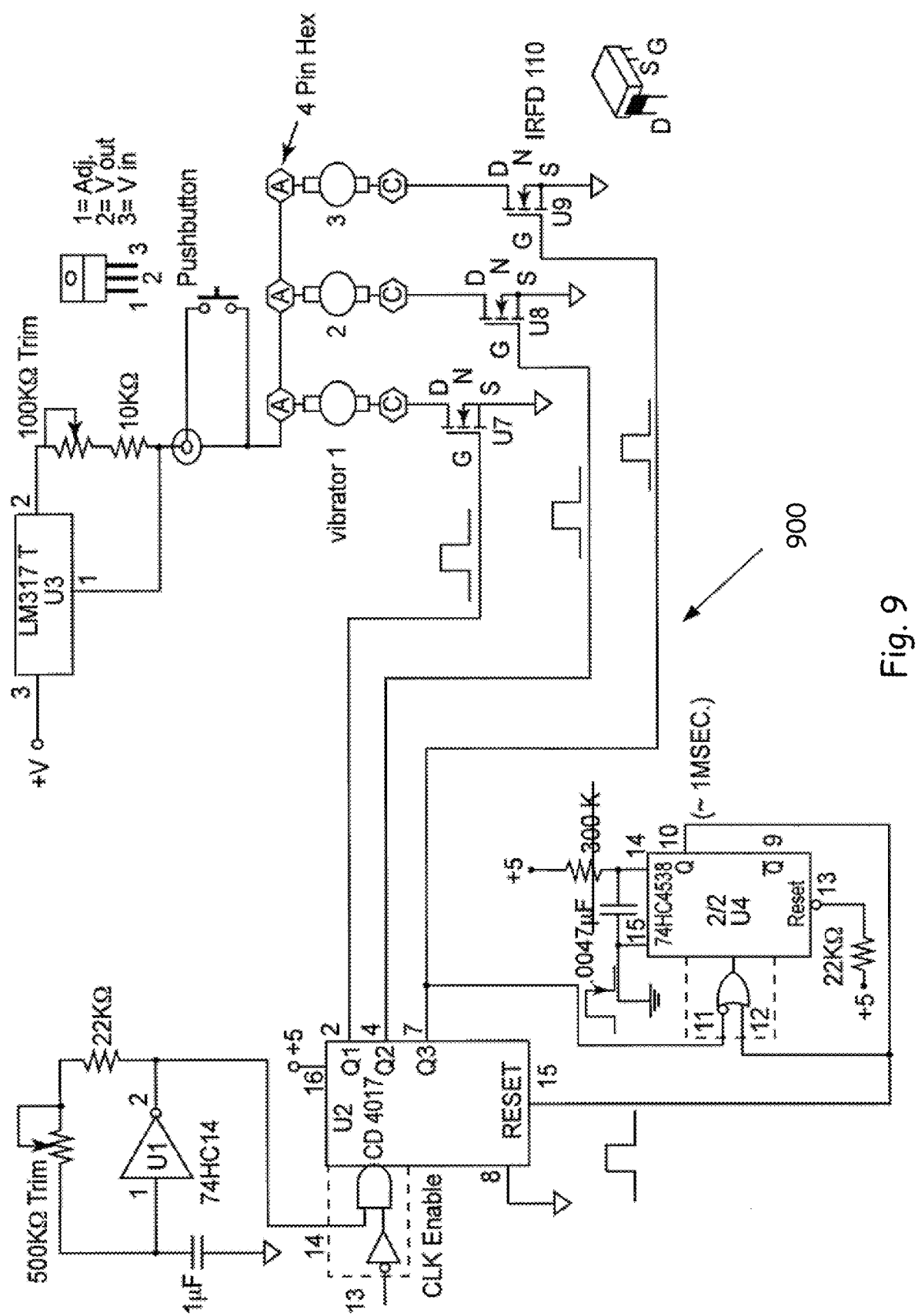
FIG. 9 is an example circuit diagram for a vibrotactile stimulator.
Figure 10:
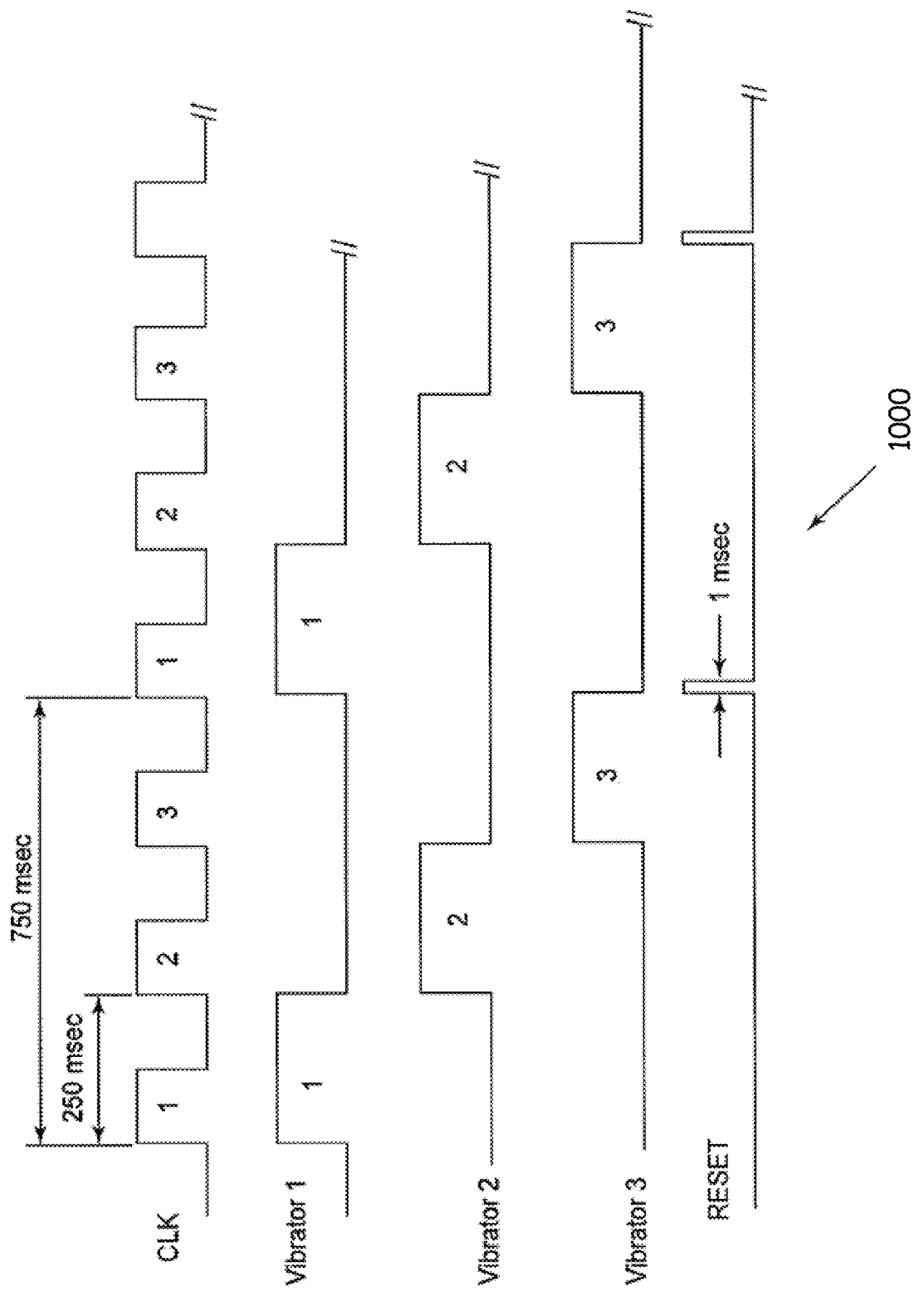
FIG. 10 is a diagram depicting a clock-based sequential vibrator control.
Figure 11:
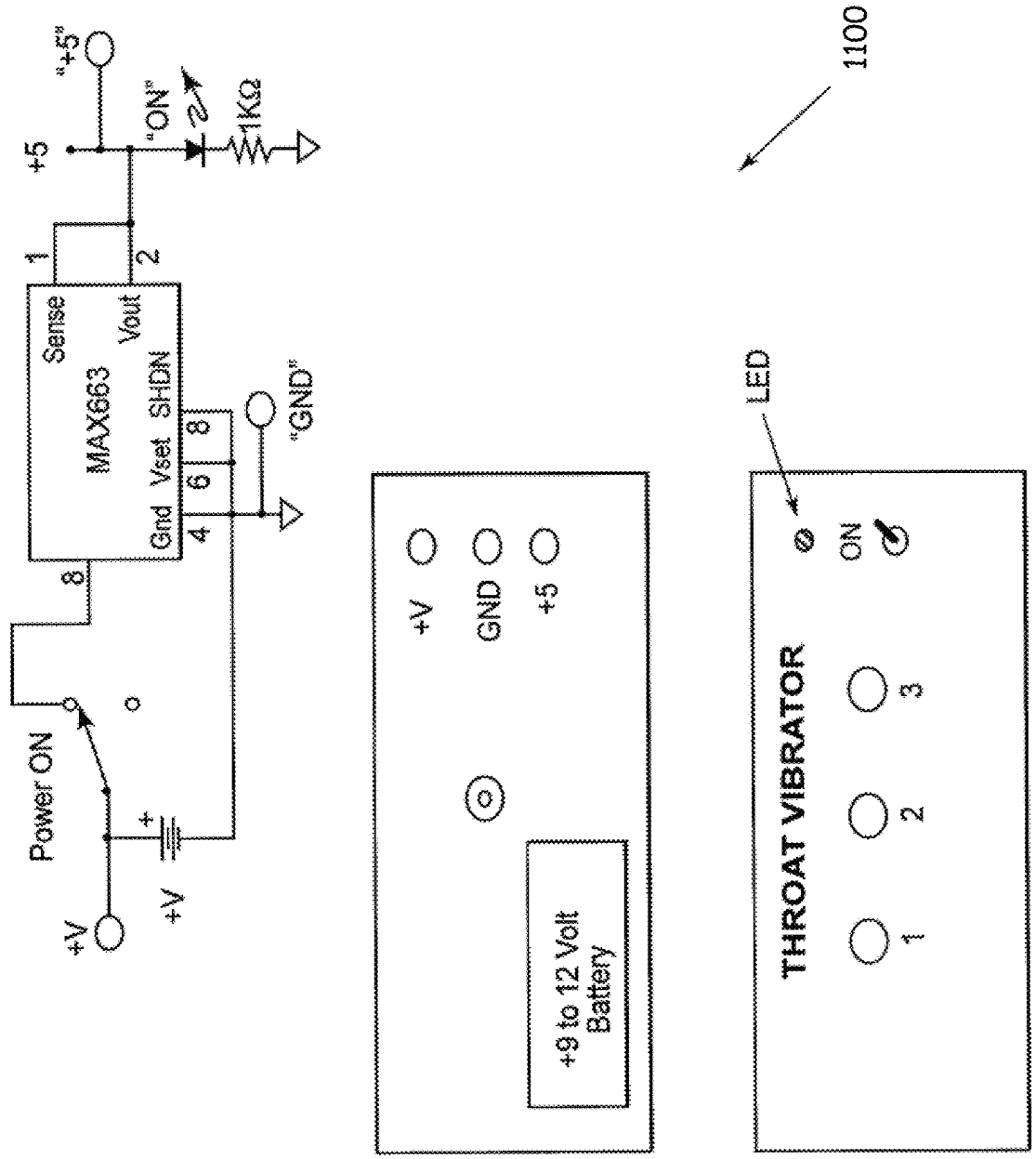
FIG. 11 is a diagram of an example embodiment of a controller box for a vibrotactile stimulator.

FIG. 9 is an example circuit diagram 900 for a vibrotactile stimulator (e.g., the vibrotactile stimulator 800). FIG. 10 is a diagram 1000 depicting a clock-based sequential vibrator control (e.g., implementable with the vibrotactile stimulator 800). FIG. 11 is a diagram of an example embodiment of a controller box 1100 for a vibrotactile stimulator (e.g., the vibrotactile stimulator 800). The controller box 1100 may set one or more vibrotactile stimulator 800 operating parameters. For example, an operating parameter may include a stimulus type, a stimulus shape (e.g., a wave shape (e.g., sinusoidal, sawtooth, square wave)), a stimulus continuousness (e.g., continuous, pulsed), a stimulus rate (constant or changing over time), a stimulation continuousness (e.g., continuous, pulsed), a stimulus amplitude (constant or changing over time), combinations thereof, and the like. The control box 100 may be configured to allow for stimulation for a specific duration upon activation of the button or as long as the button is depressed. In some embodiments, the duration of stimulation is about 2 seconds to about 6 seconds.

B. Methods and Uses

The systems and methods described herein can be used to treat a number of conditions and disorders including, but not limited to, stroke, cerebral hemorrhage, traumatic brain injury, dysphagia, post brain surgery, Parkinson's disease, multiple sclerosis, birth defects, ALS, cerebral palsy, CNS injury, supranuclear palsy, and any other neurological disease, neurological disorder, neurological injury, neurological impairment or neurodegenerative disease that affects voluntary motor control of the hyoid, pharynx, larynx, oropharyngeal area, and/or hyolaryngeal complex. Neurological impairments that are contemplated include reflex actions that involve interactions between afferent and efferent paths, at the spinal cord or in the brain stem, as well as higher order interactions in the primary motor cortex of the hemispheres. The systems and methods may apply to subjects who have lost or partially lost the ability to voluntarily control motor functions and/or to subjects who were born with birth defects that have prevented them from having voluntary motor control, such as cerebral palsy. The systems and methods may be applicable to treating various speech motor control disorders such as stuttering and laryngeal dystonia.

The term "motor control" as used herein refers to the ability of a subject to control activity of their muscle at will, and should not be confused with a motor such as a vibrator motor of a vibrational transducer. For instance, in some embodiments, motor control refers to the ability of a subject to swallow at will. Subjects with dysphagia, which is the complete or partial loss of the ability to swallow, can be treated with the systems and methods described herein. In some embodiments, the disease or disorder reduces or delays motor control of swallowing and/or results in delayed or reduced elevation of the hyolaryngeal complex, which does not allow the subject to prevent food or liquid from entering the airway.

In some embodiments, a method comprises stimulating a substitute site for an affected area with a system or device to trigger motor control of the affected area. The term "recovering" as used herein includes within its meaning obtaining the ability to volitionally control motor functions. "Volitionally" as used herein means at the will of the subject. A "substitute site" as used herein means an area of the body that is capable of eliciting a desired reflex, but is not a sensory region that is able to elicit reflex in impaired subjects.

Subjects are often not responsive to stimulation in the oral and pharyngeal cavities, but remain sensate to vibratory stimulation to the areas of the human head which include anatomical structures (e.g., muscles, nerves, and/or connective tissue) that work in concert to affect deglutition. By providing sensory stimulation to sensate areas on the throat, substitute stimulation can be used to enhance the volitional elicitation of swallowing. For example, subjects with dysphagia following neurological disease usually have sensory loss in the oropharyngeal area, which is normally required to be sensate in order to elicit safe swallowing without aspiration. Sensory triggering in "substitute sites" can enhance the elicitation of reflex and volitional swallowing, such as stimulation of afferents from the laryngeal area contained in the superior laryngeal area.

Basic studies suggest that the second order neurons excited by afferents in the superior laryngeal nerve are selectively excitable at particular vibrational frequencies, and that stimulation between about 30 Hz and about 70 Hz may be most useful for exciting the swallowing system in the brainstem. Subjects are often not responsive to stimulation in the oral and pharyngeal cavities, but remain sensate to vibratory stimulation to the throat area including the skin and laryngeal cartilages underlying the skin. In certain such embodiments, the throat is the substitute site and providing sensory stimulation to the throat can elicit volitional swallowing.

Vibrational frequencies outside the range of about 30 Hz to about 70 Hz may also be useful to elicit volitional swallowing. In some embodiments, two different vibrating frequencies can elicit more volitional swallowing than one vibrating frequency. For example, a first vibrating frequency between about 30 Hz and about 60 Hz (e.g., about 30 Hz) and a second vibrating frequency between about 60 Hz and about 90 Hz (e.g., about 70 Hz) may incorporate the about 30 Hz vibrating frequency. For another example, as described in further detail herein, a first vibrating frequency between about 50 Hz and about 90 Hz (e.g., about 70 Hz) and a second vibrating frequency between about 90 Hz and about 130 Hz (e.g., about 110 Hz) can provide at least a 65% or 85% increase in the urge to swallow over control.

In some embodiments, a method for stimulating swallowing in a subject comprises applying a first vibrotactile stimulation to a throat area of the subject and applying a second vibrotactile stimulation to the throat area of the subject. The first vibrotactile stimulation is at a first vibrating rate. The second vibrotactile stimulation is at a second vibrating rate different than the first vibrating rate. Applying the first vibrotactile stimulation and applying the second vibrotactile stimulation may include the subject voluntary activating vibrotactile stimulators. Applying the first vibrotactile stimulation and applying the second vibrotactile stimulation may include automatically activating the vibrotactile stimulators. Applying the first vibrotactile stimulation may be at least partially simultaneous with applying the second vibrotactile stimulation. The first vibrating rate may be between about 50 Hz and about 90 Hz and the second vibrating rate may be between about 90 Hz and about 130 Hz. The first vibrating rate may be between about 30 Hz and about 60 Hz and the second vibrating rate may be between about 60 Hz and about 90 Hz. The first vibrating rate may be about 70 Hz and the second vibrating rate may be about 110 Hz. The first vibrating rate may be about 30 Hz and the second vibrating rate may be about 70 Hz. The first vibrating rate may be between about 20 Hz and about 60 Hz different than the second vibrating rate. The first vibrating rate may be between about 10 Hz and about 40 Hz different than the second vibrating rate. The first vibrating rate may be about 40 Hz different than the second vibrating rate. The first vibrating rate may be about 25 Hz different than the second vibrating rate.

The site for stimulation can be adjusted depending upon the desired motor control. Those of skill in the art will readily understand where to locate the stimulation based on the disorder. In some embodiments, the affected area is the area of the body responsible for swallowing, speech, or voice. In some embodiments, the affected area is the oropharyngeal area. In some embodiments, the substitute site is the area of the throat over the larynx. In some embodiments, the recovered motor control is volitional swallowing.

By providing a vibratory stimulus to the neck of a subject, mechanoreceptors in the skin will be activated, providing feedback to the brain stem and brain to assist with triggering voluntary initiation of swallowing, speech, or voice. At greater vibration amplitudes, mechanical stimulation induces movement of the thyroid cartilage and of the extrinsic and intrinsic laryngeal muscles in the region including: the platysma, the stemohyoid, the sternothyroid, the thyrohyoid, the cricothyroid, and the thyroarytenoid muscles. Some of these muscles contain muscle spindles. The muscle spindle afferents can provide sensory feedback to the central nervous system to assist with triggering voluntary initiation of the muscles for swallowing, speech, and voice initiation.

In some embodiments, the stimulation is asserted immediately before a volitional attempt to move or carry out the physiological impaired function, such as swallowing or speaking. In some embodiments, the stimulation comprises an onset period in which the stimulation is asserted about 1 second to about 10 seconds before, about 0.1 seconds to about 1 second before, about 0.2 seconds to about 0.5 seconds before, or about 0.2 seconds to about 0.4 seconds before the volitional attempt. The stimulation may be asserted at the same time as the volitional attempt. It will be appreciated that constant or periodic stimuli that happen to coincide with a volitional attempt would not necessarily be considered to be asserted immediately before the volitional attempt, for example because an aspect of the volitional attempt is the ability to volitionally coincide the attempt with the stimulus.

The sensory modality for stimulation may include, but is not limited to, vibratory stimulation, pressure stimulation, auditory stimulation, optical stimulation, ultrasound stimulation, temperature stimulation, visual stimulation, electrical stimulation, olfactory stimulation, taste stimulation, combinations thereof, and the like. The stimulation may be controlled electrically, mechanically, chemically, biologically, or by any other appropriate method. In some embodiments, the stimulation is vibratory, tactile, pressure, or a combination thereof. In some embodiments, the stimulation is vibrotactile. In some embodiments, vibratory stimulation is combined with another type of stimulation, such as electrical skin surface stimulation (e.g., having the same or different timing). Combination of two types of stimulation, like stimulation with two different vibrating properties but for other reasons, may produce a synergistic effect versus either stimulation type alone. For example, when vibrotactile stimulation is combined with ultrasound stimulation, the ultrasound stimulation may be able to relax muscles before or after the vibrotactile stimulation, which can increase the effectiveness versus vibrotactile stimulation alone because the muscles are relaxed rather than tensed between vibrotactile stimulations. For example, when vibrotactile stimulation is combined with optical stimulation (e.g., a tissue-penetrating red laser), the optical stimulation may be able to reach portions of the body that the vibrotactile stimulation cannot, which can increase the effectiveness versus vibrotactile stimulation alone because additional tissues are stimulated and/or some same tissues may be stimulated in a different way to produce a different response.

Figure 12:
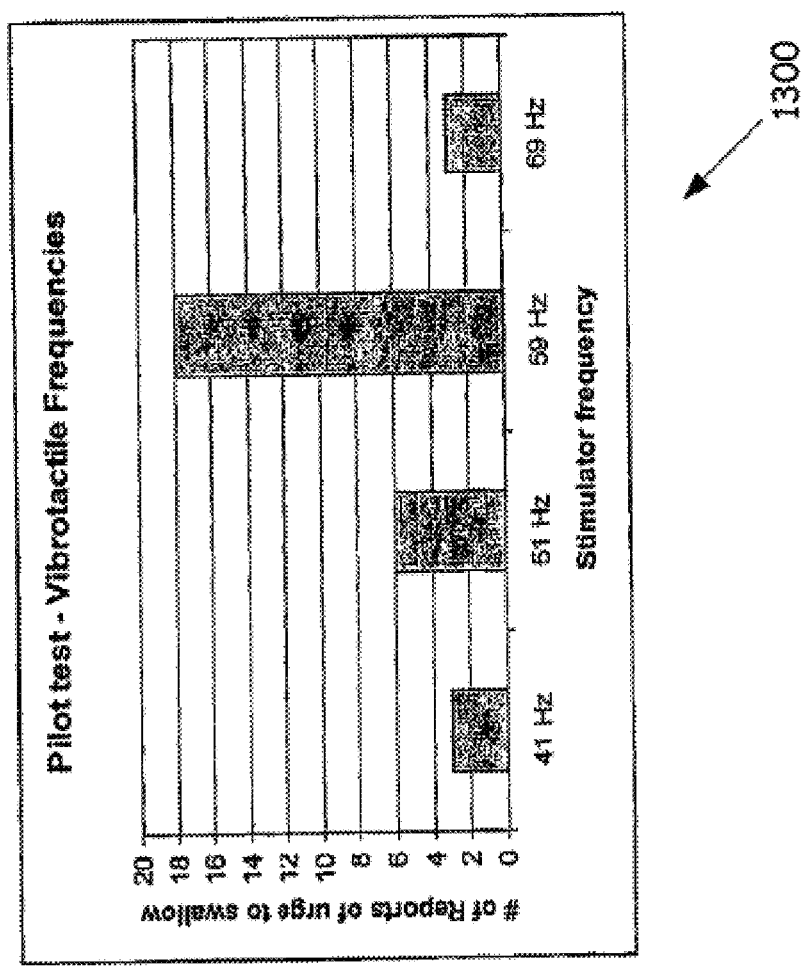
FIG. 12 is a bar chart illustrating efficacy of various vibrotactile frequencies in inducing an urge to swallow.

In some embodiments, vibratory stimulation may be applied at a vibrating frequency of about 1 Hz to about 100 Hz, about 5 Hz to about 70 Hz, about 30 Hz to about 60 Hz, about 50 Hz to about 60 Hz, about 55 Hz to about 60 Hz, or about 58 Hz to about 60 Hz. Certain such frequencies may be useful, for example, for single vibrator applications. FIG. 12 is a bar chart illustrating efficacy of various vibrotactile frequencies in inducing an urge to swallow. In some embodiments, the vibrator produces a sequential wave of pressure across bars (such as 1 to 5 oblong bars) at about 0.5 Hz to about 30 Hz, or about 2 Hz to about 25 Hz, or about 5 Hz to about 10 Hz. In some embodiments, vibratory stimulation may be applied at a first vibrating frequency of about 10 Hz to about 150 Hz, about 25 Hz to about 125 Hz, about 50 Hz to about 90 Hz, about 65 Hz to about 75 Hz, or about 68 Hz to about 72 Hz (e.g., about 70 Hz), and, at least partially simultaneously, at a second vibrating frequency of about 50 Hz to about 200 Hz, about 75 Hz to about 175 Hz, about 90 Hz to about 130 Hz, about 105 Hz to about 115 Hz, or about 108 Hz to about 112 Hz (e.g., about 110 Hz). In some embodiments, vibratory stimulation may be applied at a first vibrating frequency of about 10 Hz to about 100 Hz, about 15 Hz to about 75 Hz, about 20 Hz to about 40 Hz, about 25 Hz to about 35 Hz, or about 28 Hz to about 32 Hz (e.g., about 30 Hz), and, at least partially simultaneously, at a second vibrating frequency of about 30 Hz to about 200 Hz, about 40 Hz to about 110 Hz, about 50 Hz to about 90 Hz, about 65 Hz to about 75 Hz, or about 68 Hz to about 72 Hz (e.g., about 70 Hz). Such frequencies may be useful, for example, for multiple vibrator applications. In some embodiments, the vibrators produce sequential waves of pressure across the same or different bars. In some embodiments, the difference between the vibrating frequencies of multiple stimulators is between about 10 Hz and about 100 Hz, between about 20 Hz and about 60 Hz, between about 30 Hz and about 50 Hz, between about 20 Hz and about 30 Hz, between about 35 Hz and about 45 Hz, between about 38 Hz and about 42 Hz (e.g., about 40 Hz), or between about 23 Hz and about 27 Hz (e.g., about 25 Hz). The amplitude of vibration may be, for example, about 1 micron (µm) to about 2 mm, or about 100 µm to about 1 mm.

In some embodiments, the pressure and/or electrical stimulation is applied at a frequency of about 50 Hz, about 51 Hz, about 52 Hz, about 53 Hz, about 54 Hz, about 55 Hz, about 56 Hz, about 57 Hz, about 58 Hz, about 59 Hz, or about 60 Hz. The pressure may be about 1 pound per square inch (psi) to about 14 psi with rise times of about 2 ms to about 500 ms or rise times between about 4 and about 150 ms. The pressure may be about 0.5 kiloPascals (kPa) to about 8 kPa, about 2 kPa to about 6 kPa, or about 3 kPa to about 5 kPa (e.g., about 4 kPa). Other pressures are also possible. Greater pressure can increase the elicitation of swallowing, but can also lead to increased discomfort. Healthy subjects generally tolerate a pressure of less than about 4 kPa (e.g., about 3 kPa), although a recent subject tolerated about 6 kPa. The pressure may be an adjustable parameter that can be varied or tuned for each subject.

Electrical stimulation, if used, may applied at a rate of 30 Hz at low levels of less than about 2 mA over a small area of 1 cm$^2$ or 25 mA over a large area (about 10 cm$^2$) or greater, or less if the area is smaller (less than about 10 cm$^2$), such as about 0.01 mA to about 10 mA, about 0.1 mA to about 7 mA, about 0.5 mA to about 5 mA, or about 1 mA to about 3 mA to assure that only sensory stimulation is occurring, and that the electrical stimulation does not result in muscle contraction. Levels that do not exceed about 10 mA (e.g., about 7 mA, about 5 mA, about 4 mA, about 3 mA, about 2 mA, and about 1 mA) may be useful in this regard. In some embodiments, electrical stimulation comprises biphasic pulses (e.g., pulses at about 50 microsecond (µs) to about 300 µs) of about 1 mA to about 5 mA current at about 15 Hz to about 60 Hz. When a system or method comprises electrical stimulation, care should be taken to assure that muscle contraction is not occurring, as stimulation of muscles in the throat area pull the hyoid downward and interfere with swallowing.

In some embodiments, the amplitude of the stimulation (measured as energy output or more directly as, e.g., vibration displacement) and/or the rate of the stimulation pulse increases during the swallowing activity. In some embodiments, the duration of stimulation is set to the average measured or expected duration of the subject's swallow (e.g., between about 1 s and about 3 s, between about 1 s and about 2 s, between about 1 s and about 1.5 s). In some embodiments, the stimulation lasts as long as the swallow is perceived to occur (e.g., by a sensor or by the subject). In some embodiments, the stimulation lasts as long as a switch is activated. To inhibit or prevent central adaptation or desensitization to the stimulation, the stimulation should only be turned on by the subject when attempting to swallow and should remain off when the subject is not attempting to swallowing. An exception is the automatic mode described herein, which is not necessarily considered a training mode.

The subject can activate a system stimulates their own throat over the larynx to elicit the reflex swallowing. In some embodiments, the stimulation is vibratory, tactile, pressure, or a combination thereof. In some embodiments, the stimulation is vibrotactile. In some embodiments, the subject controls the stimulation via an actuator in communication with the stimulator. The vibrotactile stimulator can provide substitute sensation to assist with eliciting swallowing while training the subject to volitionally control swallowing to substitute for their loss of reflexive swallowing. Certain systems described herein can train the subject to activate the actuation (e.g., press a button) immediately before wanting to swallow to provide an alternate sensory input via vibrotactile stimulation (or other sensory modalities) to the throat area to enhance volitional control of swallowing.

Swallowing retraining can provide subjects and their caregivers the opportunity to practice volitional swallowing early in the postextubation period. FIG. 12 is graphically depicts conceptualization of events after brain injury. Referring again to FIG. 2, certain neural circuitry is involved when using a hand control 203 to trigger volitional swallowing 204 along with simultaneous sensory stimulation 201 that goes to the cortex 202. This may occur after button press training described herein. Elicitation of the swallowing reflex and safety in swallowing is dependent upon sensory feedback 201 to the brain from sensory mechanoreceptors in the upper airway. If sensory input is withdrawn, subjects feel that they can no longer swallow and are at significant risk of aspiration during swallowing. The neural circuitry enhances cortical motor control 202 of swallowing coincident with substitution of sensory input 203 from stimulation of the throat area to trigger brain stem circuitry to trigger reflexive swallowing 204 simultaneous with volitional swallowing. By practicing motor onset with a device that provides an alternative sensory input to the brain, such as vibrotactile stimulation, the subject can regain volitional swallowing control, readying them to swallow safely first with their own saliva and later to ingest small amounts of food in a controlled volitional fashion. By providing volitional control over swallowing, the subject can substitute voluntary swallowing for their loss of reflexive swallowing.

An automatic timer can be used to stimulate the initiation of swallowing on a periodic basis to inhibit or prevent drooling and/or aspiration of the subject's own secretions. In some embodiments, activation of the stimulator is not dependent upon manual volitional activation by the subject, and can be set to initiate swallowing without a user input at a predetermined or variable interval. For example, the automatic timer can be configured to initiate swallowing of saliva to inhibit or prevent aspiration of secretions from drooling during sleeping. Methods for automatically stimulating swallowing on a regular basis or set interval may comprise applying a vibrotactile stimulator (e.g., comprising one vibrational transducer, two vibrational transducers, or two vibrational transducers with different vibrating frequencies) to an outside surface of the subject's neck substantially over the subject's larynx and configuring an automatic timer to activate the vibrotactile stimulator to induce the swallowing reflex, for example at vibrating frequencies, durations, pressures, etc. described herein. In some embodiments, an onset period of the stimulation comprises about 10 ms to about 1.5 s, about 50 ms to about 750 ms, or about 100 ms to about 500 ms.

In some embodiments, the automatic timer is configured to activate the vibrotactile stimulator once every 3 min to about once every 30 min, once every 2 min to once every 10 min, or once every 1 min to once every 5 min. In some embodiments, the automatic timer is configured to activate the vibrotactile stimulator for a duration of about 10 ms to about 20 s, during which pulsed stimulation is produced for about 200 ms to about 10 s to induce the swallowing reflex. Activation of the vibrotactile stimulator may be pulsed at a particular rate and last for a particular interval to produce vibrations at desired a frequency or frequencies and/or pressure.

The device may comprise a counter and timer system to aid in monitoring a subject's use of the device. For example, the counter and timer system can be used to determine or measure frequency of stimulator activation, including how often the subject uses the device, which mode the subject uses, how long and when the device is stimulated, and the like. The data generated by the counter and timer system can be used, for example, to determine compliance with a training or therapy regime. Such data can be used to modify a treatment or training program and/or can alert caretakers to a risk of drooling or aspiration of secretions due to limited use of the system.

Methods for identifying a subject at risk of aspiration from their own secretions may comprise applying a device to an outside surface of the subject's neck substantially over the subject's larynx, downloading data from the device after a period of use of the device by the subject, and analyzing to data to determine if the subject is at risk of aspiration from their own secretions due to limited use. The subject activates the device to induce volitional swallowing and/or allows the device to function in automatic mode, and the device records the data to allow a health professional to determine if the subject is at risk due to limited use.

Methods for monitoring subject compliance with a training or therapy regime may comprise applying a device to an outside surface of the subject's neck substantially over the subject's larynx, downloading data from the device after a period of use of the device by the subject, and analyzing to data to determine if the subject is in compliance with the training or therapy regime. The subject activates the device to induce volitional swallowing and/or allows the device to function in automatic mode, and the device records the data to allow a health professional to determine if the subject is at risk due to limited use.

For dysphagia treatment, a band may be wrapped around the neck, with an inflatable balloon positioned over the larynx. Upon activation (e.g., pressing a button) by the subject or under orders from the subject, the balloon inflates and puts pressure on the larynx. A control box may set parameters such as the stimulus type, stimulus shape (e.g., wave shape (e.g., sinusoidal, sawtooth, square wave)), stimulus rate (constant or changing over time), stimulation continuousness (e.g., continuous, pulsed), and/or stimulus amplitude (constant or changing over time), and whether the duration would be set or stay for 2 s to 6 s or as long as the button is pressed. In some embodiments, the device that stimulates the substitute site comprises a pressure-applying device that attaches to the body by, for example, a hook-and-loop fastener, strap, rubber band, belt, bandage, garment, ace bandage, wire, string, piezoelectric band or film, and/or combination of these, or by any other method known in the art.

In some embodiments, the stimulating device may include a pressure applying device such as an inflatable tube that inflates to a desired pressure or volume, for example adapted from a blood pressure monitor. A neck wrap may position the pressure applying device to the throat area above the larynx and is adjustable (e.g., via hook-and-loop fastener material or any other adjustable fastener). A small point (e.g., as small as about 0.02 cm$^2$) on the throat over the larynx may be pressed, although larger areas (e.g., about 0.1 cm$^2$ to about 10 cm$^2$, about 0.25 cm$^2$ to about 5 cm$^2$, about 0.5 cm$^2$ to about 2.5 cm$^2$) of any shape may be used. For example, an area may be about a 2 cm$^2$ circle. In some embodiments, at least about 25%, at least about 35%, at least about 50%, at least about 75%, at least about 85%, at least about 90%, at least about 98%, or more of the total pressure (calculated as an integrated sum measurement of pressure times surface area) is placed on the throat over the larynx cartilage, and not over surrounding muscle. In some embodiments, vibratory energy is selectively confined on the throat over the larynx versus the surrounding muscle. In some embodiments, less than about 50%, less than about 25%, less than about 10%, less than about 5%, or even less of the total pressure is applied to neck muscles. In some embodiments, the stimulation may comprise vibration, pressure, thermal (e.g., application of cold and/or heat), and/or low levels of electrical stimulation capable of inducing a sensory stimulus but not high enough to induce muscle contraction, or a combination thereof.

Figure 13:
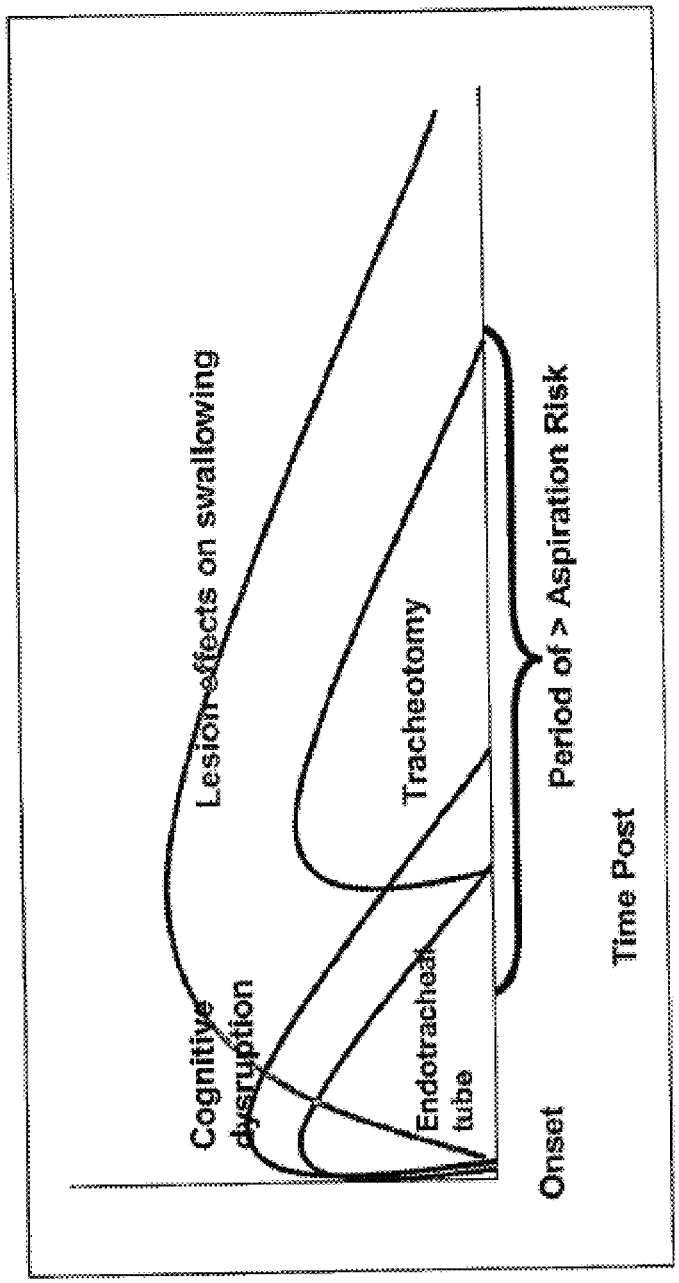
FIG. 13 is graphically depicts conceptualization of events after brain injury.
Figure 15:
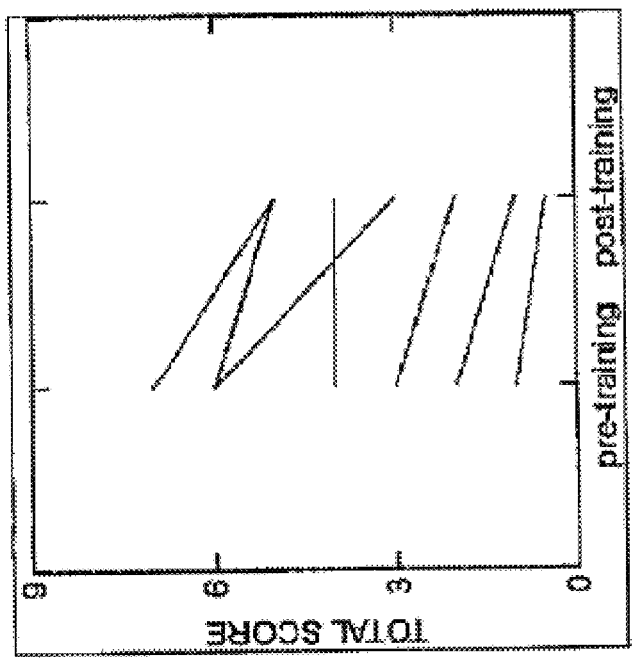
FIG. 15 is a graph showing the change in the NIH safety score for multiple subjects before and after being trained to press a button for coordinating swallowing with intramuscular electrical stimulation.
Figure 14:
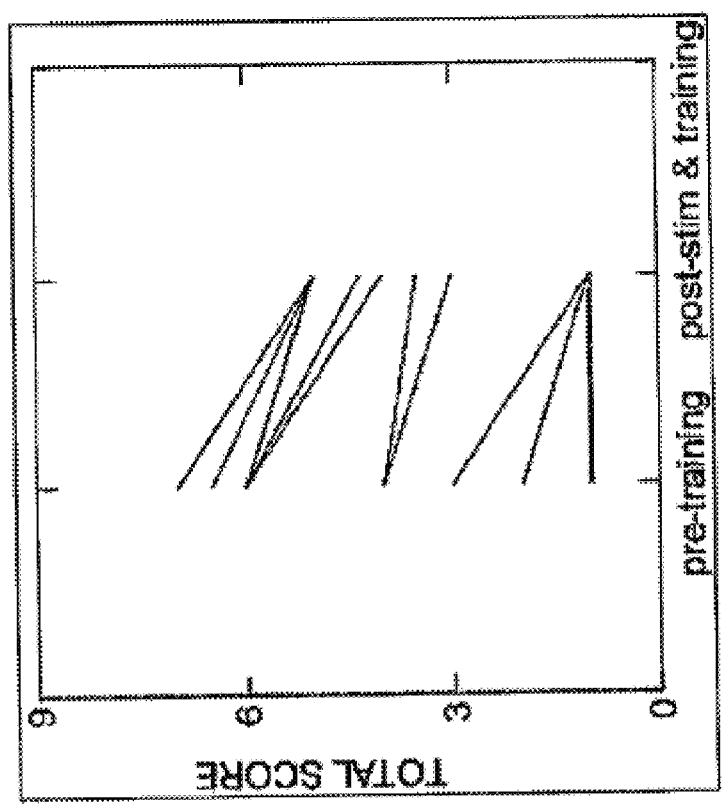
FIG. 14 is a graph showing the change in the degree of risk of aspiration during swallowing for multiple subjects before and after being trained to press a button for coordinating swallowing with intramuscular electrical stimulation. A higher score represents a greater risk of aspiration during swallowing.

Many subjects are intubated to maintain the airway for ventilation, including following loss of consciousness due to brain injury or stroke or following coronary artery bypass graft. An endotracheal tube is extubated as the subject recovers cognitive function, at which point the swallowing reflex may be reduced. FIG. 13 shows a conceptualization of events post brain injury, placing subjects at high risk of aspiration post extubation with tracheotomy due to reduced afferent stimulation in the upper airway and restricted oral intake, limiting return of reflexive swallowing.

There may be several factors that contribute to reduced swallowing reflex associated with intubation. For example, sensory feedback from the upper airway to the brain may be reduced due to changes in the sensory function of the mucosa in the upper airway, possibly as a result of injury to the mucosa by the endotracheal tube, and sensory organs of nerve endings supplying those organs due to the pressure of the endotracheal tube on the mucosa or resultant edema in the upper airway. In some subjects, tissue granulation/ulceration occurs when the endotracheal tube has been in place for prolonged periods (greater than one week). Upon extubation, such subjects often receive a tracheostomy to provide an adequate airway. During the period following extubation, the normal swallowing reflex is reduced, increasing the risk of aspiration.

In addition to loss of the swallowing reflex, when such subjects have a tracheotomy, sensory input to the upper airway may be further reduced because of a lack of air flow through the hypopharynx. In addition, such subjects are often placed on a restricted oral intake to prevent aspiration. As a result of their "nothing per oral" (NPO) status, such subjects are not swallowing and may be fed through a nasogastric tube or long-term by enteric means for several days or weeks. Some or all of these factors can reduce reflexive swallowing. During this period, the methods disclosed herein can enhance volitional swallowing.

Certain devices and methods described herein can provide volitional control for subjects with motor control disorders affecting speech and voice. Persons who stutter usually have difficulty with speech initiation and have speech "blocks" when the subject undergoes a loss of volitional control over the laryngeal muscles in particular. This loss of volitional control is manifested as delay in voluntary initiation of muscle contraction or vocal fold movement or an interference due to chronic laryngeal muscle contractions or sustained vocal fold closure. Several studies have suggested that adults who stutter may have increased thresholds to kinesthetic or vibratory stimulation during speech. The devices and methods disclosed herein can enhance vibratory sensory input to persons who stutter. Recent research has shown that persons who stutter have delays in their onset of vocal fold vibration during speech. Increasing vibrotactile input to the central nervous system in persons who stutter can enhance their volitional control for speech. When a mechanical displacement is applied to the larynx, for example as described herein, it can stimulate proprioceptors in the strap muscles, producing a reflexive sternothyroid muscle contraction. Because extrinsic laryngeal muscles have a high muscle spindle density, stretch or vibratory stimuli applied to the larynx will serve to enhance muscle activity in this region.

Certain devices and methods described herein can provide enhanced volitional control for subjects with spasmodic dysphonia and/or laryngeal dystonia. Spasmodic dysphonia is a laryngeal focal dystonia, which produces voice abnormalities during speech similar to stuttering. These subjects have particular difficulties initiating voicing during speech and are often slow to initiate laryngeal muscle activity and have problems maintaining vocal fold vibration during speech. Many focal dystonias have associated sensory abnormalities, with reduced cortical responses in the somatosensory area including spasmodic dysphonia. By providing increased vibratory stimulation to the laryngeal area, input to the cortical somatosensory region will enhance volitional voice control for speech in persons with spasmodic dysphonia.

In prior methods for treating stuttering, many devices provide altered auditory input, auditory masking, or delayed or frequency-altered feedback of the speaker's speech to them. Examples include the Edinburgh Masker, Delayed Auditory Feedback by Phonic Ear, Pacemaster, the Casa Futura System, Vocaltech, Fluency Master®, and SpeechEasy®. The VocalTech® device includes a vibrator applied to the throat of the user. A microphone picks up the user's voice and then provides both an auditory feedback signal and a vibration to the throat to alter feedback during speech. Certain embodiments described herein differ both in concept and in function from these systems in that the subject presses a button to initiate vibrotactile stimulation to aid their ability to initiate speech/voice onset. In such embodiments, the vibratory signal is initiated before the subject attempts to initiate speech and can aid in their volitional control of speech initiation. The VocalTech® device, by contrast, only detects speech after speech has started and can only be triggered by the subject's own speech. The VocalTech® device utilizes a feedback of the subject's speech and no other inputs such that if the subject is unable to initiate speech and/or voice, the vibratory signal cannot be initiated. The lack of initiation of the vibratory signal is further exacerbated as there is a delay between the onset of the subject's speech and the onset of the vibratory and auditory feedback. The VocalTech® device is therefore unable to enhance the subject's ability to onset speech since the device is dependent upon the speaker being able to initiate speech. Other auditory masking or delayed or frequency altered feedback devices such as SpeechEasy® also alter or delay the speaker's acoustic speech signal and also require that the speaker is able to initiate speech before the feedback can occur. In contrast, certain devices disclosed herein can assist subjects with speech initiation because the vibratory stimulus precedes the subject's speech initiation by enhancing mechanical sensory input to cortical control centers for speech.

In some embodiments, the devices described herein are portable and can be supplied to adults who stutter and persons with dysphonia to provide stimulation before speech to enhance triggering and controlling voice onset and maintenance for speech. The devices can be used in everyday speaking situations. Subjects could purchase the device to use in everyday life to enhance volitional control while speaking.

C. Kits

The present disclosure includes kits that include at least two of: a stimulator adapted to be placed in contact with an affected body part such as the larynx, a control box, an actuator, a power supply, a disposable cover, a container, and instructions for use. The instructions may include at least one instruction corresponding to one or more of the methods disclosed herein. In some embodiments, the stimulator includes at least one pump configured to increase pressure within a chamber. The stimulator may include a pressure, stretch, volume, power, or other sensor to monitor exerted pressure. In some embodiments, the stimulator and/or the control box may include controls, for example, for setting frequency, amplitude, pressure, etc.

EXAMPLES

The present disclosure may be better understood with reference to the following examples. Example 1 demonstrates that low levels of sensory stimulation to the throat area in subjects with severe chronic pharyngeal dysphagia enhances their ability to swallowing safely while high levels of electrical stimulation that activate throat muscles do not enhance swallowing in these subjects. Example 2 demonstrates that two different vibrating properties, such as two different vibrating frequencies, may better elicit swallowing than a single vibrating property.

Example 1

Although surface electrical stimulation has received some attention as an adjunct to swallowing therapy in dysphagia, little is known about the effects of transcutaneous stimulation on swallowing physiology. It has been hypothesized that electrical stimulation may assist swallowing either by augmenting hyolaryngeal elevation or by increasing sensory input to the central nervous system to enhance the elicitation of swallowing.

When electrical stimulation is applied to the skin or oral mucosa at low current levels, it activates the sensory nerve endings in the surface layers, providing sensory feedback to the central nervous system. With increased current amplitude, the electric field may depolarize nerve endings in muscles lying beneath the skin surface and may spread with diminishing density to produce muscle contraction.

When electrodes are placed in the submental region, the current density is greatest at the skin surface and diminishes with depth through the platysma underlying the skin and subcutaneous fat. As the current increases in amplitude, increasingly deeper muscles may be recruited, albeit with less efficiency. Such muscles include the anterior belly of the digastric, which can either lower the mandible or pull the hyoid upward, depending on whether the mouth is held closed. Deeper still are the mylohyoid and geniohyoid muscles, which pull the hyoid bone upward and toward the mandible, respectively. These muscles are much less likely to be activated by surface electrical stimulation because of their greater depth.

When electrodes are placed on the skin overlying the thyroid cartilage in the neck, the current will be greater at the skin, with less intensity to the underlying platysma muscle, with further reduction to the underlying sternohyoid and omohyoid muscles, which pull the hyoid downward and backward towards the sternum. The electrical field strength would be even further diminished if it reaches the deeper thyrohyoid muscle, which brings the larynx and hyoid together and the sternothyroid muscle, which lowers the larynx towards the sternum. Given that the sternohyoid muscle is larger and overlies the thyrohyoid and sternothyroid, high levels of surface electrical stimulation on the neck could pull the hyoid downward, interfering with the ability of certain subjects to raise the larynx toward the hyoid bone as occurs in normal swallowing. In fact, in some healthy volunteers, high intensity surface electrical stimulation reduced swallowing safety as it allowed liquid to enter the vestibule.

In VitalStim® Therapy, electrodes are simultaneously activated over the submental and laryngeal regions on the throat, with the aim of producing a simultaneous contraction of the mylohyoid in the submental region (to elevate the hyoid bone) and the thyrohyoid in the neck (to elevate the larynx to the hyoid bone). However, because these muscles lie deep beneath the anterior belly of the digastric, sternohyoid and omohyoid muscles, simultaneous transcutaneous stimulation with two pairs of electrodes at rest might cause: 1) the hyoid bone to descend in the neck (due to sternohyoid muscle action); 2) the hyoid bone to move posteriorly (due to the omohyoid muscle activity); and 3) the larynx to descend (if current activates either the sternohyoid or stenothyroid muscles), and, in severe chronic dysphagia: 4) when the same array is used at low levels of stimulation just above the sensory threshold, sufficient for sensation but without muscle activation, subjects' swallowing might improve due to sensory facilitation; while 5) at higher levels required for motor stimulation, the descent of the hyoid might interfere with swallowing causing increased penetration and aspiration.

Methods

Participant selection criteria included: chronic stable pharyngeal dysphagia, at risk for aspiration for 6 months or more, a score of 21 or greater on the Mini-Mental State Examination, a severely restricted diet and/or receiving nutrition through enteric feeding, and medically stable at the time of the study. To be included for study, all participants had to demonstrate a risk of aspiration for liquids on videofluoroscopy during the screening portion of the study.

Procedures

Participants were administered informed consent, and had to correctly answer 10 questions to demonstrate that they understood the content of the consent before participating. VitalStim® electrodes and the VitalStim® Dual Channel Unit were used for the study. Two sets of electrodes were used; the top set was placed horizontally in the submental region over the region of the mylohyoid muscle above the hyoid bone. The bottom set was placed on the skin over the thyroid cartilage on either side of the midline over the region of the thyrohyoid muscle medial to the sternocleidomastoid muscle. This electrode array was recommended as effective during certification training. A ball bearing with a diameter of 19 mm was taped to the side of the neck for measurement calibration.

After familiarizing the participant with the device, the sensory threshold, which was the lowest current level at which the participant reported a "tingling" sensation on the skin, was identified. Electrical surface stimulation at the sensory threshold level did not produce movement on videofluoroscopic recordings, and was the lowest level at which participants sensed the electrical stimulation on the skin. Movement was first observed when participants first reported a "tugging" sensation, usually around 7 milliamperes (mA) or 8 mA. The maximum vibrator motor level was the highest current level a participant could tolerate without discomfort during surface electrical stimulation on the neck. The sensory and motor levels were determined independently for each set of electrodes. The VitalStim® device cycles automatically from "on" to "off" to "on" again for 1 second every minute. Because the change in surface electrical stimulation is ramped, this cycling process takes up to 4 s. For the stimulation at rest trials, the participant was told to keep their teeth clenched to prevent jaw opening and the stimulation was simultaneously set at the maximum tolerated levels for both sets of electrodes. When the stimulation duration reached 55 s, videofluoroscopy was turned on and the fluoroscopic image was recorded on S-VHS videotape while the participant was in the resting position, and the device automatically cycled from "on" to "off" and then "on" again. The examiner pressed a button at the time of stimulation offset to place a visible marker on the videotape.

During the videofluoroscopic screening examination, a volume, either a 5 mL or 10 mL of liquid barium bolus, was determined to be more challenging and put a participant at risk of aspiration for use during testing. During testing, between one and three swallows were recorded in each of the following conditions in random order: 1) with no stimulation, 2) with both electrode sets on at the sensory threshold level, and 3) with both sets at the maximum tolerated stimulation level. The surface electrical stimulation remained on before, during, and after the stimulated swallows. The videotaped recordings included an auditory channel for documentation and a frame counter display for identifying when stimulation changed.

Because radiation exposure during this study was administered for research purposes only and was not for necessary medical care, the Radiation Safety Committee limited exposure time per participant for the total study. Therefore, depending on radiation exposure time in each part of the study, only one to three trials per condition were able to be performed in addition to stimulation at rest for each of the participants.

Movement Analysis

The video of each trial was captured off-line using Peak Motus 8, a 2D motion measurement system. The system was equipped with a video capture board at ~60 fields/s (~30 frames/s) and a frame size of 608×456 pixels. The radius of the ball bearing (9.5 mm) was used for all measurement calibrations in the horizontal and vertical directions. An investigator used a cursor to identify the points on the most anterior-inferior corner of the second and fourth vertebra on each video frame and a straight line was drawn between these two points to define the y axis. When either the second or fourth vertebra was not visible, the bottom anterior-inferior corner of the first and third vertebrae were used in the same fashion. A line perpendicular to the y axis at the anterior-inferior corner of the lower vertebra served as the x axis. The x and y coordinates for all points were determined in mm relative to the anterior-inferior corner of the second vertebra serving as the origin with anterior and superior points being positive and posterior and inferior points being negative for direction of movement of the hyoid. Four points were marked for each frame, the anterior-inferior points of the two interspersed vertebrae, the anterior inferior point of the hyoid bone and the most posterior and superior point in the subglottal air column (to track the position of the larynx).

The time series plots of the x and y points of the hyoid bone and the y coordinate of the larynx were exported from Peak Modus into Microsoft Excel and then into Systat 11 (available from Systat Software, Inc. of Richmond, Calif.) for analysis. The frame when the stimulation cycled from "on" to "off" was added to the file and used to sort measures into stimulation "on" and stimulation "off." All of the position data were then corrected to place the starting position at zero on both the x and y axes for each subject and then the mean hyoid (x,y) and larynx (y) positions were computed for the stimulation "on" and stimulation "off" conditions for each subject.

Dysphagia Ratings

Four experienced certified speech pathologists initially examined the screening videotapes of randomly selected subjects to decide on a rating system. After assessing several swallows with the Pen-Asp, it was noted that many of the participants who were on enteric feeding because of their risk of aspiration could score within the normal range, a score of 1 on this scale. This occurred when no penetration or aspiration occurred, even though there was severe residual pooling in the pyriform sinuses and none of the bolus entered the esophagus. These participants regurgitated any residual material back into the mouth after a trial, not swallowing any of the liquid but scoring as normal because no material entered the airway. Because scores of 1 on the Pen-Asp scale were at ceiling (normal) and would not allow measurement of improvement, this scale could only measure a worsening in swallowing in these subjects. Therefore, another scale was developed that did not have a ceiling effect.

The NIH Swallowing Safety Scale (SSS) captured the abnormalities seen in this subject group, which involved pooling and a lack of esophageal entry with and without penetration and aspiration. When scoring a swallow, a score of 1 was assigned for the occurrence of each the following abnormalities: pooling in the vallecula, penetration into the vestibule from the hypopharynx, pooling in the pyriform, and back up penetration from the pyriform into the laryngeal vestibule. The amount of the bolus material entering and clearing from the upper esophagus was rated as 3 if none entered, 2 if a minimal amount entered, 1 if a moderate amount entered and 0 if all of the bolus was cleared through the upper esophagus. In addition, the total number of aspirations in each swallowing sample were counted. Only normal swallows received a total of 0 on this scale and the maximum score could reach as high as 15 depending upon the number of aspirations or other abnormalities in bolus flow that occurred in a single swallow.

All four speech pathologists viewed each videofluoroscopic recording without knowledge of condition and came to a consensus on all noted behaviors and the Pen-Asp rating before assigning the scores. After repeating ratings on 21 trials to establish reliability, differences in ratings of the same swallow were noted and a set of uniform rules were developed to be followed in assigning scores. These rules were subsequently used to assign ratings to each of the trials in this study. Another set of 18 trials was then repeated to determine the measurement reliability.

Statistical Analyses

To determine the reliability of the position measures, two examiners measured the position for the hyoid on the x and y axes and larynx on the y axis on each frame and then computed means for each during both the stimulated and non-stimulated conditions on 4 of the 10 subjects. The output of the General Linear Model Systat 11 was used to calculate the mean square differences for the within and between subject factors. The Intraclass Correlation Coefficient (ICC) was computed by taking the mean square difference between subjects and subtracting the mean square difference within subjects and then dividing the result by the sum of the mean square difference between subjects and the mean square difference within subjects.

To determine the reliability of the ratings made using the Pen-Asp scale and the NIH-SSS, ICCs were computed between the two sets of ratings on each scale from the first 21 trials that were reanalyzed. To identify the items that were unreliable, Cohen's Kappa was computed for the two sets of ratings of each component item of the NIH-SSS using Systat 11. After developing rules for scoring those items that had low reliability, ICCs were computed on the second set of repeated ratings for both the Pen-Asp Scale and the NIH-SSS.

To address the first hypothesis that the hyoid bone would descend in the neck with maximal levels of stimulation at rest, a one-sample directional t-test was used to test for a lowering of the hyoid bone on the y axis between "off" and "on" stimulation. To address the second hypothesis that the hyoid bone would move posteriorly, a one-sample directional t-test was used to test for a retraction of the hyoid bone on the x axis in the "off" and "on" stimulation conditions within subjects. To determine if the larynx descended during stimulation, a one-sample directional t-test was used to test for a lowering of the subglottal air column between the two conditions.

To determine if swallowing improved due to sensory levels of stimulation, one-sample directional t-tests were used to test participants' mean changes in ratings between non-stimulated swallows and stimulated swallows within participants on the Pen-Asp scale and the NIH-SSS with a Bonferroni corrected p value of 0.05/2=0.025. To determine if swallowing worsened during maximum levels of motor stimulation, one-sample directional t-tests were used to test participants' mean changes in ratings between non-stimulated swallows and stimulated swallows within participants on the Pen-Asp Scale and the NIH-SSS with a Bonferroni corrected p value of 0.05/2=0.025. Pearson correlation coefficients using a Bonferroni corrected p value of 0.025 for statistical significance were computed between both the participant's mean initial severity on the Pen-Asp scale and the NIH-SSS and changes in mean ratings during the sensory stimulation to determine if participant characteristics predicted the degree of benefit. Similarly, Pearson correlation coefficients were computed between the extent to which the hyoid was pulled down in the neck during stimulation at rest and the change in participants' mean ratings for swallowing on the Pen-Asp scale and the NIH-SSS using a Bonferroni corrected p value of 0.025 for statistical significance.

Results

1. Participants

All 11 participants had chronic long-standing dysphagia (Table 1). Their disorder was either subsequent to a CVA in six (>6 months post), post craniotomy for a benign tumor in two (2 and 4 years post), or post traumatic brain injury in two (2 and 3 years post). Only one subject had a chronic progressive neurological disease, Parkinson disease, of >20 years with dysphagia for more than 2 years duration.

Ten of the 11 participants participated in the stimulation at rest trials; one did not because of time constraints. During swallow stimulation trials, one of the participants had severe aspiration on an initial swallowing trial and for safety reasons the study was discontinued for that participant. Therefore, ten participants were included in the motor stimulation swallow trials. Because of time constraints, two of the participants did not participate in the low sensory levels of stimulation, leaving 8 participants in the study.

2. Measurement Reliability

The ICC for the movement of the hyoid bone on the y axis in the on and off stimulation conditions were 0.99 and 0.94, respectively, and for hyoid movement on the x axis in the on and off stimulation conditions were 0.94 and 0.87, respectively. The ICCs for the larynx on the y axis in the stimulation "on" and "off" positions were 0.58 and 0.66, respectively, indicating much less reliability on these measures. Because the movement of the larynx was extremely small, ranging from a mean position of 0.4 mm in the stimulation "on" to 0.18 mm in the "off" condition, measurement variability contributed to the variance on this measure.

3. Movement Induced by Stimulation at Rest

Figure 16:
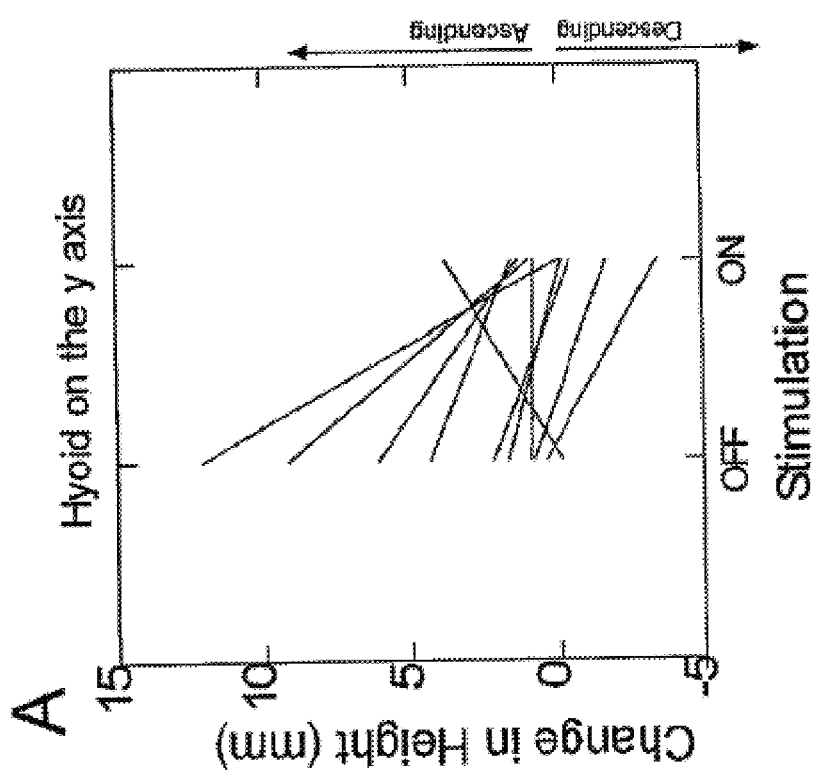
FIG. 16 is a graph showing mean values for hyoid position for each subject during OFF and ON electrical surface stimulation conditions after training.
Figure 17:
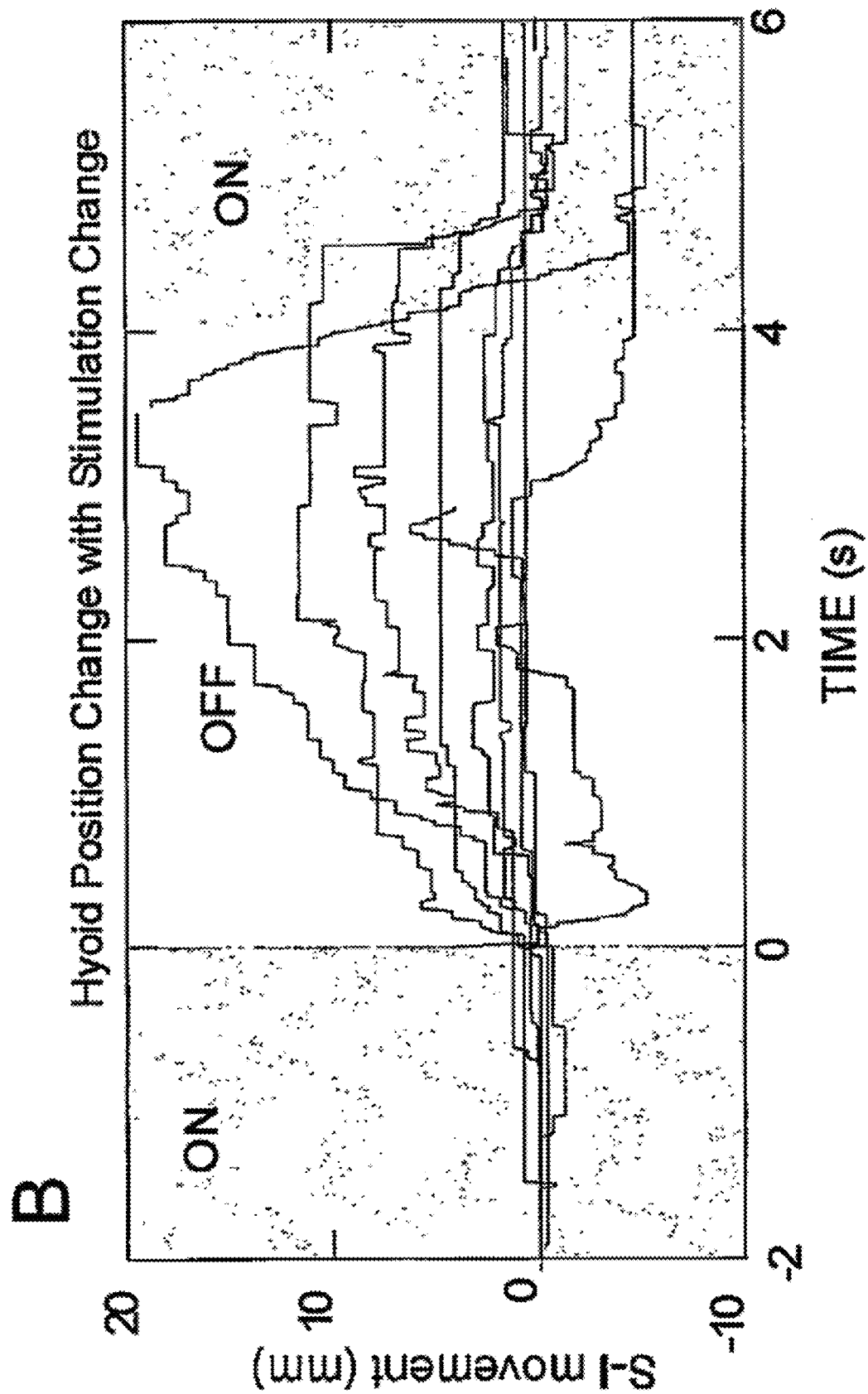
FIG. 17 depicts traces of hyoid position during electrical surface stimulation ON, then stimulation OFF, followed by stimulation ON for each subject.

To address the first hypotheses, a one-tailed directional t-test comparing the mean position between "off" and "on" stimulation conditions demonstrated a significant lowering of the hyoid position on the y axis (f=−2.523, o7=9, p=0.016) (see FIG. 16). In FIG. 17, the individual tracings of hyoid movement in each of the subjects is shown when the stimulator is turned "ON" and then "OFF" and then "ON" again, showing elevation of the hyoid bone when the stimulator is turned "OFF." High levels of electrical stimulation on the throat area lower the hyoid bone when stimulation is "ON." The hyoid is only able to return to a normal position in the neck when stimulation is "OFF." Because of this action, high motor levels of electrical stimulation interfere with the usual elevation of the hyoid bone, which is required for swallowing.

To address the second hypothesis that the hyoid bone would move posteriorly with stimulation at rest, a directional t-test comparing the mean positions in the "OFF" and "ON" stimulation conditions within subjects was not significant (P=−0.102, αf/=9, p=0.460). Similarly, a directional t-test found no descent in laryngeal position on the y axis during stimulation (£=0.696, d/=9, p=0.748).

Figure 21:
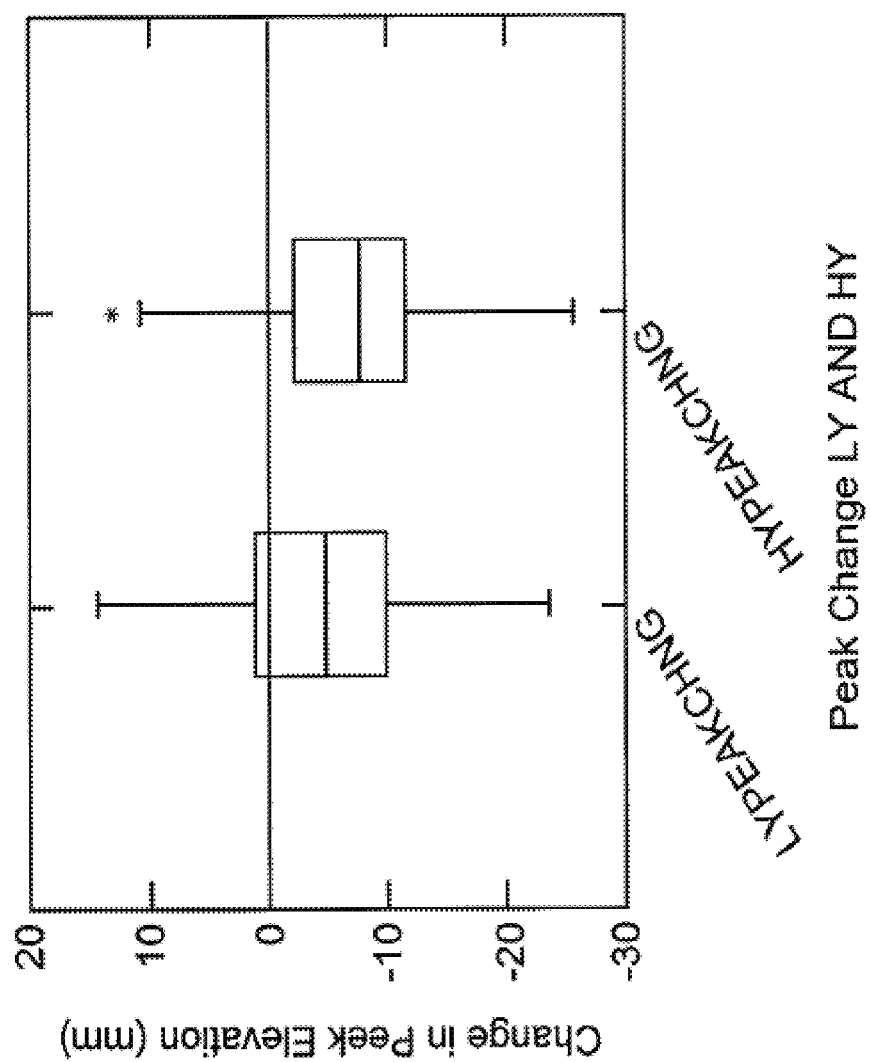
FIG. 21 is a plot of measured peak elevation of the larynx (LYPEAKCHNG) and the peak elevation of the hyoid bone during swallowing (HYPEAKCHNG) in normal subjects with electrical surface stimulation.

FIG. 21 shows that motor levels of surface electrical stimulation (e.g., neuromuscular 8 mA or greater) can reduce hyolaryngeal elevation during swallowing in healthy adults.

4. Reliability of Ratings on the Pen-Asp and NIH SSS

After the first set of 21 repeated ratings, the ICC was 0.965 on the PenAsp scale and 0.764 on the NIH-SSS. Because of concerns about the reliability of the NIH-SSS, more detailed judging rules were implemented for each item where disagreement occurred. A second set of 18 reliability measures using the new judging rules resulted in an ICC for the NIH-SSS that was 0.925, demonstrating adequate reliability when using the scale once the judging rules were developed and implemented.

5. Effects of Low Sensory Stimulation Levels During Swallowing

Figure 18:
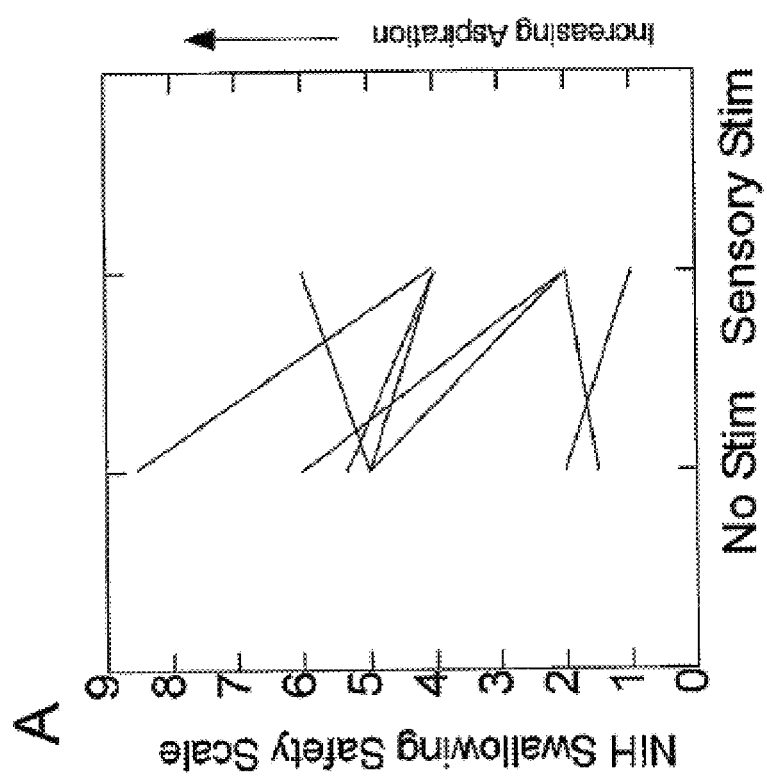
FIG. 18 is a graph showing the change in the NIH swallowing safety score for multiple subjects showing the difference in aspiration during swallowing without stimulation versus swallowing with electrical surface stimulation.

Due to time constraints, only eight of the ten participants completed the sensory condition. To address the fourth hypothesis that swallowing improved with sensory levels of stimulation, one-sample directional t-tests were computed to compare mean change in ratings between non-stimulated swallows and stimulated swallows within participants. The results were not significant on the Pen-Asp Scale (£=0.336, cf/=7, p=0.373), but were significant on the NIH-SSS (.=0.2355, df=7, p=0.025) using a Bonferroni corrected p value of 0.05/2=0.025. FIG. 18 is a graph showing the change in the NIH-SSS for multiple subjects showing the difference in aspiration during swallowing without stimulation versus swallowing with low level electrical stimulation at approximately 2 milliamps (mA) applied on the throat. Sensory levels of stimulation can enhance swallowing safety. Six of the eight of the participants showed a reduction on the NIH-SSS with sensory stimulation during swallowing while five of the eight participants showed a reduction on the Pen-Asp scale.

6. Effects of Motor Stimulation Levels During Swallowing

Figure 20:
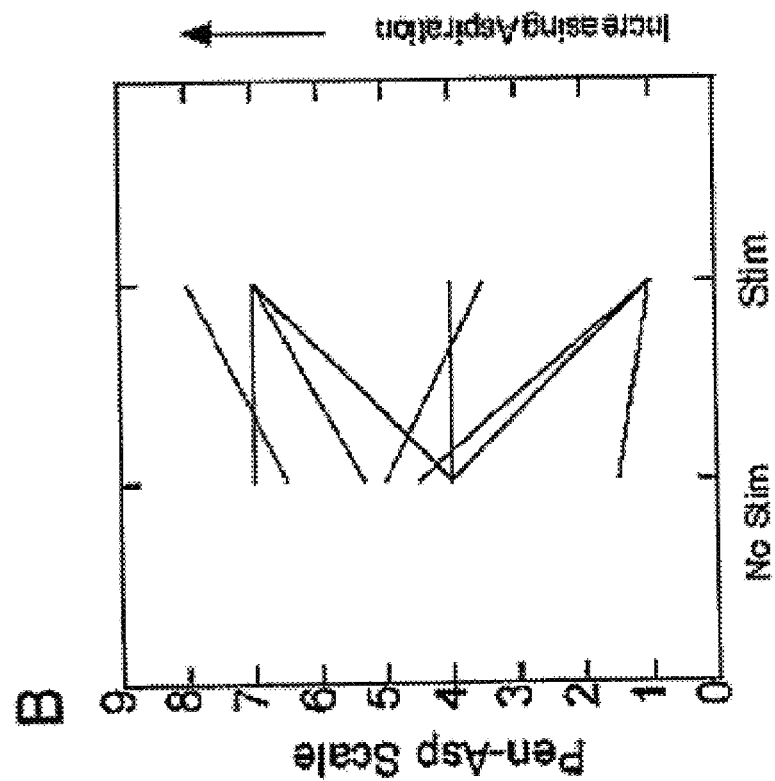
FIG. 20 is a line graph showing the change in the Rosenbek Penetration-Aspiration Scale (Pen-Asp) scale for multiple subjects showing the difference during swallowing with stimulation versus swallowing without electrical surface stimulation.
Figure 19:
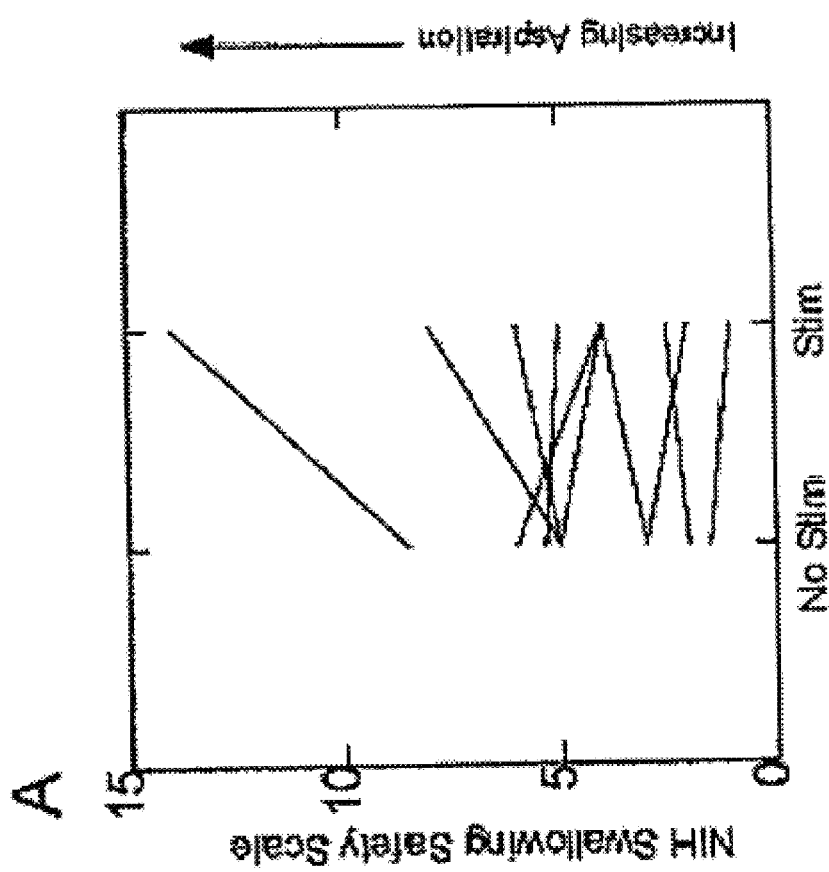
FIG. 19 is another graph showing the change in the NIH swallowing safety score for multiple subjects showing the difference in aspiration during swallowing without stimulation versus swallowing with electrical surface stimulation.

To address the fifth hypothesis that the risk for aspiration and swallowing safety worsened during stimulation, one-sample directional t-tests were computed to examine mean change in ratings between non-stimulated swallows and stimulated swallows within participants. The result was not significant on either the Pen-Asp scale (/=0.363, d/=9, p=0.637) or on the NIH-SSS (/=−0.881, d/=9, p=0.201) at a Bonferroni corrected p value of 0.05/2=0.025. On the NIH-SSS scale, five of the ten participants had increased risk with motor levels of stimulation (FIG. 19), while on the Pen-Asp equal numbers of participants increased or decreased with motor levels of stimulation (FIG. 20). FIG. 19 is auto scaled to the range of the data in the condition. Therefore FIG. 19 is on a larger scale than FIG. 20. FIG. 19 shows that high motor levels of electrical stimulation (>8 mA) do not benefit swallowing in some subjects with swallowing disorders. FIG. 20 is auto scaled to the range of the data in the condition. Therefore, FIG. 16 is on a larger scale than FIG. 20. FIG. 20 shows that high motor levels (>8 mA) of stimulation do not benefit swallowing.

7. Relationship Between Severity of Dysphagia and Changes in Swallowing with Stimulation The Pearson correlation coefficient between participants' initial severity on the Pen-Asp scale and change in swallowing with sensory stimulation was not significant (/=0.142, p=0.737). Similarly, participants' initial severity and change in swallowing with sensory stimulation on the NIH-SSS (/=0.701, p=0.053) was not significant using a Bonferroni corrected a value of 0.025 for statistical significance. A Pearson correlation coefficient between both the participants' initial severity on the Pen-Asp scale and change in swallowing with motor stimulation was not significant (/=−0.501, p=0.140), nor was the correlation between participants' initial severity on the NIH-SSS and change in swallowing with motor stimulation (/=−0.190, p=0.599), using a Bonferroni corrected a value of 0.025 for statistical significance.

8. Relationship of Movement During Stimulation at Rest with Changes in Swallowing with Stimulation Pearson correlation coefficients were computed between the extent to which the hyoid was pulled down in the neck during stimulation at rest and the change in swallowing on the Pen-Asp and the NIH-SSS using a Bonferroni corrected o value of 0.025 for statistical significance. No significant relationship was found between the degree of improvement on the NIH-SSS and the degree to which the hyoid bone was depressed during motor levels of stimulation at rest (r=−0.388, n=9, P=0.302). The improvement in the Pen-Asp scale during motor stimulation was significantly inversely related to the degree to which the hyoid bone was depressed during motor levels of stimulation at rest (r=−0.828, n=9, p=0.006). The relationship demonstrated that those with the greatest hyoid depression at rest had the greatest reduction on the Pen-Asp scale during motor levels of stimulation while swallowing.

DISCUSSION

One purpose of this study was to determine the physiological effects of surface electrical stimulation on the position of the hyoid and larynx in the neck. It was predicted that when both the submental and laryngeal electrode pairs were stimulating at the participants' maximal tolerated levels, the hyoid bone would be pulled downward, most likely due to stimulation of the sternohyoid muscle. The data supported this hypothesis; as all but two of the participants had depression of the hyoid bone by as much as 5 mm to 10 mm during stimulation at rest. It was also predicted that the hyoid bone might be pulled posteriorly; however, limited anterior-posterior movement occurred in the hyoid bone. Three participants had hyoid anterior movement, by as much as 5 mm in one case, while the others had minimal movement in the posterior direction. Whereas minimal ascending movement (2-3 mm) occurred in the larynx in two participants, none of the other participants experienced any appreciable laryngeal movement and the 2-3 mm changes were potentially due to measurement variation. To summarize these findings, the only appreciable motoric effects of surface electrical stimulation was to cause the hyoid bone to descend in the neck, producing movement in the opposite direction from that required for swallowing.

These results suggest that when surface stimulation was applied to the neck at rest, stimulation was either too weak or not deep enough to stimulate axons innervating the muscles that produce hyoid and laryngeal elevation such as the mylohyoid and the thyrohyoid muscles respectively. No change in laryngeal position was observed with surface stimulation at rest.

Another purpose of this study was to determine the immediate effects of surface stimulation on swallowing in participants with chronic pharyngeal dysphagia. Based on previous use of sensory stimulation in the oral and pharyngeal cavities to augment subjects' volitional control of swallowing, sensory levels of electrical stimulation just above the participants' sensory threshold were compared for detecting a tingling sensation on the skin, and showed a significant improvement during swallowing on the NIH-SSS scale (FIG. 18). The improvement on the NIH-SSS tended to be related to higher initial scores; that is the more severely affected subjects were those who had the greatest improvement with stimulation. Because the NIH-SSS captures pharyngeal pooling and failed esophageal entry in contrast with the Pen-Asp scale, which only measures aspiration and penetration, sensory stimulation may be somewhat helpful in those patients who have reduced ability to clear the bolus from the airway.

Based on the expected lowering of the hyoid with motor levels of stimulation, it was hypothesized that the group would have increased penetration and aspiration during swallowing with motor stimulation. No group change in aspiration was noted on either scale with motor levels of stimulation. When the degree of improvement on the Pen-Asp scale with motor levels of stimulation was examined relative to the degree of hyoid depression, an unexpected relationship indicated that subjects with the greatest hyoid depression during motor levels of stimulation at rest had the greatest improvement during swallowing with the same levels of stimulation. When the hyoid was depressed with stimulation, a subject probably experienced a greater resistance to hyolaryngeal elevation during swallowing. Perhaps those subjects who felt a greater downward pull on the hyoid, when stimulation was turned on at maximal levels, made a greater effort to elevate the hyolaryngeal complex when swallowing in an attempt to overcome the effects of the stimulation. It could also be the case that those subjects who had greater residual power in their hyolaryngeal muscles would have not only experienced greater hyoid descent with stimulation but could also have greater residual power that they could recruit for hyolaryngeal elevation to counteract the stimulation induced descent during swallowing.

This study also addressed the immediate physiological effects of the use of surface electrical stimulation at rest and during swallowing. This study suggests that electrical stimulation should be used judiciously dependent upon a subject's type and degree of difficulty with swallowing. In those subjects who already have some ability to raise the hyolaryngeal complex, hyoid depression with stimulation may serve as "resistance" during therapy. On the other hand, if a subject is unable to produce any hyolaryngeal elevation, and therefore would not be able to resist the hyoid depression induced by stimulation, stimulation might put such a subject at greater risk of aspiration as the hyolaryngeal complex is held down during swallowing. This may have occurred in some of the more severely affected subjects who increased in severity on the Pen-Asp and NIH-SSS with motor levels of stimulation, while those less impaired did not change (FIGS. 19 and 20).

In this study, both submental and laryngeal pairs of electrodes were used simultaneously, as is recommended for VitalStim® Therapy. It is likely that the simultaneous stimulation resulted in hyoid lowering because the stronger stimulation to the more superficial and larger sternohyoid and sternothyroid muscles overcame any action that might have been induced by stimulation of the mylohyoid muscle in the submental region or the thyrohyoid muscle beneath the sternohyoid in the throat region. Some have proposed using submental stimulation alone to activate the anterior belly of the digastric and the mylohyoid muscles to pull the hyoid bone upward. However, elevation of the hyoid bone without simultaneous stimulation of the thyrohyoid to raise the larynx would leave the larynx down resulting in further opening of the vestibule and increased risk of aspiration. Only if the mylohyoid and thyrohyoid muscles are activated together, without contraction of the sternohyoid, would both the hyoid and larynx be raised together as has previously been shown with intramuscular stimulation. This cannot be achieved using surface electrical stimulation because the larger sternohyoid muscle overlies the thyrohyoid and pulls the hyoid downward.

The finding that the group as a whole improved with sensory levels of stimulation alone on the Pen-Asp scale was unexpected. Previous research has shown that stimulation of the anterior and posterior faucial pillars was most effective stimulation for eliciting a swallow reflex in normal persons. Although not studied physiologically, stroking the throat region is known to assist with the spontaneous elicitation of swallowing in infants and some mammals. Stimulation of either the glossopharyngeal or the superior laryngeal nerves has been shown to elicit swallowing in animals and bilateral chemical blockade of the superior laryngeal nerves disrupts swallowing in normal humans. It has not been observed that sensory stimulation to the surface of the throat would reflexively trigger a swallow in adults; however, sensory levels of electrical stimulation on the skin in the throat may facilitate volitional triggering of swallowing in dysphagia. These results suggest that low levels of electrical stimulation on the skin might be beneficial in some subjects. Because such low levels of electrical stimulation were not observed to induce hyoid depression, it was posited that none of the subjects would be put at increased risk for aspiration using lower sensory levels of stimulation. Before surface electrical stimulation is used, the subjects should be carefully screened to determine whether they would be placed at increased risk of aspiration with a procedure that lowers the hyoid.

TABLE 1

PARTICIPANT CHARACTERISTICS AND SURFACE ELECTRICAL STIMULATION LEVELS

| Subject | Sex | Age | Etiology | Time post onset (years) | Status | Sensory Threshold Upper/Lower Electrode (mA) | Motor Threshold Upper/Lower Electrode (mA) |
|---|---|---|---|---|---|---|---|
| 1. | M | 66 | hemorrhage in veterbrobasilar circulation | 2.5 | PEG, bilateral sensory loss, pooling, previous aspiration pneumonia | 3.5/2.0 | 8.0/8.0 |

TABLE 1-continued

PARTICIPANT CHARACTERISTICS AND SURFACE ELECTRICAL STIMULATION LEVELS

| Subject | Sex | Age | Etiology | Time post onset (years) | Status | Sensory Threshold Upper/Lower Electrode (mA) | Motor Threshold Upper/Lower Electrode (mA) |
|---|---|---|---|---|---|---|---|
| 2. | M | 66 | Parkinson disease | 20 years duration, Severe dysphagia 2+ years | PEG for 2 years, swallowed own secretions Recurrent pneumonias | 6.0/2.5 | 10.0/10.0 |
| 3. | M | 76 | Stroke | 1 | PEG unable to handle secretions Aspriation pneumonia X 3, normal sensation | 4.0/2.0 | 14/7.0 |
| 4. | M | 78 | Brain stem stroke | 5 | PEG, frequent aspiration pneumonias, sever reductions in UES relaxation, normal sensation | 7.0/7.0 | 14/14 |
| 5. | F | 47 | Left occipital and brain stem stroke | 3 | PEG, unable to handle secretions Bilateral sensory loss | 3.0/4.0 | 10/10 |
| 6. | M | 25 | closed brain surgery | 2 | Aspirations on liquids, bilateral sensory loss | 3.5/6.0 | 16.6/13.0 |
| 7. | M | 48 | Cerebellar hemorrhage with craniotomy | 2 | PEG, Unable to handle secretions, aspiration pneumonia, pooling, Normal sensation | 3.0/2.5 | 18.0/18.0 |
| 8. | F | 44 | Subarchnoid hemorrhage left vertebral artery | 2 | Tracheostomy PEG tube Normal sensation bilateral Pooling of secretions | 4.0/2.0 | 12.5/9.5 |
| 9. | M | 45 | Traumatic brain injury | 3 | Chokes on saliva, eats soft foods, drooling, Bilateral sensory loss | 3.0/4.0 | 18.0/16.0 |
| 10. | M | 61 | Left hemisphere stroke | .5 | PEG, Inable to handle secretions, Normal sensation on left, pooling, BOTOX ® in UES | 1.5/4.0 | 13.0/13.0 |
| 11. | M | 47 | Craniotomy for brain stem tumor | 4 | Severe aspiration, multiple aspiration pneumonias Bilateral sensory loss | 1.5/1.5* | 14/18 |

*Couldn't study effects of either sensory or motor stimulation during swallowing due to severe aspiration.

Example 2

Parameters

Participant selection criteria included healthy volunteers at the time of the study (e.g., having no difficulty swallowing). Ten healthy volunteers participated. Two subjects had incomplete data and had to be deleted from the statistical analyses. Eight total conditions were compared: 2 control conditions and 6 stimulation conditions. No stimulation was applied during the 2 control conditions. The 6 stimulation conditions included: (1) 30 Hz continuous vibrator motor; (2) 70 Hz continuous vibrator motor; (3) 110 Hz continuous vibrator motor; (4) 150 Hz continuous vibrator motor; (5) 70 Hz and 110 Hz hybrid continuous vibrator motors; and (6) 70 Hz and 110 Hz hybrid pulsed (4 Hz) vibrator motors. The conditions were randomized across subjects. Each condition lasted 10 minutes containing 17 stimulation periods.

Statistical Analysis

The number of swallows was measured during the stimulation period and during intervals between the stimulation periods. Subjects swallow at different rates, so results between conditions were compared within each subject. For each condition, including control conditions, and for each subject, the average number of swallows during stimulation periods and the average number of swallows during intervals between stimulation periods were computed.

Results

Figure 22:
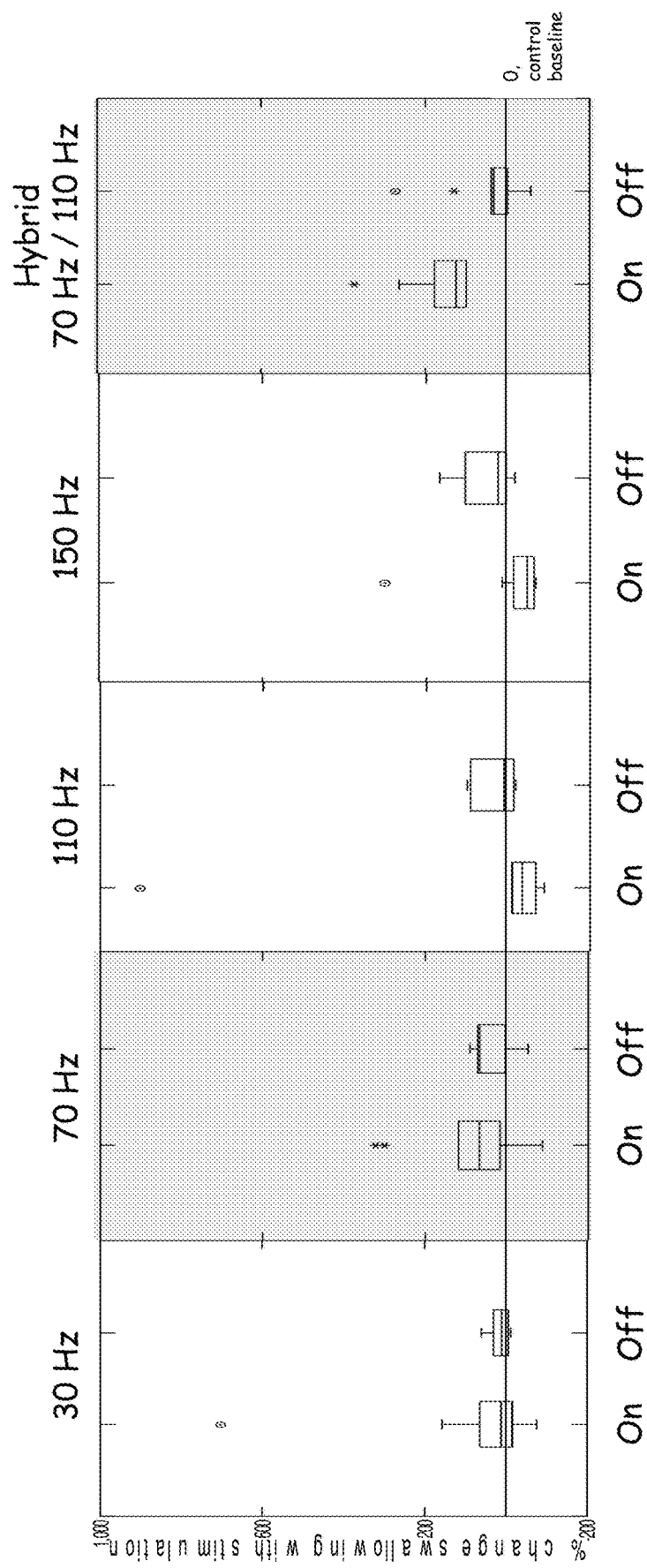
FIG. 22 is a side-by-side comparison of plots of vibrotactile stimulation under various conditions compared to control conditions.

FIG. 22 is a side-by-side comparison of plots of vibrotactile stimulation under various conditions compared to control conditions. The boxes show the range of average swallows in the subjects, with the horizontal line through the boxes being the median of those averages. The effects of stimulation on swallowing differed between conditions ($p<0.001$). Versus control conditions, stimulation during Condition 1 (30 Hz continuous vibrator motor) increased the average number of swallows, stimulation during Condition 2 (70 Hz continuous vibrator motor) increased the average number of swallows, stimulation during Condition 3 (110 Hz continuous vibrator motor) decreased the average number of swallows, stimulation during Condition 4 (150 Hz continuous vibrator motor) decreased the average number of swallows, and stimulation during Condition 5 (70 Hz and 110 Hz continuous vibrator motors) increased the average number of swallows. Swallowing was more frequent during Condition 5 than during Conditions 1, 3, and 4 (p<0.004). The averages between Condition 2 and Condition 5 were somewhat similar, but Condition 5 was higher and also resulted in fewer subjects having less response (e.g., every subject experienced at least a 100% increase in swallowing during stimulation), while Condition 2 resulted in a spectrum of responses across the subjects from fairly ineffective to very effective.

Figure 23:
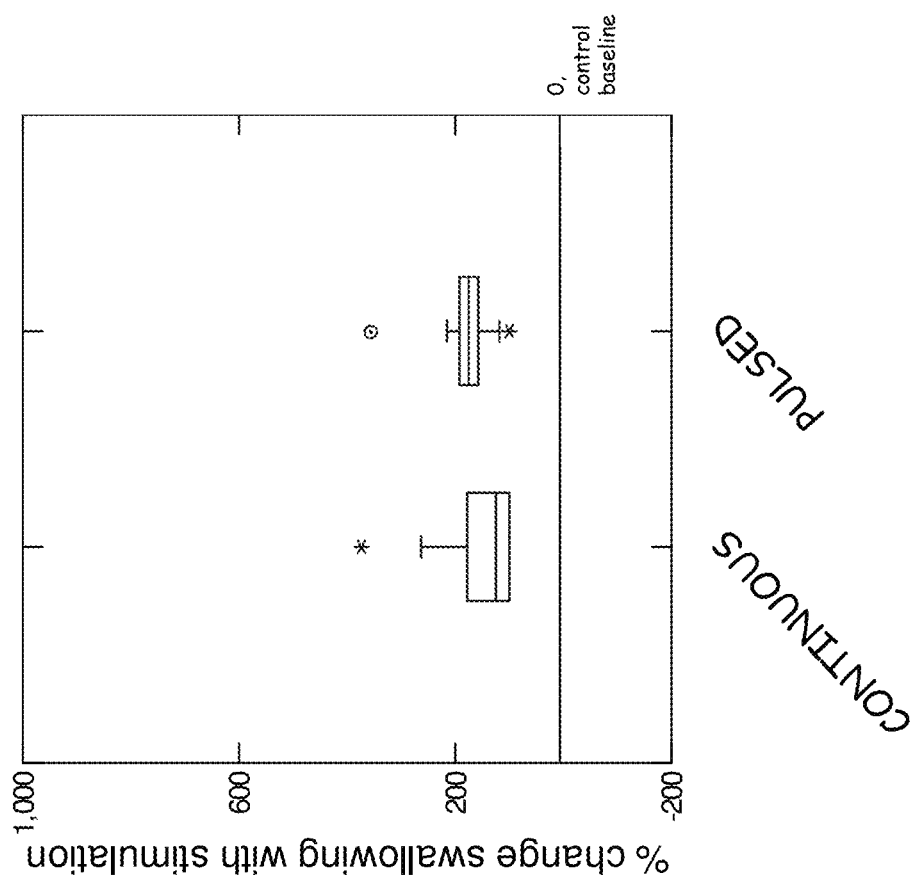
FIG. 23 is a plot of measured continuous vibrotactile stimulation and pulsed hybrid vibrotactile stimulation in normal volunteers.

FIG. 23 is a plot of measured continuous vibrotactile stimulation and pulsed hybrid vibrotactile stimulation in normal volunteers. The boxes show the range of average swallows between the subjects, with the horizontal line though the boxes being the average of those averages. The effects of stimulation on swallowing differed between continuous and pulsed conditions. Versus control conditions, stimulation during Condition 5 (70 Hz and 110 Hz continuous vibrator motors) increased the average number of swallows, and stimulation during Condition 6 (70 Hz and 110 Hz pulsed at 4 Hz) increased the average number of swallows. The averages between Condition 5 and Condition 6 were somewhat similar.

Figure 24:
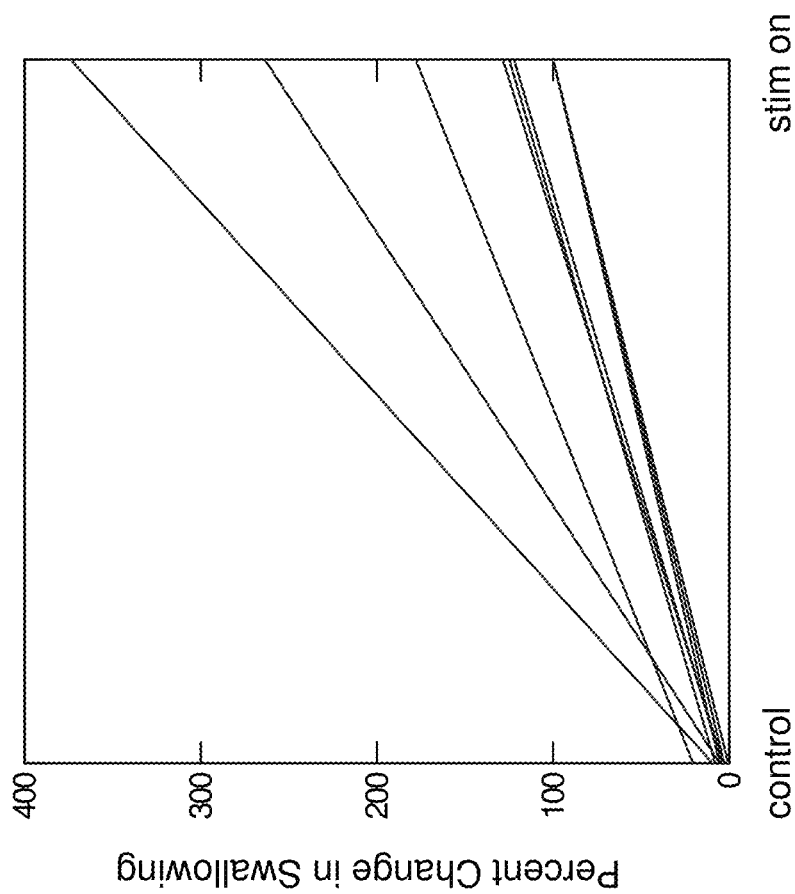
FIG. 24 shows a percent change in rate of swallowing for healthy subjects between control and when hybrid stimulation is applied.

FIG. 24 shows a percent change in rate of swallowing for healthy subjects between control and when hybrid stimulation is applied. The hybrid stimulation included a first vibrating frequency of about 70 Hz and a second vibrating frequency of about 110 Hz. Each subject experienced at least a 100% increase in the rate of swallowing versus control, with some subjects approaching a 200% increase, a 300% increase, or even a 400% increase.

DISCUSSION

Vibrotactile stimulation combining a first vibrotactile stimulator having a vibrating rate of 70 Hz and a second vibrotactile stimulator having a vibrating rate of 110 Hz has been shown to increase swallowing in healthy volunteers. It is expected that vibrotactile stimulation combining a first vibrotactile stimulator having a vibrating rate of 30 Hz and a second vibrotactile stimulator having a vibrating rate of 70 Hz would provide at least as much of an increase in swallowing in healthy volunteers, for example because vibrating frequencies less than 100 Hz tend to be more beneficial than vibrating frequencies greater than 100 Hz. A stimulator that has a single vibrating frequency is not as effective at eliciting swallowing as a stimulator that has two different vibrating frequencies. The effect of hybrid, two vibrating frequency, stimulation appears to have a lasting effect increasing swallowing, also during intervals between stimulation. The increase in swallowing due to hybrid stimulation is greater and more uniform than the increase in swallowing due to a single vibrating frequency. Pulsed and continuous hybrid stimulation are both effective at eliciting swallowing to similar degrees.

Although this invention has been disclosed in the context of certain embodiments and examples, the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent based upon this disclosure. Various combinations or sub-combinations of the specific features and aspects of the embodiments may be made and still fall within the scope of the invention. Various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 30 Hz" includes "30 Hz." Terms or phrases preceded by a term such as "substantially" include the recited term or phrase. For example, "substantially perpendicular" includes "perpendicular."

EXAMPLE EMBODIMENTS

The following example embodiments identify some possible permutations of combinations of features disclosed herein, although other permutations of combinations of features are also possible.

1. A device comprising:
    a first vibrotactile stimulator configured to operate at a first vibrating rate;
    a second vibrotactile stimulator configured to operate at a second vibrating rate different than the first vibrating rate; and
    a collar configured to position the first vibrotactile stimulator and the second vibrotactile stimulator over a neck of a subject.

2. The device of Embodiment 1, further comprising a switch configured to activate the first vibrotactile stimulator and the second vibrotactile stimulator, the switch configured to be volitionally operated by the subject.

3. The device of Embodiment 1 or 2, further comprising an automatic clock configured to activate the first vibrotactile stimulator and the second vibrotactile stimulator.

4. The device of any one of Embodiments 1-3, wherein the first vibrotactile stimulator and the second vibrotactile stimulator are configured to operate at partially simultaneously.

5. The device of any one of Embodiments 1-4, wherein the first vibrating rate is between about 30 Hz and about 60 Hz and the second vibrating rate is between about 60 Hz and about 80 Hz.

6. The device of any one of Embodiments 1-4, wherein the first vibrating rate is between about 50 Hz and about 90 Hz and the second vibrating rate is between about 90 Hz and about 130 Hz.

7. The device of any one of Embodiments 1-4, wherein the first vibrating rate is about 30 Hz and the second vibrating rate is about 70 Hz.

8. The device of any one of Embodiments 1-4, wherein the first vibrating rate is about 70 Hz and the second vibrating rate is about 110 Hz.

9. A method for stimulating swallowing in a subject, the method comprising:
    applying a first vibrotactile stimulation to a throat area of the subject, the first vibrotactile stimulation having a first vibrating property; and
    applying a second vibrotactile stimulation to the throat area of the subject, the second vibrotactile stimulation having a second vibrating property different than the first vibrating property.

10. The method of Embodiment 9, wherein applying the first vibrotactile stimulation and applying the second vibrotactile stimulation includes the subject voluntary activating a first vibrational transducer and a second vibrational transducer.

11. The method of Embodiment 9 or 10, wherein applying the first vibrotactile stimulation and applying the second vibrotactile stimulation includes automatically activating a first vibrational transducer and a second vibrational transducer.

12. The method of Embodiment 11, wherein automatically activating the first vibrational transducer and the second vibrational transducer includes coordinating automatically activating the first vibrational transducer and the second vibrational transducer with a monitored bodily parameter.

13. The method of any one of Embodiments 9-12, wherein applying the first vibrotactile stimulation is at least partially simultaneous with applying the second vibrotactile stimulation.

14. The method of any one of Embodiments 9-13, wherein the first vibrating property comprises a first vibrating frequency and the second vibrating property comprises a second vibrating frequency different than the first vibrating frequency.

15. The method of Embodiment 14, wherein the first vibrating rate is between about 30 Hz and about 60 Hz and the second vibrating rate is between about 60 Hz and about 80 Hz.

16. The method of Embodiment 14, wherein the first vibrating rate is between about 50 Hz and about 90 Hz and the second vibrating rate is between about 90 Hz and about 130 Hz.

17. The method of Embodiment 14, wherein the first vibrating rate is about 30 Hz and the second vibrating rate is about 70 Hz.

18. The method of Embodiment 14, wherein the first vibrating rate is about 70 Hz and the second vibrating rate is about 110 Hz.

19. The method of any one of Embodiments 7-18, wherein the first vibrating property comprises a first vibrating frequency range and the second vibrating property comprises a second vibrating frequency range different than the first vibrating frequency range.

20. The method of Embodiment 19, wherein the first vibrating rate range is between about 30 Hz and about 60 Hz and the second vibrating rate range is between about 60 Hz and about 80 Hz.

21. The method of Embodiment 19, wherein the first vibrating rate range is between about 50 Hz and about 90 Hz and the second vibrating rate range is between about 90 Hz and about 130 Hz.

22. The method of any one of Embodiments 7-21, wherein the first vibrating property comprises a first wave shape and the second vibrating property comprises a second wave shape different than the first wave shape.

23. The method of Embodiment 22, wherein the first wave shape comprises sinusoidal and the second wave shape comprises saw-tooth.

24. The method of Embodiment 22, wherein the first wave shape comprises sinusoidal and the second wave shape comprises triangular.

25. The method of Embodiment 22, wherein the first wave shape comprises sinusoidal and the second wave shape comprises square.

26. The method of Embodiment 22, wherein the first wave shape comprises saw-tooth and the second wave shape comprises triangular.

27. The method of Embodiment 22, wherein the first wave shape comprises saw-tooth and the second wave shape comprises square.

28. The method of Embodiment 22, wherein the first wave shape comprises triangular and the second wave shape comprises square.

29. The method of any one of Embodiments 7-28, wherein the first vibrating property comprises a first vibrating frequency and the second vibrating property comprises a second vibrating frequency out of phase with the first vibrating frequency.

30. The method of Embodiment 29, wherein the first vibrating frequency and the second vibrating frequency are between about 150° and about 210° out of phase.

31. The method of Embodiment 29, wherein the first vibrating frequency and the second vibrating frequency are about 180° out of phase.

32. The method of any one of Embodiments 7-31, wherein the first vibrating property comprises a continuous vibrating frequency and the second vibrating property comprises a pulsed vibrating frequency.

33. The method of any one of Embodiments 7-32, wherein the first vibrating property comprises a first direction of mechanical force and the second vibrating property comprises a second direction of mechanical force different than the first direction of mechanical force.

34. The method of Embodiment 33, wherein one of the first direction of mechanical force and the second direction of mechanical force is substantially perpendicular.

35. The method of Embodiment 33 or 34, wherein one of the first direction of mechanical force and the second direction of mechanical force is non-perpendicular and non-parallel.

36. A device comprising:
a first vibrational transducer having a first vibrating property;
a second vibrational transducer having a second vibrating property different than the first vibrating property; and
a collar configured to position the first vibrational transducer and the second vibrational transducer over a neck of a subject.

37. The device of Embodiment 36, further comprising a switch configured to activate the first vibrational transducer and the second vibrational transducer, the switch configured to be volitionally operated by the subject.

38. The device of Embodiment 36 or 37, further comprising an automatic clock configured to activate the first vibrational transducer and the second vibrational transducer.

39. The device of any one of Embodiments 36-38, wherein the first vibrational transducer and the second vibrational transducer are configured to operate at partially simultaneously.

40. The device of any one of Embodiments 36-39, wherein the first vibrating property comprises a first vibrating frequency and the second vibrating property comprises a second vibrating frequency different than the first vibrating frequency.

41. The device of Embodiment 40, wherein the first vibrating rate is between about 30 Hz and about 60 Hz and the second vibrating rate is between about 60 Hz and about 80 Hz.

42. The device of Embodiment 40, wherein the first vibrating rate is between about 50 Hz and about 90 Hz and the second vibrating rate is between about 90 Hz and about 130 Hz.

43. The device of Embodiment 40, wherein the first vibrating rate is about 30 Hz and the second vibrating rate is about 70 Hz.

44. The device of Embodiment 40, wherein the first vibrating rate is about 70 Hz and the second vibrating rate is about 110 Hz.

45. The device of any one of Embodiments 36-44, wherein the first vibrating property comprises a first vibrating frequency range and the second vibrating property comprises a second vibrating frequency range different than the first vibrating frequency range.

46. The device of Embodiment 45, wherein the first vibrating rate range is between about 30 Hz and about 60 Hz and the second vibrating rate range is between about 60 Hz and about 80 Hz.

47. The device of Embodiment 45, wherein the first vibrating rate range is between about 50 Hz and about 90 Hz and the second vibrating rate range is between about 90 Hz and about 130 Hz.

48. The device of any one of Embodiments 36-47, wherein the first vibrating property comprises a first wave shape and the second vibrating property comprises a second wave shape different than the first wave shape.

49. The device of Embodiment 48, wherein the first wave shape comprises sinusoidal and the second wave shape comprises saw-tooth.

50. The device of Embodiment 48, wherein the first wave shape comprises sinusoidal and the second wave shape comprises triangular.

51. The device of Embodiment 48, wherein the first wave shape comprises sinusoidal and the second wave shape comprises square.

52. The device of Embodiment 48, wherein the first wave shape comprises saw-tooth and the second wave shape comprises triangular.

53. The device of Embodiment 48, wherein the first wave shape comprises saw-tooth and the second wave shape comprises square.

54. The device of Embodiment 48, wherein the first wave shape comprises triangular and the second wave shape comprises square.

55. The device of any one of Embodiments 36-54, wherein the first vibrating property comprises a first vibrating frequency and the second vibrating property comprises a second vibrating frequency out of phase with the first vibrating frequency.

56. The device of Embodiment 55, wherein the first vibrating frequency and the second vibrating frequency are between about 150° and about 210° out of phase.

57. The device of Embodiment 55, wherein the first vibrating frequency and the second vibrating frequency are about 180° out of phase.

58. The device of any one of Embodiments 36-57, wherein the first vibrating property comprises a continuous vibrating frequency and the second vibrating property comprises a pulsed vibrating frequency.

59. The device of any one of Embodiments 36-58, wherein the first vibrating property comprises a first direction of mechanical force and the second vibrating property comprises a second direction of mechanical force different than the first direction of mechanical force.

60. The device of Embodiment 59, wherein one of the first direction of mechanical force and the second direction of mechanical force is substantially perpendicular.

61. The device of Embodiment 59 or 60, wherein one of the first direction of mechanical force and the second direction of mechanical force is non-perpendicular and non-parallel.

What is claimed is:

1. A device comprising:
   a first vibrotactile stimulator;
   a second vibrotactile stimulator;
   electronic components configured to set the first vibrotactile stimulator to operate at a first vibrating rate and set the second vibrotactile stimulator to operate at a second vibrating rate different than the first vibrating rate; and
   a collar configured to position the first vibrotactile stimulator and the second vibrotactile stimulator over a neck of a subject,
   wherein the first vibrating rate is between 50 Hz and 90 Hz and the second vibrating rate is between 90 Hz and 130 Hz.

2. The device of claim 1, further comprising a switch configured to activate the first vibrotactile stimulator and the second vibrotactile stimulator, the switch configured to be volitionally operated by the subject.

3. The device of claim 1, further comprising an automatic clock configured to activate the first vibrotactile stimulator and the second vibrotactile stimulator.

4. The device of claim 1, wherein the first vibrotactile stimulator and the second vibrotactile stimulator are configured to operate at partially simultaneously.

5. The device of claim 1, wherein the first vibrating rate is constant and the second vibrating rate is constant.

6. The device of claim 1, further comprising adjustment controls configured to adjust the first vibrating rate and the second vibrating rate.

7. A device comprising:
   a first vibrational stimulator;
   a second vibrational stimulator;
   electronic components configured to set the first vibrational stimulator to operate at a first vibrating rate and set the second vibrational stimulator to operate at a second vibrating rate different than the first vibrating rate; and
   a collar configured to position the first vibrational stimulator and the second vibrational stimulator over a neck of a subject,
   wherein the second vibrating rate is at least 30 Hz greater than the first vibrating rate.

8. The device of claim 7, further comprising a switch configured to activate the first vibrational stimulator and the second vibrational stimulator, the switch configured to be volitionally operated by the subject.

9. The device of claim 7, further comprising an automatic clock configured to activate the first vibrational stimulator and the second vibrational stimulator.

10. The device of claim 7, wherein the first vibrational stimulator and the second vibrational stimulator are configured to operate at partially simultaneously.

11. The device of claim 7, wherein the first vibrating rate is constant and the second vibrating rate is constant.

12. The device of claim 7, wherein the first vibrating rate is between 50 Hz and 90 Hz and the second vibrating rate is between 90 Hz and 130 Hz.

13. The device of claim 7, further comprising adjustment controls configured to adjust the first vibrating rate and the second vibrating rate.

* * * * *